US011905529B2

(12) United States Patent
Alpert

(10) Patent No.: US 11,905,529 B2
(45) Date of Patent: Feb. 20, 2024

(54) METHOD OF ENHANCING PERSISTENCE OF ADOPTIVELY INFUSED T CELLS

(71) Applicant: Immatics US, Inc., Houston, TX (US)

(72) Inventor: Amir Alpert, Houston, TX (US)

(73) Assignee: Immatics US INC., Houston, TX (US)

(*) Notice: Subject to any disclaimer, the term of this patent is extended or adjusted under 35 U.S.C. 154(b) by 524 days.

(21) Appl. No.: 17/062,234

(22) Filed: Oct. 2, 2020

(65) Prior Publication Data

US 2021/0017493 A1 Jan. 21, 2021

Related U.S. Application Data

(63) Continuation of application No. 16/361,043, filed on Mar. 21, 2019, now abandoned.

(60) Provisional application No. 62/646,180, filed on Mar. 21, 2018.

(30) Foreign Application Priority Data

Apr. 11, 2018 (DE) ............ 10 2018 108 612.1

(51) Int. Cl.
  *C12N 5/0783* (2010.01)
  *A61P 35/00* (2006.01)
  *A61K 35/17* (2015.01)

(52) U.S. Cl.
  CPC ............ *C12N 5/0636* (2013.01); *A61K 35/17* (2013.01); *A61P 35/00* (2018.01)

(58) Field of Classification Search
  None
  See application file for complete search history.

(56) References Cited

U.S. PATENT DOCUMENTS

| | | | |
|---|---|---|---|
| 6,352,694 | B1 | 3/2002 | June et al. |
| 6,399,054 | B1 | 6/2002 | Casorati et al. |
| 7,993,638 | B2 | 8/2011 | Cai et al. |
| 8,906,682 | B2 | 12/2014 | June et al. |
| 8,916,381 | B1 | 12/2014 | June et al. |
| 9,402,865 | B2 | 8/2016 | Powell et al. |
| 9,499,629 | B2 | 11/2016 | June et al. |
| 10,538,572 | B2 | 1/2020 | Schmitt et al. |
| 2014/0356398 | A1 | 12/2014 | Riddell et al. |
| 2015/0017120 | A1 | 1/2015 | Wittrup et al. |
| 2015/0024482 | A1 | 1/2015 | Frigault et al. |
| 2017/0051252 | A1 | 2/2017 | Morgan et al. |
| 2017/0087185 | A1 | 3/2017 | Crane et al. |
| 2017/0296641 | A1 | 10/2017 | Weinschenk et al. |
| 2017/0349880 | A1 | 12/2017 | Doucet et al. |

FOREIGN PATENT DOCUMENTS

| | | |
|---|---|---|
| CN | 106456670 A | 2/2017 |
| CN | 107074970 A | 8/2017 |
| JP | 2017-513891 A | 6/2017 |
| WO | 2015/164745 A1 | 10/2015 |
| WO | 2016/168595 A1 | 10/2016 |

OTHER PUBLICATIONS

Petersen, et al., "Improving T-cell expansion and function for adoptive T-cell therapy using ex vivo treatment with PI3K[delta] inhibitors and VIP antagonists," Blood Adv., (2018), vol. 2, No. 3: 210-223.
Perro, et al., "Generation of multi-functional antigen-specific human T-cells by lentiviral TCR gene transfer," Gene Ther., (2010), vol. 17, No. 6: 721-32.
Berger et al., "Adoptive transfer of effector CD8+ T cells derived from central memory cells establishes persisten T cell memory in primates" The Journal of Clinical Investigation. (2008) vol. 118, No. 1: 294-306.
"Complex Biology In Vitro Assays: Immuno-Oncology Cytokine Response Assay" Charles River. (2018) pp. 1-3.
Larsen et al., "Differntial cytokine withdrawal-induced death sensitivity of effector T cells derived from distinct human CD8+ memory subsets" Cell Death Discovery. vol. 3. (2017) pp. 1-8.
Larsen et al., "Sensitivity to restimulation-induced cell death is linked to glycolytic metabolism in human T cells" J Immunol. (2017) 198(1): 147-155.
Lee et al., "The Future is Now: Chimeric Antigen Receptors as New Targeted Therapies for Childhood Cancer" Clin Cancer Res. (May 15, 2012) 18(10): 2780-2790.
Liu et al., "Novel T cells with improved in vivo anti-tumor activity generated by RNA electroporation" Protein Cell (2017) 8(7): 514-526.
Redeker et al., "Improving Adoptive T Cell Therapy: The Particular Role of T Cell Costimulation, Cytokines, and Post-Transfer Vaccination" Frontiers in Immunology. (Sep. 2016) vol. 7, Article 345, pp. 1-17.
Smith et al., "Ex vivo expansion of human T cells for adoptive immunotherapy using the novel Xeno-free CTS Immune Cell Serum Replacement" Clinical & Translational Immunology. (2015) vol. 4: 1-10.
Snow et al., "The Power and the Promise of Restimulation-Induced Cell Death in Human Immune Diseases" Immunol Rev. (Jul. 2010) vol. 236: 68-82.
Peterson CT, Hassan M, Morris AB, et al. Improving T-cell expansion and function for adoptive T-cell therapy using ex vivo treatment with PI3Kδ inhibitors and VIP antagonists. Blood Adv. (2018) ; 2(3):210-223.
Perron et al., "Generation of multi-functional antigen-specific human T-cells by lentiviral TCR gene transfer" Gene Therapy vol. 17, pp. 721-732 (2010).

(Continued)

*Primary Examiner* — Amy E Juedes
(74) *Attorney, Agent, or Firm* — McBee Moore & Vanik IP, LLC

(57) ABSTRACT

The present disclosure provides for methods of improving the efficacy of T cells. In an aspect, the disclosure further provides for methods of enhancing the persistence of T cells for adoptive cell transfer or therapy (ACT). Cytokine sensitivity assays (CSA) and associated methodology capable of predicting the persistence of adoptively infused T Cells are further provided for by way of the instant disclosure. The disclosure also provides for methods of treating cancer in a subject in need thereof as well as T cells populations produced by methods described herein.

20 Claims, 37 Drawing Sheets

Specification includes a Sequence Listing.

(56) References Cited

OTHER PUBLICATIONS

International Search Report issued in counterpart application No. PCT/US19/23104, dated Jun. 6, 2019.

Cha, Esther, et al. "IL-7+IL-15 are superior to IL-2 for the ex vivo expansion of 4T1 mammary carcinoma-specific T cells with greater efficacy against tumors in vivo" Breast Cancer Research Treatment, vol. 122, No. 2, pp. 359-369, Jul. 2010.

Cieri, Nicoletta, et al. "IL-7 and IL-15 instruct the generation of human memory stem T cells from naive precursors" Blood, vol. 121, No. 4, pp. 573-584, Jan. 2013.

Ghassemi, Saba, et al. "Shortened T Cell Culture with IL-7 and IL-15 Provides the Most Potent Chimeric Antigen Receptor (CAR)-Modified T Cells for Adoptive Immunotherapy", Molecular Therapy, vol. 24, Supplemental 1, S29, May 2016.

Matis, L.A., et al. "Adoptive Immunotherapy of a syngeneic murine leukemia with a tumor-specific cytotoxic T cell clone and recombinant human interleukin 2: correlation with clonal IL 2 receptor expression" Journal of Immunology, vol. 136, No. 9, pp. 3496-3501, May 1986.

Montes, M., et al. "Optimum in vitro expansion of human antigen-specific CD8+ T cells for adoptive transfer therapy" Clinical Experimental Immunology, vol. 142, No. 2, pp. 292-302, Nov. 2005.

Oelke, M., et al. "Generation and purification of CD8+ melan-A-specific cytotoxic T lymphocytes for adoptive transfer in tumor immunotherapy" Clinical Cancer Research, vol. 6, No. 5, pp. 1997-2005, May 2000.

Wolfl, Matthias, et al. "Antigen-specific activation and cytokine-facilitated expansion of naive, human CD8+ T cells" Nat. Protoc. vol. 9, No. 4, pp. 950-966, Apr. 2014.

Yamazaki, Takamasa, et al. "Characterization of Immobilized Anti-CD3 Antibody-activated T Lymphocytes for Use in Adoptive Immunotherapy of Patients with Brain Tumors" Neurol Med Chir (Tokyo) vol. 32, No. 5, pp. 255-261, May 1992.

Riddell et al., "The Use of anti-CD3 and anti-CD28 monoclonal antibodies to clone and expand human antigen-specific T cells", Journal of Immunnological Methods, 1990, pp. 189-201, vol. 128.

Montes et al., "Optimum in vitro expansion of human antigen-specific CD8+ Tcells for adoptive transfer therapy", Clinical and Experimental Immunology, 2005, pp. 292-302, vol. 142.

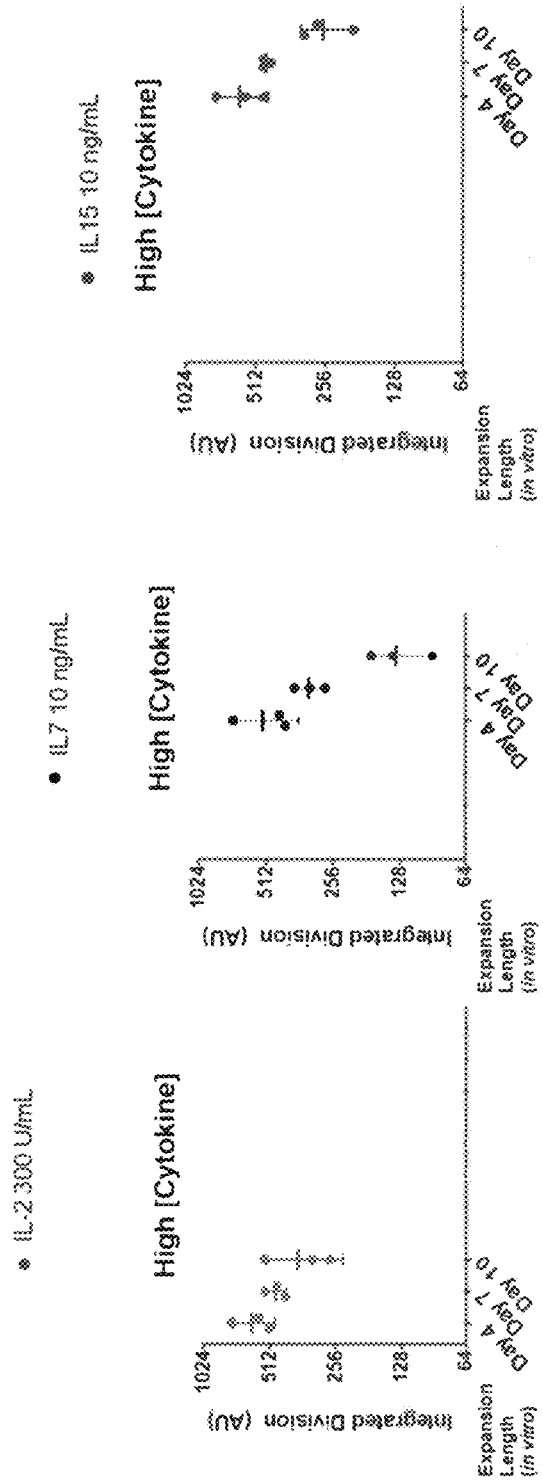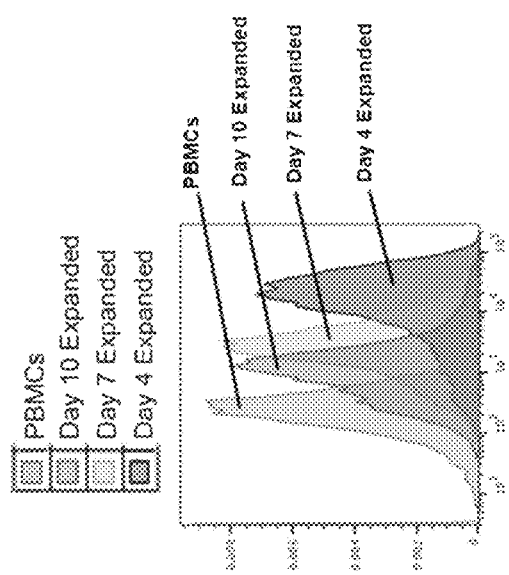
FIG. 16A  FIG. 16B  FIG. 16C  FIG. 16D

FIG. 21B Day 7
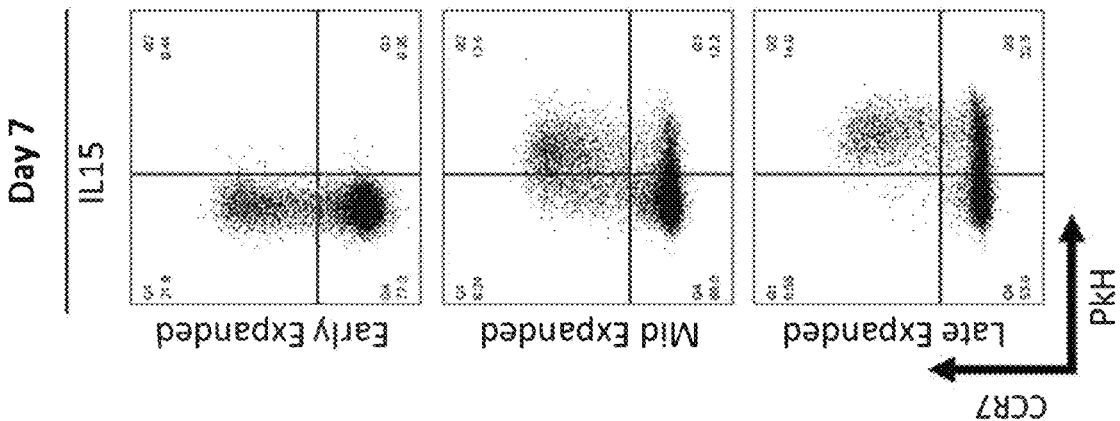
FIG. 21A Day 21
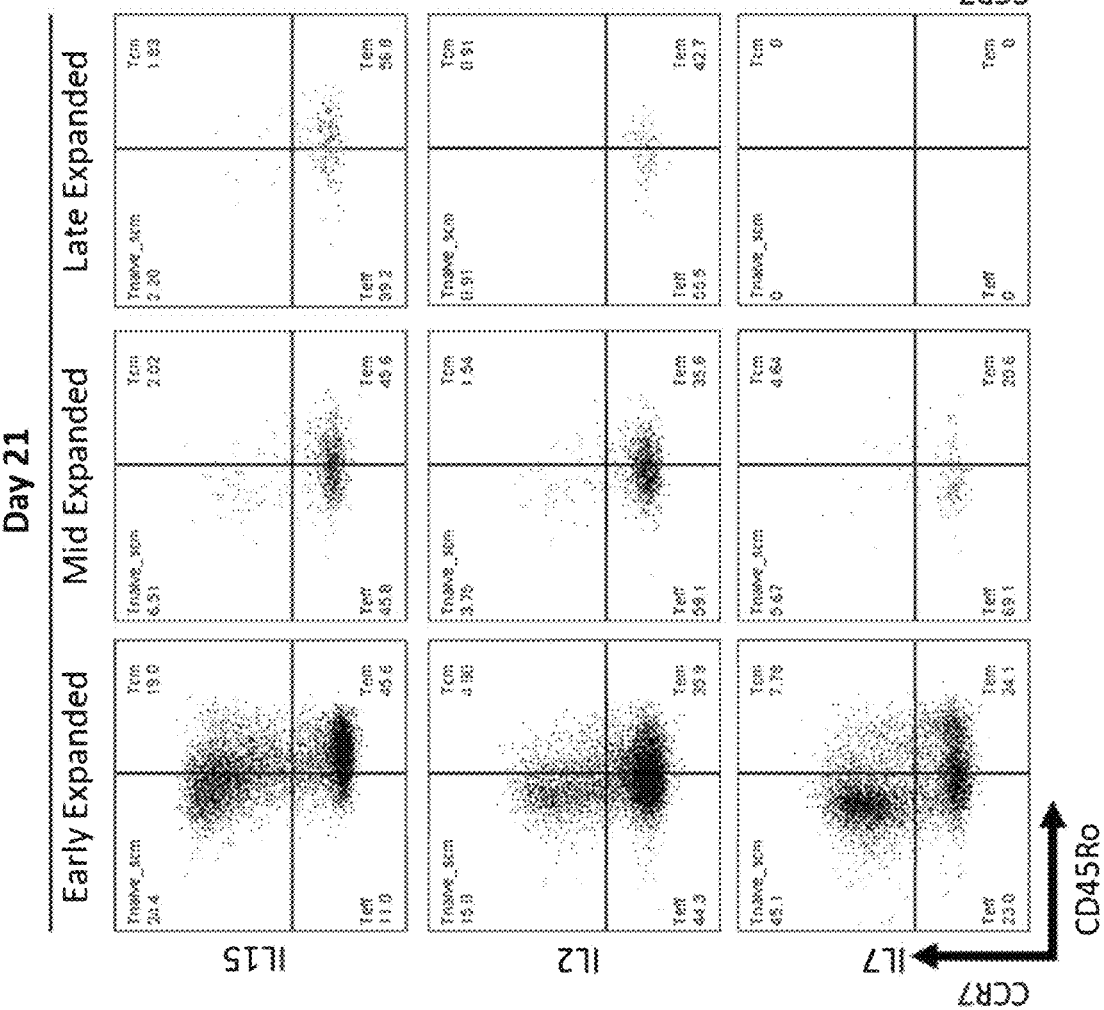

FIG. 28
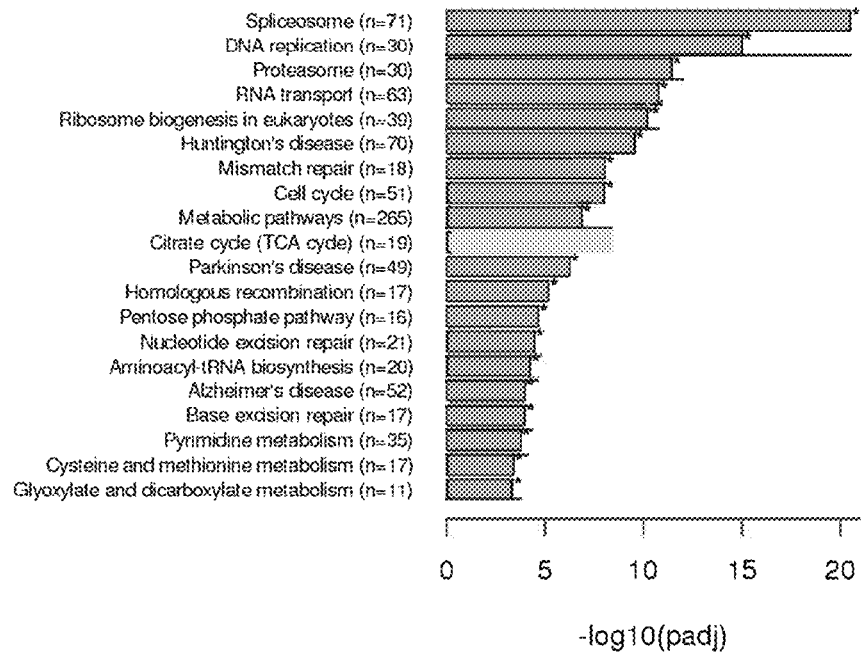
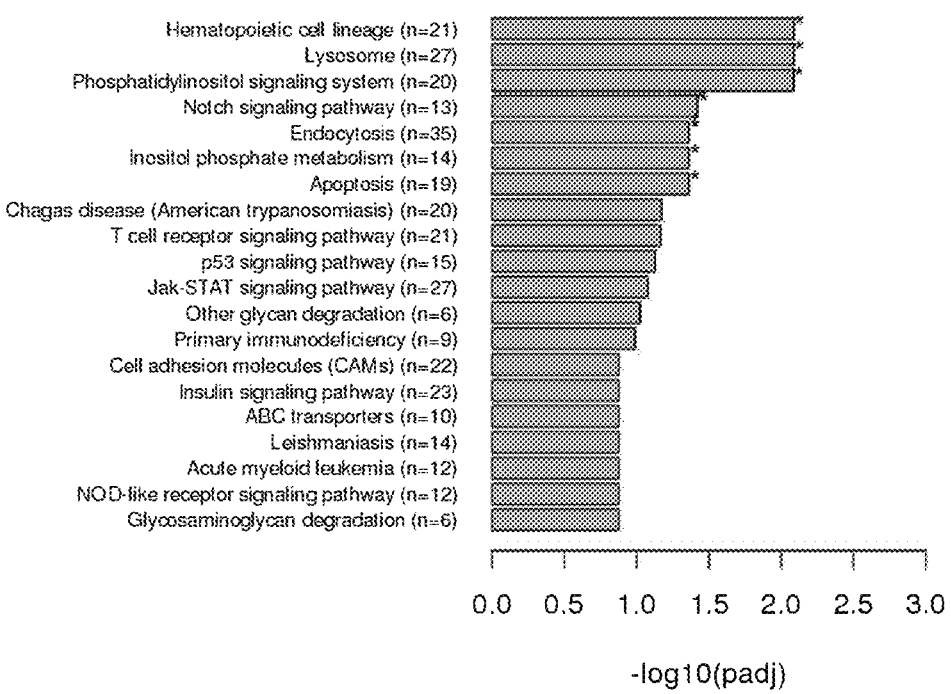

FIG. 28 (continued)
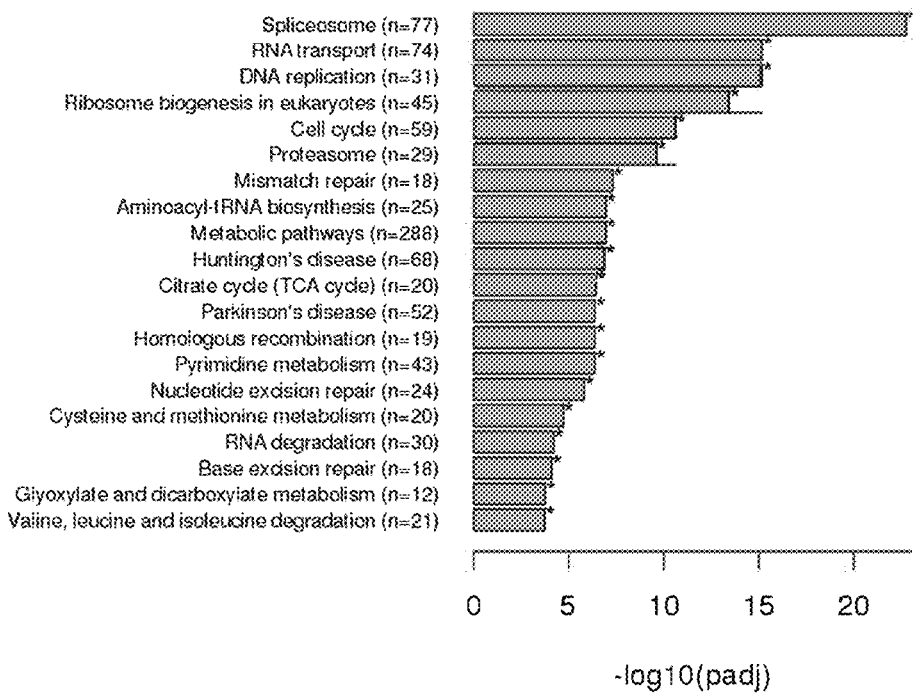
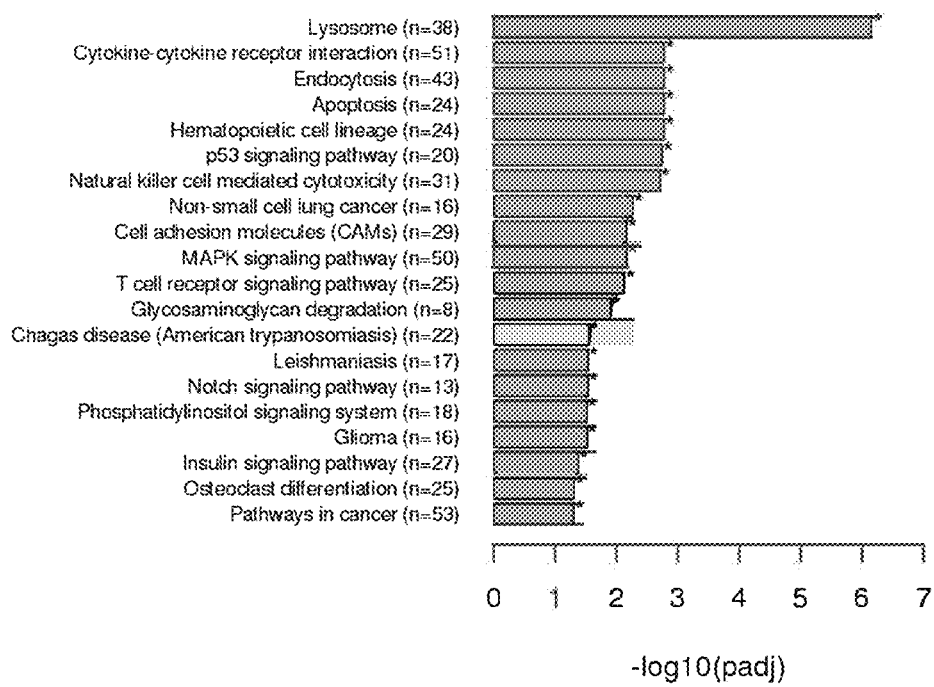

FIG. 28 (continued)
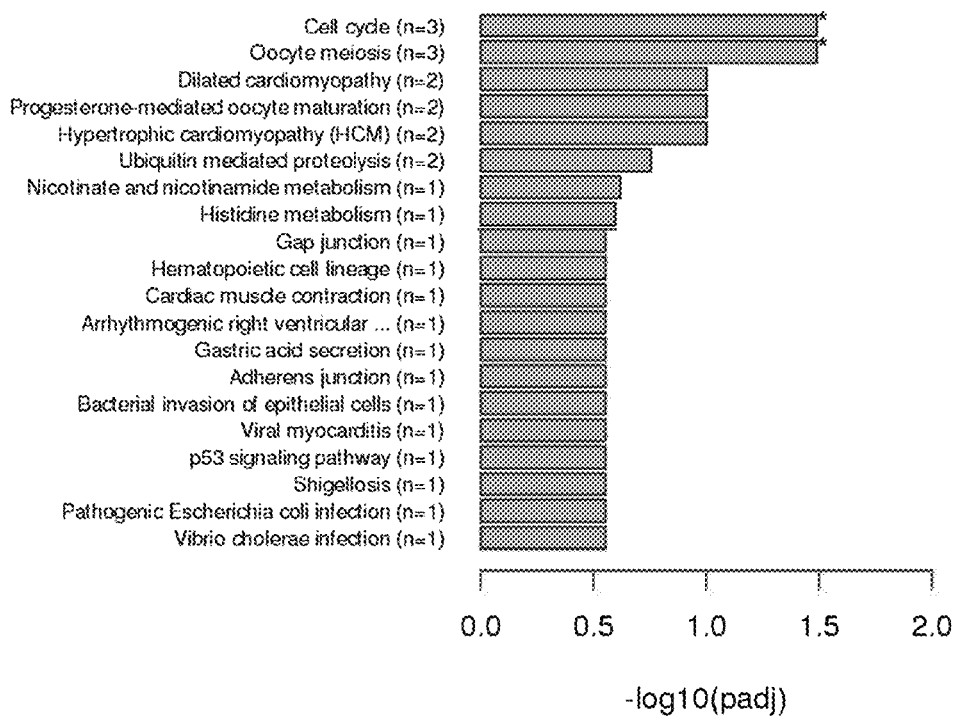
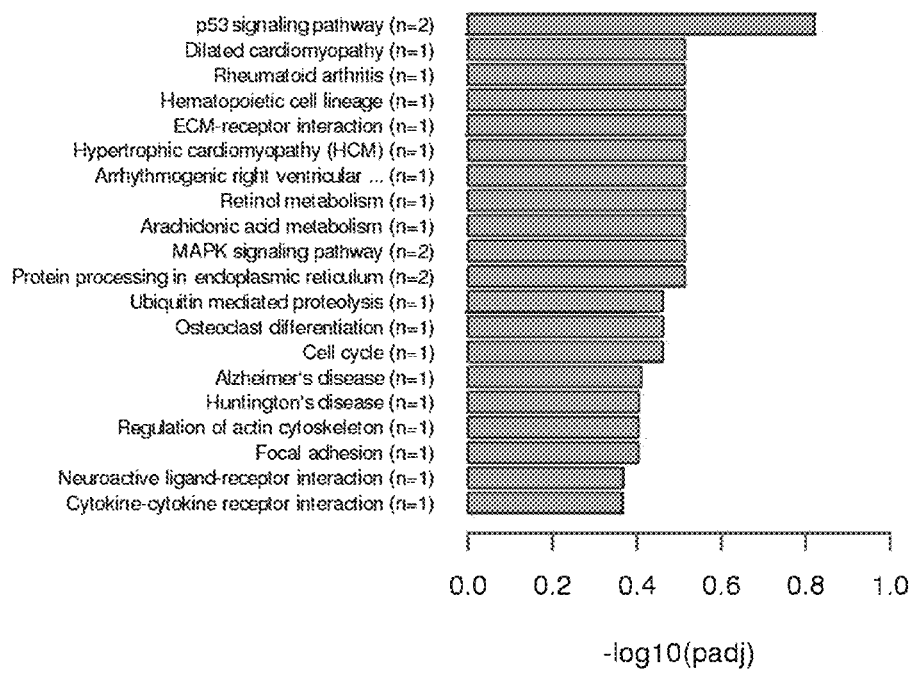

SEQUENCE LISTING

```
<160> NUMBER OF SEQ ID NOS: 157

<210> SEQ ID NO 1
<211> LENGTH: 10
<212> TYPE: PRT
<213> ORGANISM: Homo sapiens

<400> SEQUENCE: 1

Tyr Leu Tyr Asp Ser Glu Thr Lys Asn Ala
 1               5                  10

<210> SEQ ID NO 2
<211> LENGTH: 9
<212> TYPE: PRT
<213> ORGANISM: Homo sapiens

<400> SEQUENCE: 2

His Leu Met Asp Gln Pro Leu Ser Val
 1               5

<210> SEQ ID NO 3
<211> LENGTH: 9
<212> TYPE: PRT
<213> ORGANISM: Homo sapiens

<400> SEQUENCE: 3

Gly Leu Leu Lys Lys Ile Asn Ser Val
 1               5

<210> SEQ ID NO 4
<211> LENGTH: 9
<212> TYPE: PRT
<213> ORGANISM: Homo sapiens

<400> SEQUENCE: 4

Phe Leu Val Asp Gly Ser Ser Ala Leu
 1               5

<210> SEQ ID NO 5
<211> LENGTH: 10
<212> TYPE: PRT
<213> ORGANISM: Homo sapiens

<400> SEQUENCE: 5

Phe Leu Phe Asp Gly Ser Ala Asn Leu Val
 1               5                  10

<210> SEQ ID NO 6
<211> LENGTH: 9
<212> TYPE: PRT
<213> ORGANISM: Homo sapiens

<400> SEQUENCE: 6

Phe Leu Tyr Lys Ile Ile Asp Glu Leu
 1               5

<210> SEQ ID NO 7
<211> LENGTH: 11
<212> TYPE: PRT
<213> ORGANISM: Homo sapiens

<400> SEQUENCE: 7

Phe Ile Leu Asp Ser Ala Glu Thr Thr Thr Leu
 1               5                  10
```

```
<210> SEQ ID NO 8
<211> LENGTH: 9
<212> TYPE: PRT
<213> ORGANISM: Homo sapiens

<400> SEQUENCE: 8

Ser Val Asp Val Ser Pro Pro Lys Val
1               5

<210> SEQ ID NO 9
<211> LENGTH: 8
<212> TYPE: PRT
<213> ORGANISM: Homo sapiens

<400> SEQUENCE: 9

Val Ala Asp Lys Ile His Ser Val
1               5

<210> SEQ ID NO 10
<211> LENGTH: 9
<212> TYPE: PRT
<213> ORGANISM: Homo sapiens

<400> SEQUENCE: 10

Ile Val Asp Asp Leu Thr Ile Asn Leu
1               5

<210> SEQ ID NO 11
<211> LENGTH: 9
<212> TYPE: PRT
<213> ORGANISM: Homo sapiens

<400> SEQUENCE: 11

Gly Leu Leu Glu Glu Leu Val Thr Val
1               5

<210> SEQ ID NO 12
<211> LENGTH: 10
<212> TYPE: PRT
<213> ORGANISM: Homo sapiens

<400> SEQUENCE: 12

Thr Leu Asp Gly Ala Ala Val Asn Gln Val
1               5                   10

<210> SEQ ID NO 13
<211> LENGTH: 10
<212> TYPE: PRT
<213> ORGANISM: Homo sapiens

<400> SEQUENCE: 13

Ser Val Leu Glu Lys Glu Ile Tyr Ser Ile
1               5                   10

<210> SEQ ID NO 14
<211> LENGTH: 9
<212> TYPE: PRT
<213> ORGANISM: Homo sapiens

<400> SEQUENCE: 14

Leu Leu Asp Pro Lys Thr Ile Phe Leu
1               5

<210> SEQ ID NO 15
```

```
<211> LENGTH: 9
<212> TYPE: PRT
<213> ORGANISM: Homo sapiens

<400> SEQUENCE: 15

Tyr Thr Phe Ser Gly Asp Val Gln Leu
1               5

<210> SEQ ID NO 16
<211> LENGTH: 9
<212> TYPE: PRT
<213> ORGANISM: Homo sapiens

<400> SEQUENCE: 16

Tyr Leu Met Asp Asp Phe Ser Ser Leu
1               5

<210> SEQ ID NO 17
<211> LENGTH: 9
<212> TYPE: PRT
<213> ORGANISM: Homo sapiens

<400> SEQUENCE: 17

Lys Val Trp Ser Asp Val Thr Pro Leu
1               5

<210> SEQ ID NO 18
<211> LENGTH: 11
<212> TYPE: PRT
<213> ORGANISM: Homo sapiens

<400> SEQUENCE: 18

Leu Leu Trp Gly His Pro Arg Val Ala Leu Ala
1               5                   10

<210> SEQ ID NO 19
<211> LENGTH: 11
<212> TYPE: PRT
<213> ORGANISM: Homo sapiens

<400> SEQUENCE: 19

Lys Ile Trp Glu Glu Leu Ser Val Leu Glu Val
1               5                   10

<210> SEQ ID NO 20
<211> LENGTH: 9
<212> TYPE: PRT
<213> ORGANISM: Homo sapiens

<400> SEQUENCE: 20

Leu Leu Ile Pro Phe Thr Ile Phe Met
1               5

<210> SEQ ID NO 21
<211> LENGTH: 9
<212> TYPE: PRT
<213> ORGANISM: Homo sapiens

<400> SEQUENCE: 21

Phe Leu Ile Glu Asn Leu Leu Ala Ala
1               5

<210> SEQ ID NO 22
<211> LENGTH: 11
<212> TYPE: PRT
```

```
<213> ORGANISM: Homo sapiens

<400> SEQUENCE: 22

Leu Leu Trp Gly His Pro Arg Val Ala Leu Ala
1               5                   10

<210> SEQ ID NO 23
<211> LENGTH: 9
<212> TYPE: PRT
<213> ORGANISM: Homo sapiens

<400> SEQUENCE: 23

Phe Leu Leu Glu Arg Glu Gln Leu Leu
1               5

<210> SEQ ID NO 24
<211> LENGTH: 9
<212> TYPE: PRT
<213> ORGANISM: Homo sapiens

<400> SEQUENCE: 24

Ser Leu Ala Glu Thr Ile Phe Ile Val
1               5

<210> SEQ ID NO 25
<211> LENGTH: 9
<212> TYPE: PRT
<213> ORGANISM: Homo sapiens

<400> SEQUENCE: 25

Thr Leu Leu Glu Gly Ile Ser Arg Ala
1               5

<210> SEQ ID NO 26
<211> LENGTH: 9
<212> TYPE: PRT
<213> ORGANISM: Homo sapiens

<400> SEQUENCE: 26

Ile Leu Gln Asp Gly Gln Phe Leu Val
1               5

<210> SEQ ID NO 27
<211> LENGTH: 10
<212> TYPE: PRT
<213> ORGANISM: Homo sapiens

<400> SEQUENCE: 27

Val Ile Phe Glu Gly Glu Pro Met Tyr Leu
1               5                   10

<210> SEQ ID NO 28
<211> LENGTH: 9
<212> TYPE: PRT
<213> ORGANISM: Homo sapiens

<400> SEQUENCE: 28

Ser Leu Phe Glu Ser Leu Glu Tyr Leu
1               5

<210> SEQ ID NO 29
<211> LENGTH: 9
<212> TYPE: PRT
<213> ORGANISM: Homo sapiens
```

<400> SEQUENCE: 29

Ser Leu Leu Asn Gln Pro Lys Ala Val
1               5

<210> SEQ ID NO 30
<211> LENGTH: 9
<212> TYPE: PRT
<213> ORGANISM: Homo sapiens

<400> SEQUENCE: 30

Gly Leu Ala Glu Phe Gln Glu Asn Val
1               5

<210> SEQ ID NO 31
<211> LENGTH: 9
<212> TYPE: PRT
<213> ORGANISM: Homo sapiens

<400> SEQUENCE: 31

Lys Leu Leu Ala Val Ile His Glu Leu
1               5

<210> SEQ ID NO 32
<211> LENGTH: 9
<212> TYPE: PRT
<213> ORGANISM: Homo sapiens

<400> SEQUENCE: 32

Thr Leu His Asp Gln Val His Leu Leu
1               5

<210> SEQ ID NO 33
<211> LENGTH: 11
<212> TYPE: PRT
<213> ORGANISM: Homo sapiens

<400> SEQUENCE: 33

Thr Leu Tyr Asn Pro Glu Arg Thr Ile Thr Val
1               5                   10

<210> SEQ ID NO 34
<211> LENGTH: 9
<212> TYPE: PRT
<213> ORGANISM: Homo sapiens

<400> SEQUENCE: 34

Lys Leu Gln Glu Lys Ile Gln Glu Leu
1               5

<210> SEQ ID NO 35
<211> LENGTH: 10
<212> TYPE: PRT
<213> ORGANISM: Homo sapiens

<400> SEQUENCE: 35

Ser Val Leu Glu Lys Glu Ile Tyr Ser Ile
1               5                   10

<210> SEQ ID NO 36
<211> LENGTH: 11
<212> TYPE: PRT
<213> ORGANISM: Homo sapiens

<400> SEQUENCE: 36

Arg Val Ile Asp Asp Ser Leu Val Val Gly Val
1               5                   10

<210> SEQ ID NO 37
<211> LENGTH: 9
<212> TYPE: PRT
<213> ORGANISM: Homo sapiens

<400> SEQUENCE: 37

Val Leu Phe Gly Glu Leu Pro Ala Leu
1               5

<210> SEQ ID NO 38
<211> LENGTH: 9
<212> TYPE: PRT
<213> ORGANISM: Homo sapiens

<400> SEQUENCE: 38

Gly Leu Val Asp Ile Met Val His Leu
1               5

<210> SEQ ID NO 39
<211> LENGTH: 9
<212> TYPE: PRT
<213> ORGANISM: Homo sapiens

<400> SEQUENCE: 39

Phe Leu Asn Ala Ile Glu Thr Ala Leu
1               5

<210> SEQ ID NO 40
<211> LENGTH: 9
<212> TYPE: PRT
<213> ORGANISM: Homo sapiens

<400> SEQUENCE: 40

Ala Leu Leu Gln Ala Leu Met Glu Leu
1               5

<210> SEQ ID NO 41
<211> LENGTH: 9
<212> TYPE: PRT
<213> ORGANISM: Homo sapiens

<400> SEQUENCE: 41

Ala Leu Ser Ser Ser Gln Ala Glu Val
1               5

<210> SEQ ID NO 42
<211> LENGTH: 11
<212> TYPE: PRT
<213> ORGANISM: Homo sapiens

<400> SEQUENCE: 42

Ser Leu Ile Thr Gly Gln Asp Leu Leu Ser Val
1               5                   10

<210> SEQ ID NO 43
<211> LENGTH: 9
<212> TYPE: PRT
<213> ORGANISM: Homo sapiens

<400> SEQUENCE: 43

Gln Leu Ile Glu Lys Asn Trp Leu Leu
1               5

```
<210> SEQ ID NO 44
<211> LENGTH: 9
<212> TYPE: PRT
<213> ORGANISM: Homo sapiens

<400> SEQUENCE: 44

Leu Leu Asp Pro Lys Thr Ile Phe Leu
1               5

<210> SEQ ID NO 45
<211> LENGTH: 9
<212> TYPE: PRT
<213> ORGANISM: Homo sapiens

<400> SEQUENCE: 45

Arg Leu His Asp Glu Asn Ile Leu Leu
1               5

<210> SEQ ID NO 46
<211> LENGTH: 9
<212> TYPE: PRT
<213> ORGANISM: Homo sapiens

<400> SEQUENCE: 46

Tyr Thr Phe Ser Gly Asp Val Gln Leu
1               5

<210> SEQ ID NO 47
<211> LENGTH: 9
<212> TYPE: PRT
<213> ORGANISM: Homo sapiens

<400> SEQUENCE: 47

Gly Leu Pro Ser Ala Thr Thr Thr Val
1               5

<210> SEQ ID NO 48
<211> LENGTH: 11
<212> TYPE: PRT
<213> ORGANISM: Homo sapiens

<400> SEQUENCE: 48

Gly Leu Leu Pro Ser Ala Glu Ser Ile Lys Leu
1               5                   10

<210> SEQ ID NO 49
<211> LENGTH: 9
<212> TYPE: PRT
<213> ORGANISM: Homo sapiens

<400> SEQUENCE: 49

Lys Thr Ala Ser Ile Asn Gln Asn Val
1               5

<210> SEQ ID NO 50
<211> LENGTH: 9
<212> TYPE: PRT
<213> ORGANISM: Homo sapiens

<400> SEQUENCE: 50

Ser Leu Leu Gln His Leu Ile Gly Leu
1               5
```

```
<210> SEQ ID NO 51
<211> LENGTH: 9
<212> TYPE: PRT
<213> ORGANISM: Homo sapiens

<400> SEQUENCE: 51

Tyr Leu Met Asp Asp Phe Ser Ser Leu
1               5

<210> SEQ ID NO 52
<211> LENGTH: 9
<212> TYPE: PRT
<213> ORGANISM: Homo sapiens

<400> SEQUENCE: 52

Leu Met Tyr Pro Tyr Ile Tyr His Val
1               5

<210> SEQ ID NO 53
<211> LENGTH: 9
<212> TYPE: PRT
<213> ORGANISM: Homo sapiens

<400> SEQUENCE: 53

Lys Val Trp Ser Asp Val Thr Pro Leu
1               5

<210> SEQ ID NO 54
<211> LENGTH: 11
<212> TYPE: PRT
<213> ORGANISM: Homo sapiens

<400> SEQUENCE: 54

Leu Leu Trp Gly His Pro Arg Val Ala Leu Ala
1               5                   10

<210> SEQ ID NO 55
<211> LENGTH: 9
<212> TYPE: PRT
<213> ORGANISM: Homo sapiens

<400> SEQUENCE: 55

Val Leu Asp Gly Lys Val Ala Val Val
1               5

<210> SEQ ID NO 56
<211> LENGTH: 9
<212> TYPE: PRT
<213> ORGANISM: Homo sapiens

<400> SEQUENCE: 56

Gly Leu Leu Gly Lys Val Thr Ser Val
1               5

<210> SEQ ID NO 57
<211> LENGTH: 9
<212> TYPE: PRT
<213> ORGANISM: Homo sapiens

<400> SEQUENCE: 57

Lys Met Ile Ser Ala Ile Pro Thr Leu
1               5

<210> SEQ ID NO 58
<211> LENGTH: 11
```

```
<212> TYPE: PRT
<213> ORGANISM: Homo sapiens

<400> SEQUENCE: 58

Gly Leu Leu Glu Thr Thr Gly Leu Leu Ala Thr
1               5                   10

<210> SEQ ID NO 59
<211> LENGTH: 9
<212> TYPE: PRT
<213> ORGANISM: Homo sapiens

<400> SEQUENCE: 59

Thr Leu Asn Thr Leu Asp Ile Asn Leu
1               5

<210> SEQ ID NO 60
<211> LENGTH: 9
<212> TYPE: PRT
<213> ORGANISM: Homo sapiens

<400> SEQUENCE: 60

Val Ile Ile Lys Gly Leu Glu Glu Ile
1               5

<210> SEQ ID NO 61
<211> LENGTH: 9
<212> TYPE: PRT
<213> ORGANISM: Homo sapiens

<400> SEQUENCE: 61

Tyr Leu Glu Asp Gly Phe Ala Tyr Val
1               5

<210> SEQ ID NO 62
<211> LENGTH: 11
<212> TYPE: PRT
<213> ORGANISM: Homo sapiens

<400> SEQUENCE: 62

Lys Ile Trp Glu Glu Leu Ser Val Leu Glu Val
1               5                   10

<210> SEQ ID NO 63
<211> LENGTH: 9
<212> TYPE: PRT
<213> ORGANISM: Homo sapiens

<400> SEQUENCE: 63

Leu Leu Ile Pro Phe Thr Ile Phe Met
1               5

<210> SEQ ID NO 64
<211> LENGTH: 10
<212> TYPE: PRT
<213> ORGANISM: Homo sapiens

<400> SEQUENCE: 64

Ile Ser Leu Asp Glu Val Ala Val Ser Leu
1               5                   10

<210> SEQ ID NO 65
<211> LENGTH: 10
<212> TYPE: PRT
<213> ORGANISM: Homo sapiens
```

```
<400> SEQUENCE: 65

Lys Ile Ser Asp Phe Gly Leu Ala Thr Val
1               5                   10

<210> SEQ ID NO 66
<211> LENGTH: 11
<212> TYPE: PRT
<213> ORGANISM: Homo sapiens

<400> SEQUENCE: 66

Lys Leu Ile Gly Asn Ile His Gly Asn Glu Val
1               5                   10

<210> SEQ ID NO 67
<211> LENGTH: 9
<212> TYPE: PRT
<213> ORGANISM: Homo sapiens

<400> SEQUENCE: 67

Ile Leu Leu Ser Val Leu His Gln Leu
1               5

<210> SEQ ID NO 68
<211> LENGTH: 9
<212> TYPE: PRT
<213> ORGANISM: Homo sapiens

<400> SEQUENCE: 68

Leu Asp Ser Glu Ala Leu Leu Thr Leu
1               5

<210> SEQ ID NO 69
<211> LENGTH: 13
<212> TYPE: PRT
<213> ORGANISM: Homo sapiens

<400> SEQUENCE: 69

Val Leu Gln Glu Asn Ser Ser Asp Tyr Gln Ser Asn Leu
1               5                   10

<210> SEQ ID NO 70
<211> LENGTH: 11
<212> TYPE: PRT
<213> ORGANISM: Homo sapiens

<400> SEQUENCE: 70

His Leu Leu Gly Glu Gly Ala Phe Ala Gln Val
1               5                   10

<210> SEQ ID NO 71
<211> LENGTH: 9
<212> TYPE: PRT
<213> ORGANISM: Homo sapiens

<400> SEQUENCE: 71

Ser Leu Val Glu Asn Ile His Val Leu
1               5

<210> SEQ ID NO 72
<211> LENGTH: 9
<212> TYPE: PRT
<213> ORGANISM: Homo sapiens

<400> SEQUENCE: 72
```

```
Tyr Thr Phe Ser Gly Asp Val Gln Leu
1               5

<210> SEQ ID NO 73
<211> LENGTH: 9
<212> TYPE: PRT
<213> ORGANISM: Homo sapiens

<400> SEQUENCE: 73

Ser Leu Ser Glu Lys Ser Pro Glu Val
1               5

<210> SEQ ID NO 74
<211> LENGTH: 10
<212> TYPE: PRT
<213> ORGANISM: Homo sapiens

<400> SEQUENCE: 74

Ala Met Phe Pro Asp Thr Ile Pro Arg Val
1               5                   10

<210> SEQ ID NO 75
<211> LENGTH: 9
<212> TYPE: PRT
<213> ORGANISM: Homo sapiens

<400> SEQUENCE: 75

Phe Leu Ile Glu Asn Leu Leu Ala Ala
1               5

<210> SEQ ID NO 76
<211> LENGTH: 9
<212> TYPE: PRT
<213> ORGANISM: Homo sapiens

<400> SEQUENCE: 76

Phe Thr Ala Glu Phe Leu Glu Lys Val
1               5

<210> SEQ ID NO 77
<211> LENGTH: 9
<212> TYPE: PRT
<213> ORGANISM: Homo sapiens

<400> SEQUENCE: 77

Ala Leu Tyr Gly Asn Val Gln Gln Val
1               5

<210> SEQ ID NO 78
<211> LENGTH: 9
<212> TYPE: PRT
<213> ORGANISM: Homo sapiens

<400> SEQUENCE: 78

Leu Phe Gln Ser Arg Ile Ala Gly Val
1               5

<210> SEQ ID NO 79
<211> LENGTH: 11
<212> TYPE: PRT
<213> ORGANISM: Homo sapiens

<400> SEQUENCE: 79

Ile Leu Ala Glu Glu Pro Ile Tyr Ile Arg Val
```

<210> SEQ ID NO 80
<211> LENGTH: 9
<212> TYPE: PRT
<213> ORGANISM: Homo sapiens

<400> SEQUENCE: 80

Phe Leu Leu Glu Arg Glu Gln Leu Leu
1               5

<210> SEQ ID NO 81
<211> LENGTH: 10
<212> TYPE: PRT
<213> ORGANISM: Homo sapiens

<400> SEQUENCE: 81

Leu Leu Leu Pro Leu Glu Leu Ser Leu Ala
1               5                   10

<210> SEQ ID NO 82
<211> LENGTH: 9
<212> TYPE: PRT
<213> ORGANISM: Homo sapiens

<400> SEQUENCE: 82

Ser Leu Ala Glu Thr Ile Phe Ile Val
1               5

<210> SEQ ID NO 83
<211> LENGTH: 11
<212> TYPE: PRT
<213> ORGANISM: Homo sapiens

<400> SEQUENCE: 83

Ala Ile Leu Asn Val Asp Glu Lys Asn Gln Val
1               5                   10

<210> SEQ ID NO 84
<211> LENGTH: 9
<212> TYPE: PRT
<213> ORGANISM: Homo sapiens

<400> SEQUENCE: 84

Arg Leu Phe Glu Glu Val Leu Gly Val
1               5

<210> SEQ ID NO 85
<211> LENGTH: 9
<212> TYPE: PRT
<213> ORGANISM: Homo sapiens

<400> SEQUENCE: 85

Tyr Leu Asp Glu Val Ala Phe Met Leu
1               5

<210> SEQ ID NO 86
<211> LENGTH: 11
<212> TYPE: PRT
<213> ORGANISM: Homo sapiens

<400> SEQUENCE: 86

Lys Leu Ile Asp Glu Asp Glu Pro Leu Phe Leu
1               5                   10

```
<210> SEQ ID NO 87
<211> LENGTH: 9
<212> TYPE: PRT
<213> ORGANISM: Homo sapiens

<400> SEQUENCE: 87

Lys Leu Phe Glu Lys Ser Thr Gly Leu
1               5

<210> SEQ ID NO 88
<211> LENGTH: 11
<212> TYPE: PRT
<213> ORGANISM: Homo sapiens

<400> SEQUENCE: 88

Ser Leu Leu Glu Val Asn Glu Ala Ser Ser Val
1               5                   10

<210> SEQ ID NO 89
<211> LENGTH: 10
<212> TYPE: PRT
<213> ORGANISM: Homo sapiens

<400> SEQUENCE: 89

Gly Val Tyr Asp Gly Arg Glu His Thr Val
1               5                   10

<210> SEQ ID NO 90
<211> LENGTH: 10
<212> TYPE: PRT
<213> ORGANISM: Homo sapiens

<400> SEQUENCE: 90

Gly Leu Tyr Pro Val Thr Leu Val Gly Val
1               5                   10

<210> SEQ ID NO 91
<211> LENGTH: 9
<212> TYPE: PRT
<213> ORGANISM: Homo sapiens

<400> SEQUENCE: 91

Ala Leu Leu Ser Ser Val Ala Glu Ala
1               5

<210> SEQ ID NO 92
<211> LENGTH: 9
<212> TYPE: PRT
<213> ORGANISM: Homo sapiens

<400> SEQUENCE: 92

Thr Leu Leu Glu Gly Ile Ser Arg Ala
1               5

<210> SEQ ID NO 93
<211> LENGTH: 9
<212> TYPE: PRT
<213> ORGANISM: Homo sapiens

<400> SEQUENCE: 93

Ser Leu Ile Glu Glu Ser Glu Glu Leu
1               5

<210> SEQ ID NO 94
```

```
<211> LENGTH: 9
<212> TYPE: PRT
<213> ORGANISM: Homo sapiens

<400> SEQUENCE: 94

Ala Leu Tyr Val Gln Ala Pro Thr Val
1               5

<210> SEQ ID NO 95
<211> LENGTH: 10
<212> TYPE: PRT
<213> ORGANISM: Homo sapiens

<400> SEQUENCE: 95

Lys Leu Ile Tyr Lys Asp Leu Val Ser Val
1               5                   10

<210> SEQ ID NO 96
<211> LENGTH: 9
<212> TYPE: PRT
<213> ORGANISM: Homo sapiens

<400> SEQUENCE: 96

Ile Leu Gln Asp Gly Gln Phe Leu Val
1               5

<210> SEQ ID NO 97
<211> LENGTH: 9
<212> TYPE: PRT
<213> ORGANISM: Homo sapiens

<400> SEQUENCE: 97

Ser Leu Leu Asp Tyr Glu Val Ser Ile
1               5

<210> SEQ ID NO 98
<211> LENGTH: 9
<212> TYPE: PRT
<213> ORGANISM: Homo sapiens

<400> SEQUENCE: 98

Leu Leu Gly Asp Ser Ser Phe Phe Leu
1               5

<210> SEQ ID NO 99
<211> LENGTH: 10
<212> TYPE: PRT
<213> ORGANISM: Homo sapiens

<400> SEQUENCE: 99

Val Ile Phe Glu Gly Glu Pro Met Tyr Leu
1               5                   10

<210> SEQ ID NO 100
<211> LENGTH: 9
<212> TYPE: PRT
<213> ORGANISM: Homo sapiens

<400> SEQUENCE: 100

Ala Leu Ser Tyr Ile Leu Pro Tyr Leu
1               5

<210> SEQ ID NO 101
<211> LENGTH: 9
<212> TYPE: PRT
```

```
<213> ORGANISM: Homo sapiens

<400> SEQUENCE: 101

Phe Leu Phe Val Asp Pro Glu Leu Val
1               5

<210> SEQ ID NO 102
<211> LENGTH: 11
<212> TYPE: PRT
<213> ORGANISM: Homo sapiens

<400> SEQUENCE: 102

Ser Glu Trp Gly Ser Pro His Ala Ala Val Pro
1               5                   10

<210> SEQ ID NO 103
<211> LENGTH: 9
<212> TYPE: PRT
<213> ORGANISM: Homo sapiens

<400> SEQUENCE: 103

Ala Leu Ser Glu Leu Glu Arg Val Leu
1               5

<210> SEQ ID NO 104
<211> LENGTH: 9
<212> TYPE: PRT
<213> ORGANISM: Homo sapiens

<400> SEQUENCE: 104

Ser Leu Phe Glu Ser Leu Glu Tyr Leu
1               5

<210> SEQ ID NO 105
<211> LENGTH: 9
<212> TYPE: PRT
<213> ORGANISM: Homo sapiens

<400> SEQUENCE: 105

Lys Val Leu Glu Tyr Val Ile Lys Val
1               5

<210> SEQ ID NO 106
<211> LENGTH: 10
<212> TYPE: PRT
<213> ORGANISM: Homo sapiens

<400> SEQUENCE: 106

Val Leu Leu Asn Glu Ile Leu Glu Gln Val
1               5                   10

<210> SEQ ID NO 107
<211> LENGTH: 9
<212> TYPE: PRT
<213> ORGANISM: Homo sapiens

<400> SEQUENCE: 107

Ser Leu Leu Asn Gln Pro Lys Ala Val
1               5

<210> SEQ ID NO 108
<211> LENGTH: 9
<212> TYPE: PRT
<213> ORGANISM: Homo sapiens
```

```
<400> SEQUENCE: 108

Lys Met Ser Glu Leu Gln Thr Tyr Val
1               5

<210> SEQ ID NO 109
<211> LENGTH: 11
<212> TYPE: PRT
<213> ORGANISM: Homo sapiens

<400> SEQUENCE: 109

Ala Leu Leu Glu Gln Thr Gly Asp Met Ser Leu
1               5                   10

<210> SEQ ID NO 110
<211> LENGTH: 11
<212> TYPE: PRT
<213> ORGANISM: Homo sapiens

<400> SEQUENCE: 110

Val Ile Ile Lys Gly Leu Glu Glu Ile Thr Val
1               5                   10

<210> SEQ ID NO 111
<211> LENGTH: 9
<212> TYPE: PRT
<213> ORGANISM: Homo sapiens

<400> SEQUENCE: 111

Lys Gln Phe Glu Gly Thr Val Glu Ile
1               5

<210> SEQ ID NO 112
<211> LENGTH: 9
<212> TYPE: PRT
<213> ORGANISM: Homo sapiens

<400> SEQUENCE: 112

Lys Leu Gln Glu Glu Ile Pro Val Leu
1               5

<210> SEQ ID NO 113
<211> LENGTH: 9
<212> TYPE: PRT
<213> ORGANISM: Homo sapiens

<400> SEQUENCE: 113

Gly Leu Ala Glu Phe Gln Glu Asn Val
1               5

<210> SEQ ID NO 114
<211> LENGTH: 9
<212> TYPE: PRT
<213> ORGANISM: Homo sapiens

<400> SEQUENCE: 114

Asn Val Ala Glu Ile Val Ile His Ile
1               5

<210> SEQ ID NO 115
<211> LENGTH: 9
<212> TYPE: PRT
<213> ORGANISM: Homo sapiens

<400> SEQUENCE: 115
```

Ala Leu Ala Gly Ile Val Thr Asn Val
1               5

<210> SEQ ID NO 116
<211> LENGTH: 12
<212> TYPE: PRT
<213> ORGANISM: Homo sapiens

<400> SEQUENCE: 116

Asn Leu Leu Ile Asp Asp Lys Gly Thr Ile Lys Leu
1               5                   10

<210> SEQ ID NO 117
<211> LENGTH: 10
<212> TYPE: PRT
<213> ORGANISM: Homo sapiens

<400> SEQUENCE: 117

Val Leu Met Gln Asp Ser Arg Leu Tyr Leu
1               5                   10

<210> SEQ ID NO 118
<211> LENGTH: 9
<212> TYPE: PRT
<213> ORGANISM: Homo sapiens

<400> SEQUENCE: 118

Lys Val Leu Glu His Val Val Arg Val
1               5

<210> SEQ ID NO 119
<211> LENGTH: 9
<212> TYPE: PRT
<213> ORGANISM: Homo sapiens

<400> SEQUENCE: 119

Leu Leu Trp Gly Asn Leu Pro Glu Ile
1               5

<210> SEQ ID NO 120
<211> LENGTH: 9
<212> TYPE: PRT
<213> ORGANISM: Homo sapiens

<400> SEQUENCE: 120

Ser Leu Met Glu Lys Asn Gln Ser Leu
1               5

<210> SEQ ID NO 121
<211> LENGTH: 9
<212> TYPE: PRT
<213> ORGANISM: Homo sapiens

<400> SEQUENCE: 121

Lys Leu Leu Ala Val Ile His Glu Leu
1               5

<210> SEQ ID NO 122
<211> LENGTH: 10
<212> TYPE: PRT
<213> ORGANISM: Homo sapiens

<400> SEQUENCE: 122

Ala Leu Gly Asp Lys Phe Leu Leu Arg Val
1               5                   10

<210> SEQ ID NO 123
<211> LENGTH: 11
<212> TYPE: PRT
<213> ORGANISM: Homo sapiens

<400> SEQUENCE: 123

Phe Leu Met Lys Asn Ser Asp Leu Tyr Gly Ala
1               5                   10

<210> SEQ ID NO 124
<211> LENGTH: 10
<212> TYPE: PRT
<213> ORGANISM: Homo sapiens

<400> SEQUENCE: 124

Lys Leu Ile Asp His Gln Gly Leu Tyr Leu
1               5                   10

<210> SEQ ID NO 125
<211> LENGTH: 12
<212> TYPE: PRT
<213> ORGANISM: Homo sapiens

<400> SEQUENCE: 125

Gly Pro Gly Ile Phe Pro Pro Pro Pro Gln Pro
1               5                   10

<210> SEQ ID NO 126
<211> LENGTH: 9
<212> TYPE: PRT
<213> ORGANISM: Homo sapiens

<400> SEQUENCE: 126

Ala Leu Asn Glu Ser Leu Val Glu Cys
1               5

<210> SEQ ID NO 127
<211> LENGTH: 9
<212> TYPE: PRT
<213> ORGANISM: Homo sapiens

<400> SEQUENCE: 127

Gly Leu Ala Ala Leu Ala Val His Leu
1               5

<210> SEQ ID NO 128
<211> LENGTH: 9
<212> TYPE: PRT
<213> ORGANISM: Homo sapiens

<400> SEQUENCE: 128

Leu Leu Leu Glu Ala Val Trp His Leu
1               5

<210> SEQ ID NO 129
<211> LENGTH: 9
<212> TYPE: PRT
<213> ORGANISM: Homo sapiens

<400> SEQUENCE: 129

Ser Ile Ile Glu Tyr Leu Pro Thr Leu
1               5

<210> SEQ ID NO 130
<211> LENGTH: 9
<212> TYPE: PRT
<213> ORGANISM: Homo sapiens

<400> SEQUENCE: 130

Thr Leu His Asp Gln Val His Leu Leu
1               5

<210> SEQ ID NO 131
<211> LENGTH: 9
<212> TYPE: PRT
<213> ORGANISM: Homo sapiens

<400> SEQUENCE: 131

Ser Leu Leu Met Trp Ile Thr Gln Cys
1               5

<210> SEQ ID NO 132
<211> LENGTH: 11
<212> TYPE: PRT
<213> ORGANISM: Homo sapiens

<400> SEQUENCE: 132

Phe Leu Leu Asp Lys Pro Gln Asp Leu Ser Ile
1               5                   10

<210> SEQ ID NO 133
<211> LENGTH: 10
<212> TYPE: PRT
<213> ORGANISM: Homo sapiens

<400> SEQUENCE: 133

Tyr Leu Leu Asp Met Pro Leu Trp Tyr Leu
1               5                   10

<210> SEQ ID NO 134
<211> LENGTH: 9
<212> TYPE: PRT
<213> ORGANISM: Homo sapiens

<400> SEQUENCE: 134

Gly Leu Leu Asp Cys Pro Ile Phe Leu
1               5

<210> SEQ ID NO 135
<211> LENGTH: 9
<212> TYPE: PRT
<213> ORGANISM: Homo sapiens

<400> SEQUENCE: 135

Val Leu Ile Glu Tyr Asn Phe Ser Ile
1               5

<210> SEQ ID NO 136
<211> LENGTH: 11
<212> TYPE: PRT
<213> ORGANISM: Homo sapiens

<400> SEQUENCE: 136

Thr Leu Tyr Asn Pro Glu Arg Thr Ile Thr Val
1               5                   10

<210> SEQ ID NO 137
<211> LENGTH: 9

```
<212> TYPE: PRT
<213> ORGANISM: Homo sapiens

<400> SEQUENCE: 137

Ala Val Pro Pro Pro Ser Ser Val
1               5

<210> SEQ ID NO 138
<211> LENGTH: 9
<212> TYPE: PRT
<213> ORGANISM: Homo sapiens

<400> SEQUENCE: 138

Lys Leu Gln Glu Glu Leu Asn Lys Val
1               5

<210> SEQ ID NO 139
<211> LENGTH: 11
<212> TYPE: PRT
<213> ORGANISM: Homo sapiens

<400> SEQUENCE: 139

Lys Leu Met Asp Pro Gly Ser Leu Pro Pro Leu
1               5                   10

<210> SEQ ID NO 140
<211> LENGTH: 9
<212> TYPE: PRT
<213> ORGANISM: Homo sapiens

<400> SEQUENCE: 140

Ala Leu Ile Val Ser Leu Pro Tyr Leu
1               5

<210> SEQ ID NO 141
<211> LENGTH: 9
<212> TYPE: PRT
<213> ORGANISM: Homo sapiens

<400> SEQUENCE: 141

Phe Leu Leu Asp Gly Ser Ala Asn Val
1               5

<210> SEQ ID NO 142
<211> LENGTH: 10
<212> TYPE: PRT
<213> ORGANISM: Homo sapiens

<400> SEQUENCE: 142

Ala Leu Asp Pro Ser Gly Asn Gln Leu Ile
1               5                   10

<210> SEQ ID NO 143
<211> LENGTH: 9
<212> TYPE: PRT
<213> ORGANISM: Homo sapiens

<400> SEQUENCE: 143

Ile Leu Ile Lys His Leu Val Lys Val
1               5

<210> SEQ ID NO 144
<211> LENGTH: 9
<212> TYPE: PRT
<213> ORGANISM: Homo sapiens
```

<400> SEQUENCE: 144

Val Leu Leu Asp Thr Ile Leu Gln Leu
1               5

<210> SEQ ID NO 145
<211> LENGTH: 9
<212> TYPE: PRT
<213> ORGANISM: Homo sapiens

<400> SEQUENCE: 145

His Leu Ile Ala Glu Ile His Thr Ala
1               5

<210> SEQ ID NO 146
<211> LENGTH: 9
<212> TYPE: PRT
<213> ORGANISM: Homo sapiens

<400> SEQUENCE: 146

Ser Met Asn Gly Gly Val Phe Ala Val
1               5

<210> SEQ ID NO 147
<211> LENGTH: 9
<212> TYPE: PRT
<213> ORGANISM: Homo sapiens

<400> SEQUENCE: 147

Met Leu Ala Glu Lys Leu Leu Gln Ala
1               5

<210> SEQ ID NO 148
<211> LENGTH: 9
<212> TYPE: PRT
<213> ORGANISM: Homo sapiens

<400> SEQUENCE: 148

Tyr Met Leu Asp Ile Phe His Glu Val
1               5

<210> SEQ ID NO 149
<211> LENGTH: 11
<212> TYPE: PRT
<213> ORGANISM: Homo sapiens

<400> SEQUENCE: 149

Ala Leu Trp Leu Pro Thr Asp Ser Ala Thr Val
1               5                   10

<210> SEQ ID NO 150
<211> LENGTH: 9
<212> TYPE: PRT
<213> ORGANISM: Homo sapiens

<400> SEQUENCE: 150

Gly Leu Ala Ser Arg Ile Leu Asp Ala
1               5

<210> SEQ ID NO 151
<211> LENGTH: 9
<212> TYPE: PRT
<213> ORGANISM: Homo sapiens

<400> SEQUENCE: 151

```
Ser Tyr Val Lys Val Leu His His Leu
1               5
```

<210> SEQ ID NO 152
<211> LENGTH: 9
<212> TYPE: PRT
<213> ORGANISM: Homo sapiens

<400> SEQUENCE: 152

```
Val Tyr Leu Pro Lys Ile Pro Ser Trp
1               5
```

<210> SEQ ID NO 153
<211> LENGTH: 9
<212> TYPE: PRT
<213> ORGANISM: Homo sapiens

<400> SEQUENCE: 153

```
Asn Tyr Glu Asp His Phe Pro Leu Leu
1               5
```

<210> SEQ ID NO 154
<211> LENGTH: 9
<212> TYPE: PRT
<213> ORGANISM: Homo sapiens

<400> SEQUENCE: 154

```
Val Tyr Ile Ala Glu Leu Glu Lys Ile
1               5
```

<210> SEQ ID NO 155
<211> LENGTH: 12
<212> TYPE: PRT
<213> ORGANISM: Homo sapiens

<400> SEQUENCE: 155

```
Val His Phe Glu Asp Thr Gly Lys Thr Leu Leu Phe
1               5                   10
```

<210> SEQ ID NO 156
<211> LENGTH: 9
<212> TYPE: PRT
<213> ORGANISM: Homo sapiens

<400> SEQUENCE: 156

```
Val Leu Ser Pro Phe Ile Leu Thr Leu
1               5
```

<210> SEQ ID NO 157
<211> LENGTH: 9
<212> TYPE: PRT
<213> ORGANISM: Homo sapiens

<400> SEQUENCE: 157

```
His Leu Leu Glu Gly Ser Val Gly Val
1               5
```

METHOD OF ENHANCING PERSISTENCE OF ADOPTIVELY INFUSED T CELLS

CROSS REFERENCE TO RELATED APPLICATIONS

This application is a continuation of U.S. patent application Ser. No. 16/361,043, filed Mar. 21, 2019, which claims priority to U.S. Provisional application No. 62/646,180, filed on Mar. 21, 2018 and German Patent Application 10 2018 108 612.1, filed on Apr. 11, 2018, the contents of each are hereby incorporated by reference in their entireties.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "3000011-007002_Sequence_Listing_ST25.txt" created on 1 Oct. 2020, and 24,571 bytes in size) is submitted concurrently with the instant application, and the entire contents of the Sequence Listing are incorporated herein by reference.

BACKGROUND

1. Field

The present disclosure provides for methods of improving the efficacy of T cells. In an aspect, the disclosure further provides for methods of enhancing the persistence of T cells for adoptive cell transfer or therapy (ACT). Cytokine sensitivity assays (CSA) and associated methodology capable of predicting the persistence of adoptively infused T Cells are further provided for by way of the instant disclosure. The disclosure also provides for methods of treating cancer in a subject in need thereof as well as T cells populations produced by methods described herein.

2. Background

Adoptive cell transfer or therapy (ACT) is a form of immunotherapy that involves the ex vivo isolation and expansion of antigen-specific T cells for adoptive transfer back to patients. Although a clinical benefit has been obtained in treatment of hematologic malignancies and melanoma, the efficacy of ACT in the treatment of most solid tumors is generally limited because transferred T cells fail to function and persist in vivo. Factors, such as tolerance to tumor-associated antigens (TAAs) and inhibition of tumor-specific T cells due to the suppressive tumor environment, may contribute to this failure. In addition, the necessity for extensive culturing of tumor-specific T cells to obtain sufficient numbers for infusion into patients can greatly influence the quality of the T cells.

T cell persistence is considered to be a driving force for ACT efficacy, correlating T cell persistence/young phenotype to pre-clinical and clinical outcomes. To boost cultured T cells and modulate the phenotype via cytokine-mediated signals, the common-gamma chain (γc)-cytokine IL-2 expands T cells. High doses of IL-2 have also been used to expand ACT T cell cultures. Enforced expression of IL-2 by T cells results in prolonged survival in vitro and maintains the tumor specificity and function. IL-2, however, can promote differentiation of T cells, which may lead to an unfavorable phenotype for ACT usage. To optimize ex vivo T cell cultures for ACT, other γc-cytokines, such as IL-7, IL-15, and IL-21, have been described to play a role in memory T cell formation, proliferation, and survival, yet result in a lower degree of T cell differentiation but are still able to enhance anti-tumor responses.

U.S. Pat. No. 7,993,638 recites methods for treating a subject in need of treatment for cancer, including administering to the subject the activated cytotoxic T lymphocytes (CTLs); administering to the subject at least two cytokines including interferon-α-2b and interleukin-2 (IL-2) that influence CTL persistence.

U.S. 2015/0017120 recites methods of prolonging persistence of transferred cells, stimulating the proliferation of transferred cells, or stimulating a T cell-mediated immune response to a target cell population in a cancer subject receiving adoptive cell therapy (ACT), including: administering an extended-pharmacokinetic IL-2 to a cancer subject receiving ACT, in an amount effective to prolong the persistence of transferred cells in the subject.

There remains a need to improve the outcome of ACT in cancer patients. A solution to this technical problem is provided by the embodiments characterized in the claims.

BRIEF SUMMARY

As described herein, the disclosure provides for methods of improving the efficacy and viability of T cells.

The disclosure further provides for methods for producing T cells with improved efficacy for adoptive immunotherapy comprising
 obtaining T cells from at least one healthy donor, patient, or individual,
 activating the T cells,
 expanding the activated T cells for about 3 days to about 5 days after activation,
 collecting the expanded T cells for infusing into the at least one healthy donor, patient, or individual,
 wherein the efficacy for adoptive immunotherapy of the T cells expanded for about 3 to about 5 days is improved relative to activated T cells expanded for about 7 days or more after activation.

In an aspect, the disclosure provides for methods for increasing the growth of T cells comprising
 obtaining T cells from at least one healthy donor, patient, or individual,
 activating the T cells,
 expanding the activated T cells for about 3 days to about 5 days after activation,
 collecting the expanded T cells for infusing into the at least one healthy donor, patient, or individual,
 wherein the growth of the T cells expanded for about 3 to about 5 days is greater than that of activated T cells expanded for about 7 days or more after activation.

In another aspect, the disclosure provides for methods of decreasing cell death of T cells for use in adoptive immunotherapy comprising
 obtaining T cells from at least one healthy donor, patient, or individual,
 activating the T cells,
 expanding the activated T cells for about 3 days to about 5 days after activation,
 collecting the expanded T cells for infusing into the at least one healthy donor, patient, or individual,
 wherein the cell death of the T cells expanded for about 3 to about 5 days is reduced relative to that of activated T cells expanded for about 7 days or more after activation.

The disclosure further provides for methods wherein the activated T cells are expanded for about 4 days after activation and wherein the efficacy for adoptive immunotherapy of the T cells is greater than that of activated T cells expanded for about 7 days or more after activation.

The disclosure further provides for methods wherein the activated T cells are expanded for about 3 days after activation and wherein the efficacy for adoptive immunotherapy of the T cells is greater than that of activated T cells expanded for about 6 days or more after activation.

The disclosure further provides for methods for producing T cells with improved efficacy for adoptive immunotherapy comprising
obtaining T cells from at least one healthy donor, patient, or individual,
activating the T cells,
transducing the activated T cells with a viral vector,
expanding the transduced T cells for about 3 days to about 5 days after activation,
collecting the expanded transduced T cells for infusing into the at least one healthy donor, patient, or individual,
wherein the efficacy for adoptive immunotherapy of the T cells expanded for about 3 to about 5 days is improved relative to activated and transduced T cells expanded for about 7 days or more after activation.

In an aspect, the disclosure provides for methods for producing T cells with improved efficacy for adoptive immunotherapy comprising
obtaining T cells from at least one healthy donor, patient, or individual,
activating the T cells,
expanding the activated T cells for a first period of time after activation,
collecting the expanded T cells for infusing into the at least one healthy donor, patient, or individual,
wherein the efficacy for adoptive immunotherapy of the T cells expanded for the first period of time is improved relative to activated T cells expanded for a second period of time after activation;
wherein said first period of time is shorter than said second period of time.

In an aspect, the first period of time is from about 2 to about 5 days and said second period of time is from about 6 days to about 10 days; the first period of time is from about 3 to about 5 days and said second period of time is from about 7 days to about 10 days; the first period of time is from about 2 to about 5 days and said second period of time is from about 6 days to about 14 days; and the first period of time is less than about 6 days and said second period of time is greater than about 7 days.

In an aspect, the expanded T cells are CD4+ and/or CD8+ T cells.

In another aspect, the expanded T cells exhibit a naïve T cells ($T_N$) and/or stem memory T cells ($T_{scm}$)/T central memory ($T_{cm}$) phenotype.

According to additional aspects, T cells are activated by a stimulator.

In another aspect, the stimulator comprises anti-CD3 antibody and an anti-CD28 antibody.

In an aspect, T cells described herein are used in adoptive immunotherapy in a patient in need of cancer treatment, wherein the cancer is selected from the group consisting of hepatocellular carcinoma (HCC), colorectal carcinoma (CRC), glioblastoma (GB), gastric cancer (GC), esophageal cancer, non-small cell lung cancer (NSCLC), pancreatic cancer (PC), renal cell carcinoma (RCC), benign prostate hyperplasia (BPH), prostate cancer (PCA), ovarian cancer (OC), melanoma, breast cancer, chronic lymphocytic leukemia (CLL), Merkel cell carcinoma (MCC), small cell lung cancer (SCLC), Non-Hodgkin lymphoma (NHL), acute myeloid leukemia (AML), gallbladder cancer and cholangiocarcinoma (GBC, CCC), urinary bladder cancer (UBC), acute lymphoblastic leukemia (ALL), and uterine cancer (UEC).

In an aspect, the disclosure provides for assays of evaluating T cells viability, comprising
obtaining T cells from at least one donor, patient, or individual,
activating the T cells,
expanding a first portion of the activated T cells over a period of time,
culturing the expanded T cells in the presence of at least one cytokine,
measuring a cytokine response in the cultured T cells,
identifying the period of time that yields a maximum cytokine response, and
expanding a second portion of the activated T cells for the period of time that yields
a maximum cytokine response.

The disclosure further provides for methods of producing T cells comprising obtaining T cells from at least one donor, patient, or individual,
activating the T cells,
expanding a first portion of the activated T cells over time,
culturing the expanded T cells in the presence of at least one cytokine,
measuring a cytokine response in the cultured T cells,
identifying a period of time that yields a maximum cytokine response, and
expanding a second portion of the activated T cells for the period of time that yields a maximum cytokine response.

In an aspect, the T cells are obtained from at least one healthy donor, patient, or individual. In another aspect, the T cells are obtained from at least one cancer-free donor, patient, or individual.

In an aspect, the T cells are allogenic to the patient being treated. In another aspect, the T cells are autologous to the patient being treated.

In an aspect, the disclosure provides for freezing the expanded first portion of the activated T cells prior to culturing.

In another aspect, the disclosure provides for thawing the frozen expanded first portion of activated T cells prior to culturing.

In yet another aspect, the disclosure provides for resting the thawed expanded first portion of the activated T cells prior to culturing.

In another aspect, the disclosure provides for transducing activated T cells with a viral vector or a non-viral vector prior to expanding.

In an aspect described herein, the vector may be a viral vector, such as a retroviral vector expressing a T cell receptor (TCR) or a lentiviral vector expressing a T cell receptor (TCR) or a non-viral vector, such as liposome, expressing a TCR.

In an aspect, T cells expansion is measured over a period of time from about 1 day to about 15 days, from about 2 days to about 14 days, from about 3 days to about 13 days, from about 3 days to about 12 days, from about 3 days to about 11 days, from about 3 days to about 10 days, from about 3 days to about 9 days, from about 3 days to about 8 days, from about 3 days to about 7 days, from about 3 days to about 6 days, from about 3 days to about 5 days, from about 3 days to about 4 days, from about 4 days to about 6 days, or from about 4 days to about 5 days after activation.

In an aspect, the at least one cytokine is selected from the group consisting of (interleukin) IL-2, IL-7, IL-10, IL-12, IL-15, IL-21, and a combination thereof.

In another aspect, the concentration of IL-2 is from about 10 U/ml to about 500 U/ml, from about 10 U/ml to about 450 U/ml, from about 10 U/ml to about 400 U/ml, from about 10 U/ml to about 350 U/ml, from about 10 U/ml to about 300 U/ml, from about 10 U/ml to about 250 U/ml, from about 10 U/ml to about 200 U/ml, from about 10 U/ml to about 150 U/ml, from about 10 U/ml to about 100 U/ml, from about 10 U/ml to about 50 U/ml, from about 20 U/ml to about 40 U/ml, from about 25 U/ml to about 35 U/ml, or from about 30 U/ml to about 35 U/ml.

In another aspect, the concentration of IL-7 provided herein is from 0.1 ng/ml to 50 ng/ml, from 0.1 ng/ml to 45 ng/ml, from 0.1 ng/ml to 40 ng/ml, from 0.1 ng/ml to 35 ng/ml, from 0.1 ng/ml to 30 ng/ml, from 0.1 ng/ml to 25 ng/ml, from 0.1 ng/ml to 20 ng/ml, from 0.1 ng/ml to 15 ng/ml, from 0.1 ng/ml to 10 ng/ml, from 0.1 ng/ml to 5 ng/ml, from 0.1 ng/ml to 4 ng/ml, from 0.1 ng/ml to 3 ng/ml, from 0.1 ng/ml to 2 ng/ml, from 0.1 ng/ml to 1 ng/ml, or from 0.1 ng/ml to 0.5 ng/ml.

In another aspect, the concentration of IL-15 is from 0.1 ng/ml to 50 ng/ml, from 0.1 ng/ml to 45 ng/ml, from 0.1 ng/ml to 40 ng/ml, from 0.1 ng/ml to 35 ng/ml, from 0.1 ng/ml to 30 ng/ml, from 0.1 ng/ml to 25 ng/ml, from 0.1 ng/ml to 20 ng/ml, from 0.1 ng/ml to 15 ng/ml, from 0.1 ng/ml to 10 ng/ml, from 0.1 ng/ml to 5 ng/ml, from 0.1 ng/ml to 4 ng/ml, from 0.1 ng/ml to 3 ng/ml, from 0.1 ng/ml to 2 ng/ml, from 0.1 ng/ml to 1 ng/ml, or from 0.1 ng/ml to 0.5 ng/ml.

The disclosure further provides for methods wherein the cytokine response is selected from one or more of increased proliferation, reduced apoptosis, increased population of naïve T cells ($T_N$) and/or stem memory T cells ($T_{scm}$)/T central memory ($T_{cm}$), and a combination thereof.

In an aspect, the resting step is carried out within a period of time from about 0.5 hour to about 48 hours, about 0.5 hour to about 36 hours, about 0.5 hour to about 24 hours, about 0.5 hour to about 18 hours, about 0.5 hour to about 12 hours, about 0.5 hour to about 6 hours, about 1 hour to about 6 hours, about 2 hours to about 5 hours, about 3 hours to about 5 hours, or about 1 hours to about 24 hours, about 2 to about 24 hours, about 12 to about 48 hours, about 0.5 hour to about 120 hours, about 0.5 hour to about 108 hours, about 0.5 hour to about 96 hours, about 0.5 hour to about 84 hours, about 0.5 hour to about 72 hours, or about 0.5 hour to about 60 hours.

According to the disclosure, in an aspect the anti-CD3 antibody and the anti-CD28 antibody each have a concentration of from about 0.1 µg/ml to about 10.0 µg/ml, about 0.1 µg/ml to about 8.0 µg/ml, about 0.1 µg/ml to about 6.0 µg/ml, about 0.1 µg/ml to about 4.0 µg/ml, about 0.1 µg/ml to about 2.0 µg/ml, about 0.1 µg/ml to about 1.0 µg/ml, about 0.1 µg/ml to about 0.8 µg/ml, about 0.1 µg/ml to about 0.6 µg/ml, about 0.1 µg/ml to about 0.5 µg/ml, about 0.1 µg/ml to about 0.25 µg/ml, about 0.2 µg/ml to about 0.5 µg/ml, about 0.2 µg/ml to about 0.3 µg/ml, about 0.3 µg/ml to about 0.5 µg/ml, about 0.3 µg/ml to about 0.4 µg/ml, or about 0.4 µg/ml to about 0.5 µg/ml.

In another aspect, the activation is carried out within a period of from about 1 hour to about 120 hours, about 1 hour to about 108 hours, about 1 hour to about 96 hours, about 1 hour to about 84 hours, about 1 hour to about 72 hours, about 1 hour to about 60 hours, about 1 hour to about 48 hours, about 1 hour to about 36 hours, about 1 hour to about 24 hours, about 2 hours to about 24 hours, about 4 hours to about 24 hours, about 6 hours to about 24 hours, about 8 hours to about 24 hours, about 10 hours to about 24 hours, about 12 hours to about 24 hours, about 12 hours to about 72 hours, about 24 hours to about 72 hours, about 6 hours to about 48 hours, about 24 hours to about 48 hours, about 6 hours to about 72 hours, or about 1 hours to about 12 hours.

In an aspect, T cells obtained by methods described herein are CD3+ CD8$^+$ T cells.

In an aspect, the disclosure provides for methods of assessing viability of T cells by utilizing methods and method steps described herein. In an aspect, methods described herein only include in vitro method steps. In other aspects, methods described herein do not include in vivo method steps. In yet another aspect, methods described herein include a combination of method steps performed in vitro and in vivo.

In an aspect, methods described herein do not include analysis or evaluation by utilizing transgenic animals, for example, transgenic mice. In yet another aspect, methods described herein are capable of determining conditions for T cells production and/or T cell viability faster than methods involving utilizing a transgenic animal, for example, a transgenic mouse.

In another aspect, methods described herein provide for viable T cells capable of being utilized for infusion into a patient or subject in need thereof. In other aspect, methods described herein are performed in vitro and are predicative of in vivo results. In other aspects, the disclosure provides for high throughput in vitro assays that are predictive of the in vivo viability of T cells for transfusion.

In an aspect, the description provides for cytokine response (CR) assays and associated methodology capable of predicting the persistence of adoptively infused T cells. In an aspect, the description provides for cytokine sensitivity assays that are capable of measuring the effect of in vitro expansion length on ability to respond to cytokine and survive in the absence of continual cytokine stimulation In another aspect, methods described herein may be used to determine which types of T cells persist in vivo by utilizing high-throughput in vitro methodology.

Pharmaceutical compositions comprising T cells produced and described herein are further provided for. In another aspect, pharmaceutical compositions described herein include a pharmaceutically acceptable carrier, excipient, or salt thereof.

T cell population produced by methods described herein are further provided for by way of the disclosure. In an aspect, the T cells are engineered T cells.

In an aspect, the description provides for methods for predicting in vivo persistence of T cells in a solid tumor, comprising thawing cryopreserved T cells expanded for a plurality of expansion times, resting the thawed T cells in the absence of a cytokine, seeding the rested T cells, culturing the seeded T cells for at least one cycle of time, wherein, at the beginning of the at least one cycle of time, one or more cytokines are added to the culture, wherein, at the end of the at least one cycle of time, the added one or more cytokines are depleted, sampling the cultured T cells at a plurality of time points during the at least one cycle of time, measuring a cytokine response of the sampled T cells, identifying an expansion time of the sampled T cells exhibiting a maximum cytokine response from the plurality of expansion times, and formulating the T cells expanded for the identified expansion time into a composition for treating the solid tumor.

In another aspect, the plurality of expansion times are from about 1 day to about 15 days, from about 2 days to about 14 days, from about 3 days to about 13 days, from about 3 days to about 12 days, from about 3 days to about 11 days, from about 3 days to about 10 days, from about 3 days to about 9 days, from about 3 days to about 8 days, from about 3 days to about 7 days, from about 3 days to about 6 days, from about 3 days to about 5 days, from about 3 days to about 4 days, from about 4 days to about 6 days, or from about 4 days to about 5 days after activation.

In another aspect, the one cycle of time is 1-10 days per cycle, 2-10 days per cycle, 3-10 days per cycle, 4-10 days per cycle, 5-10 days per cycle, 6-10 days per cycle, 7-10 days per cycle, 8-10 days per cycle, or 9-10 days per cycle, In another aspect, the at least one cycle of time is 1 cycle of time, 2 cycles of time, 3 cycles of time, 4 cycles of time, 5 cycles of time, 6 cycles of time, 7 cycles of time, 8 cycles of time, 9 cycles of time, or 10 cycles of time.

In another aspect, the solid tumor is selected from the group consisting of hepatocellular carcinoma (HCC), colorectal carcinoma (CRC), glioblastoma (GB), gastric cancer (GC), esophageal cancer, non-small cell lung cancer (NSCLC), pancreatic cancer (PC), renal cell carcinoma (RCC), benign prostate hyperplasia (BPH), prostate cancer (PCA), ovarian cancer (OC), melanoma, breast cancer, Merkel cell carcinoma (MCC), small cell lung cancer (SCLC), gallbladder cancer and cholangiocarcinoma (GBC, CCC), urinary bladder cancer (UBC), and uterine cancer (UEC).

BRIEF DESCRIPTION OF THE DRAWINGS

FIGS. 16A-16C show shortened in vitro expansion of transduced T cells correlates with increased cell division at higher cytokine concentrations.

FIG. 16D shows shortened in vitro expansion of transduced T cells correlates with increased CD25 expression.

FIG. 21A shows cell memory compartments were measured by flow cytometry at day 0 and every 7 days during the 21-day culturing period. $T_{naive/scm}$=CCR7+CD45RO−, $T_{cm}$=CCR7+CD45RO+, $T_{cm}$=CCR7−CD45RO+, and $T_{eff}$=CCR7−CD45RO−.

FIG. 21B shows input cells were labeled with PkH proliferation dye at culture initiation and the proliferation of distinct memory compartment were measured based on PkH dilution by day 7 in culture period.

FIG. 28 shows Kyoto Encyclopedia of Genes and Genomes (KEGG) pathway analysis during T-cell manufacturing. The left panels show the pathways that are upregulated between the samples. The right panels show the pathways are that are downregulated between the samples. For each up or down regulation, the later time point is referenced (i.e., day_7 vs day_4_down indicates pathways that were down regulated in the day 7 sample vs the day 4 sample).

DETAILED DESCRIPTION

Figure 1:
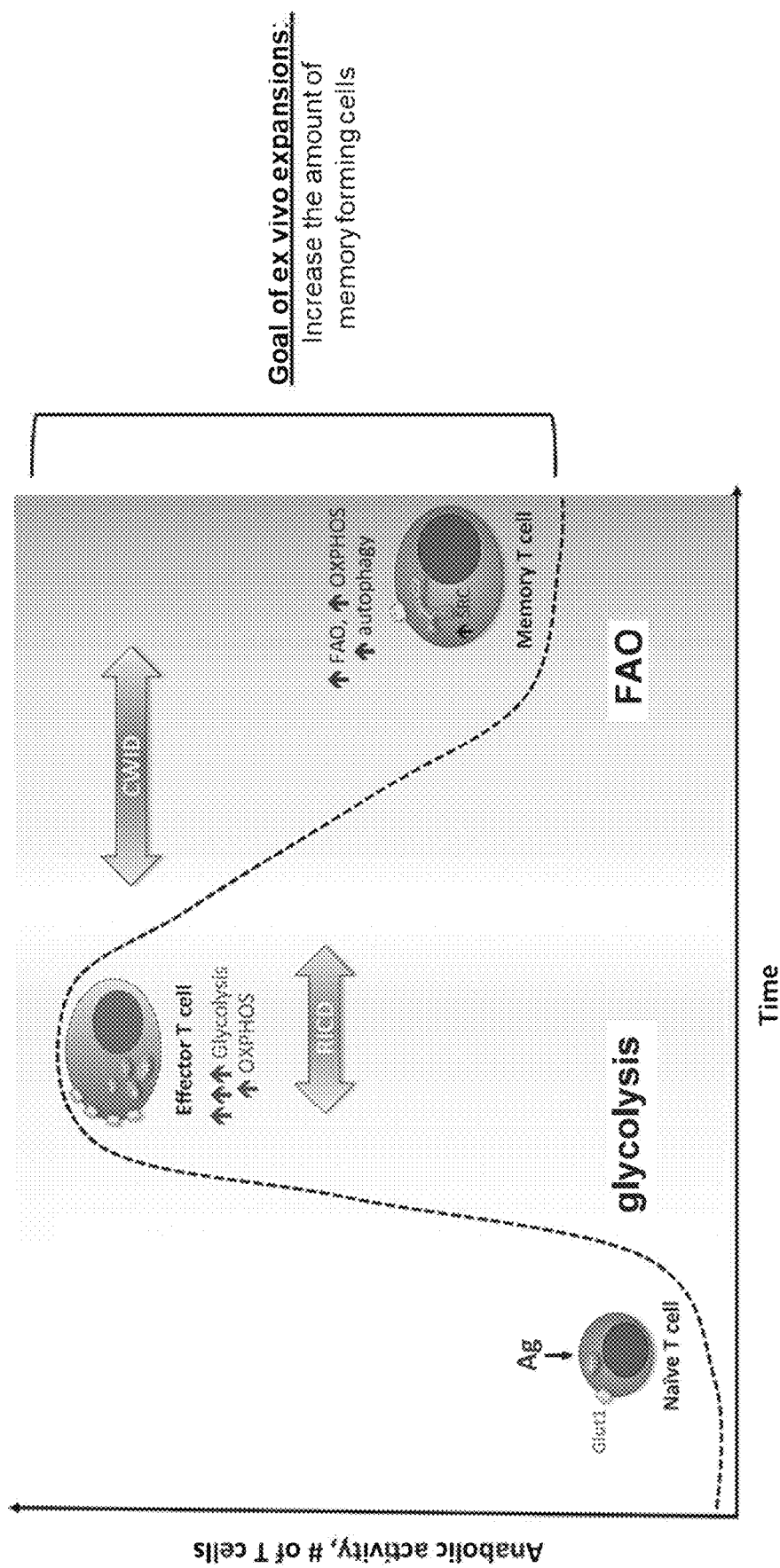
FIG. 1 shows T cell apoptosis (e.g., re-stimulation induced cell death (RICD) and cytokine withdrawal induced cell death (CWID) and memory formation. (Voss et al., *Cancer Letters* 408 (2017) 190-196, the content of which is hereby incorporated by reference in its entirety).

As described herein, the disclosure provides for methods of improving the efficacy and viability of T cells.

In an aspect described herein, minimally expanded engineered T cells demonstrate greater clinical efficacy as compared to T cells expanded for extended in vitro periods due to an increased naivety and ability to proliferate and persist in-vivo. In an aspect, the minimally expanded engineered T cells are expanded for about 3 to about 5 days relative to extended expression of about 7 to about 10 days.

In an aspect described herein, T cells with a shorter expansion time of about 3 to about 5 days exhibit an increased cytokine response by 1) proliferation, 2) reduced apoptosis, and 3) persistence over T cells produced by the same method but with an increased expansion time of about 7 to about 10 days.

In an aspect, adoptive cell transfer or therapy (ACT) comprises a treatment method, in which cells are removed from a donor, cultured and/or manipulated in vitro, and administered to a patient for the treatment of a disease. In some embodiments, transferred cells may be autologous cells, meaning that the patient acts as his or her own donor. In some embodiments, transferred cells may be lymphocytes, e.g., T cells. In some embodiments, transferred cells may be genetically engineered prior to administration to a patient. For example, the transferred cells can be engineered to express a T cell receptor (TCR) having specificity for an antigen of interest. In one embodiment, transferred cells may be engineered to express a chimeric antigen receptor (CAR). In certain embodiments, transferred cells may be engineered (e.g., by transfection or conjugation) to express a molecule that enhances the anti-tumor activity of the cells, such as a cytokine (IL-2, IL-12), an anti-apoptotic molecule (BCL-2, BCL-X), or a chemokine (CXCR2, CCR4, CCR2B). In certain embodiments, transferred cells may be engineered to express both a CAR and a molecule that enhances anti-tumor activity or persistence of cells.

In an aspect, the disclosure relates to methods wherein the outcome of Adoptive cell transfer or therapy (ACT) can be improved by administering minimally expanded T cells to cancer subjects.

Methods of Treatment

In an aspect, expanded engineered T cells described herein are useful for treating a disorder associated with abnormal apoptosis or a differentiative process (e.g., cellular proliferative disorders or cellular differentiative disorders, such as cancer). Non-limiting examples of cancers that may be amenable to treatment with the methods of the present invention are described below.

Examples of cellular proliferative and/or differentiative disorders may include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. Accordingly, the compositions of the present disclosure (e.g., minimally ex vivo expanded engineered T cells) can be administered to a patient who has cancer.

As used herein, the terms "cancer" (or "cancerous"), "hyperproliferative," and "neoplastic" may be used to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells may occur in disease states characterized by malignant tumor growth. Examples of non-pathologic hyperproliferative cells may include proliferation of cells associated with wound repair.

The term "cancer" or "neoplasm" may be used to refer to malignancies of the various organ systems, including those affecting the lung, breast, thyroid, lymph glands and lymphoid tissue, gastrointestinal organs, and the genitourinary tract, as well as to adenocarcinomas, which may be generally considered to include malignancies, such as most colon cancers, renal cell carcinoma, prostate cancer and/or testicular tumors, non-small cell carcinoma of the lung, cancer of the small intestine and cancer of the esophagus. With respect to the methods of the invention, the cancer can be any cancer, including any of acute lymphocytic cancer, acute myeloid leukemia, alveolar rhabdomyo sarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the vulva, chronic lymphocytic leukemia, chronic myeloid cancer, cervical cancer, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, peritoneum, omentum, and mesentery cancer, pharynx cancer, prostate cancer, rectal cancer, renal cancer, skin cancer, soft tissue cancer, testicular cancer, thyroid cancer, ureter cancer, urinary bladder cancer, and digestive tract cancer such as, e.g., esophageal cancer, gastric cancer, pancreatic cancer, stomach cancer, small intestine cancer, gastrointestinal carcinoid tumor, cancer of the oral cavity, colon cancer, and hepatobiliary cancer.

The term "carcinoma" refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term may also include carcinosarcomas, which include malignant tumors composed of carcinomatous and sarcomatous tissues. An "adenocarcinoma" refers to a carcinoma derived from glandular tissue or in which the tumor cells form recognizable glandular structures.

Additional examples of proliferative disorders may include hematopoietic neoplastic disorders. As used herein, the term "hematopoietic neoplastic disorders" may include diseases involving hyperplastic/neoplastic cells of hematopoietic origin, e.g., arising from myeloid, lymphoid or erythroid lineages, or precursor cells thereof. Preferably, the diseases may arise from poorly differentiated acute leukemias (e.g., erythroblastic leukemia and acute megakaryoblastic leukemia). Additional exemplary myeloid disorders may include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas may include but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

It will be appreciated by those skilled in the art that amounts for minimally expanded engineered T cells sufficient to reduce tumor growth and size, or a therapeutically effective amount, may vary not only on the particular compositions selected, but also with the route of administration, the nature of the condition being treated, and the age and condition of the patient, and will ultimately be at the discretion of the patient's physician or pharmacist. The length of time during which minimally expanded engineered T cells used in the instant methods may be given varies on an individual basis. It will be appreciated by those skilled in the art that reference herein to treatment extends to prophylaxis as well as the treatment of the noted cancers and symptoms.

The terms "T cell" or "T lymphocyte" may include thymocytes, naïve T lymphocytes, immature T lymphocytes, mature T lymphocytes, resting T lymphocytes, or activated T lymphocytes. Illustrative populations of T cells suitable for use in particular embodiments include, but are not limited to, helper T cells (HTL; CD4+ T cell), a cytotoxic T cell (CTL; CD8+ T cell), CD4+CD8+ T cell, CD4−CD8− T cell, or any other subset of T cells. Other illustrative populations of T cells suitable for use in particular embodiments include, but are not limited to, T cells expressing one or more of the following markers: CD3, CD4, CD8, CD27, CD28, CD45RA, CD45RO, CD62L, CD127, CD197, and HLA-DR and if desired, can be further isolated by positive or negative selection techniques.

A peripheral blood mononuclear cell (PBMC) refers to any blood cell with a round nucleus (i.e., a lymphocyte, a monocyte, or a macrophage). These blood cells are a critical component in the immune system to fight infection and adapt to intruders. The lymphocyte population consists of CD4+ and CD8+ T cells, B cells and Natural Killer cells, CD14+ monocytes, and basophils/neutrophils/eosinophils/dendritic cells. These cells are often separated from whole blood or from leukopacks using FICOLL™, a hydrophilic polysaccharide that separates layers of blood, with monocytes and lymphocytes forming a buffy coat under a layer of plasma. In one embodiment, "PBMCs" refers to a population of cells comprising at least T cells, and optionally NK cells, and antigen presenting cells.

The term "activation" refers to the state of a T cell that has been sufficiently stimulated to induce detectable cellular proliferation. In particular embodiments, activation can also be associated with induced cytokine production, and detectable effector functions. The term "activated T cells" refers to, among other things, T cells that are proliferating. Signals generated through the TCR alone are insufficient for full activation of the T cell and one or more secondary or costimulatory signals are also required. Thus, T cell activation comprises a primary stimulation signal through the TCR/CD3 complex and one or more secondary costimulatory signals. Costimulation can be evidenced by proliferation and/or cytokine production by T cells that have received a primary activation signal, such as stimulation through the CD3/TCR complex or through CD2.

As used herein, a resting T cell means a T cell that is not dividing or producing cytokines. Resting T cells are small (approximately 6-8 microns) in size compared to activated T cells (approximately 12-15 microns).

As used herein, a primed T cell is a resting T cell that has been previously activated at least once and has been removed from the activation stimulus for at least about 1 hour, at least about 2 hours, at least about 3 hours, at least about 4 hours, at least about 5 hours, at least about 6 hours, at least about 12 hours, at least about 24 hours, at least about 48 hours, at least about 60 hours, at least about 72 hours, at least about 84 hours, at least about 96 hours, at least about 108 hours, or at least about 120 hours. Alternatively, resting may be carried out within a period of from about 0.5 hour to about 120 hours, about 0.5 hour to about 108 hours, about 0.5 hour to about 96 hours, about 0.5 hour to about 84 hours, about 0.5 hour to about 72 hours, about 0.5 hour to about 60 hours, about 0.5 hour to about 48 hours, about 0.5 hour to about 36 hours, about 0.5 hour to about 24 hours, about 0.5 hour to about 18 hours, about 0.5 hour to about 12 hours, about 0.5 hour to about 6 hours, about 1 hour to about 6 hours, about 2 hours to about 5 hours, about 3 hours to about 5 hours, or about 4 hours to about 5 hours. Primed T cells usually have a memory phenotype.

Embodiments of the present disclosure may include resting in the absence of cytokines or in the presence of cytokines, e.g., IL-2, IL-7, IL-10, IL-12, IL-15, IL-21, or a combination thereof, such as IL-7+IL-15, for from about 0.5 hour to about 48 hours, about 0.5 hour to about 36 hours, about 0.5 hour to about 24 hours, about 0.5 hour to about 18 hours, about 0.5 hour to about 12 hours, about 0.5 hour to about 6 hours, about 1 hour to about 6 hours, about 2 hours to about 5 hours, about 3 hours to about 5 hours, about 4 hours to 6 hours, about 1 hours to about 24 hours, about 2 to about 24 hours, about 12 to about 48 hours, about 0.5 hour to about 120 hours, about 0.5 hour to about 108 hours, about 0.5 hour to about 96 hours, about 0.5 hour to about 84 hours, about 0.5 hour to about 72 hours, or about 0.5 hour to about 60 hours, e.g., about 4 to about 6 hours.

Controlled expansion and contraction of lymphocytes both during and after an adaptive immune response may be imperative to sustaining a healthy immune system. Both extrinsic and intrinsic pathways of lymphocyte apoptosis may be programmed to eliminate cells at the proper time to ensure immune homeostasis. Without this lymphocyte apoptosis barrier, prolonged persistence and/or unchecked accumulation of activated lymphocytes can result in immunopathology, autoimmunity, and lymphoid cancers.

FIG. 1 shows, like most somatic cells, naïve and memory T cells may operate in a generally quiescent metabolic state and utilize mitochondrial oxidative phosphorylation (OXPHOS) for ATP generation. Following T cell receptor (TCR) stimulation, however, responding T cells rapidly switch to using glycolysis even in the presence of oxygen (Warburg effect). Activated T cells may proliferate and acquire potent effector functions (e.g. IFN-γ production), which may be linked to glycolytic metabolism. These changes in cellular metabolism over the course of a T cell response may profoundly influence cell survival and differentiation, including the generation of memory. During this window of expansion and aerobic glycolysis, however, effector T cells may become sensitive to restimulation-induced cell death (RICD).

Restimulation induced cell death (RICD) is an apoptotic program that may ultimately set an upper limit for effector T cell expansion during an infection. RICD sensitivity may be dependent on prior activation, cell cycle induction via cytokines, such as IL-2, and a subsequent, strong restimulation signal propagated through the TCR, which induces apoptosis in a subset of effectors. Unlike effector T cells, naive and resting memory T cells may be relatively resistant to RICD. By constraining effector T cell numbers during the antigen-induced expansion phase, this self-regulatory death pathway may help maintain immune homeostasis by precluding excessive, non-specific immunopathological damage to the host. Indeed, a defect in RICD contributes to excessive T cell accumulation and lethal damage to host tissues, as noted in patients with X-linked lymphoproliferative disorder.

Cytokine withdrawal-induced cell death (CWID) is an apoptosis program responsible for culling the majority of effector T cells, triggered by waning cytokines, e.g., IL-2, levels after an infection is cleared and may save a select few that survive as memory T cells. While excessive anabolic metabolism (e.g., glycolysis) may leave effector T cells more susceptible to RICD, catabolic metabolism (e.g., autophagy and fatty acid oxidation (FAO)), on the other hand, can protect T cells derived from distinct memory compartments from death induced by cytokine withdrawal. CWID sensitivity, therefore, may play a major role in determining which and how many T cells survive contraction and enter the memory pool, influencing secondary responses derived from distinct memory subsets.

CWID and RICD may operate at different phases of the immune response as hard-wired feedback response programs, influenced by the dynamic localization of cells, antigen, and cytokine. Both processes are exquisitely regulated by the availability of antigen and IL-2 as well as other growth/survival cytokines. Mechanistically, these two processes may eliminate T cells through distinct biochemical mechanisms of apoptosis, known as the intrinsic and extrinsic pathways. The intrinsic pathway is controlled by relative expression of Bcl-2 family proteins that regulate mitochondrial outer membrane potential (MOMP). When mitochondria are depolarized, cytochrome c release catalyzes the cleavage and activation of procaspase 9. Extrinsic apoptosis is signaled principally through death receptors (DRs) of the tumor necrosis factor receptor (TNFR) superfamily, such as Fas.

CWID induces intrinsic apoptosis. Withdrawal of IL-2 or other γ-chain cytokines specifically upregulates and activates Bim, a key pro-apoptotic protein that antagonizes the function of anti-apoptotic Bcl-2 family proteins (e.g. Bcl-2, Bcl-xL, and Mcl-1) and activates Bax, which causes mitochondrial permeabilization. RICD may be attributed to an extrinsic apoptosis signal through Fas, which may be stimulated in cis or in trans by membrane-anchored FasL exposed on the surface of restimulated T cells.

Because catabolic metabolism (i.e. autophagy) can protect T cells derived from distinct memory compartments from death induced by cytokine withdrawal, i.e., CWID, one objective of ex vivo T cell expansion may be to increase the amount of memory forming cells, such as naive T cells ($T_N$) and/or stem memory T cells ($T_{scm}$)/T central memory ($T_{cm}$).

Figure 2:
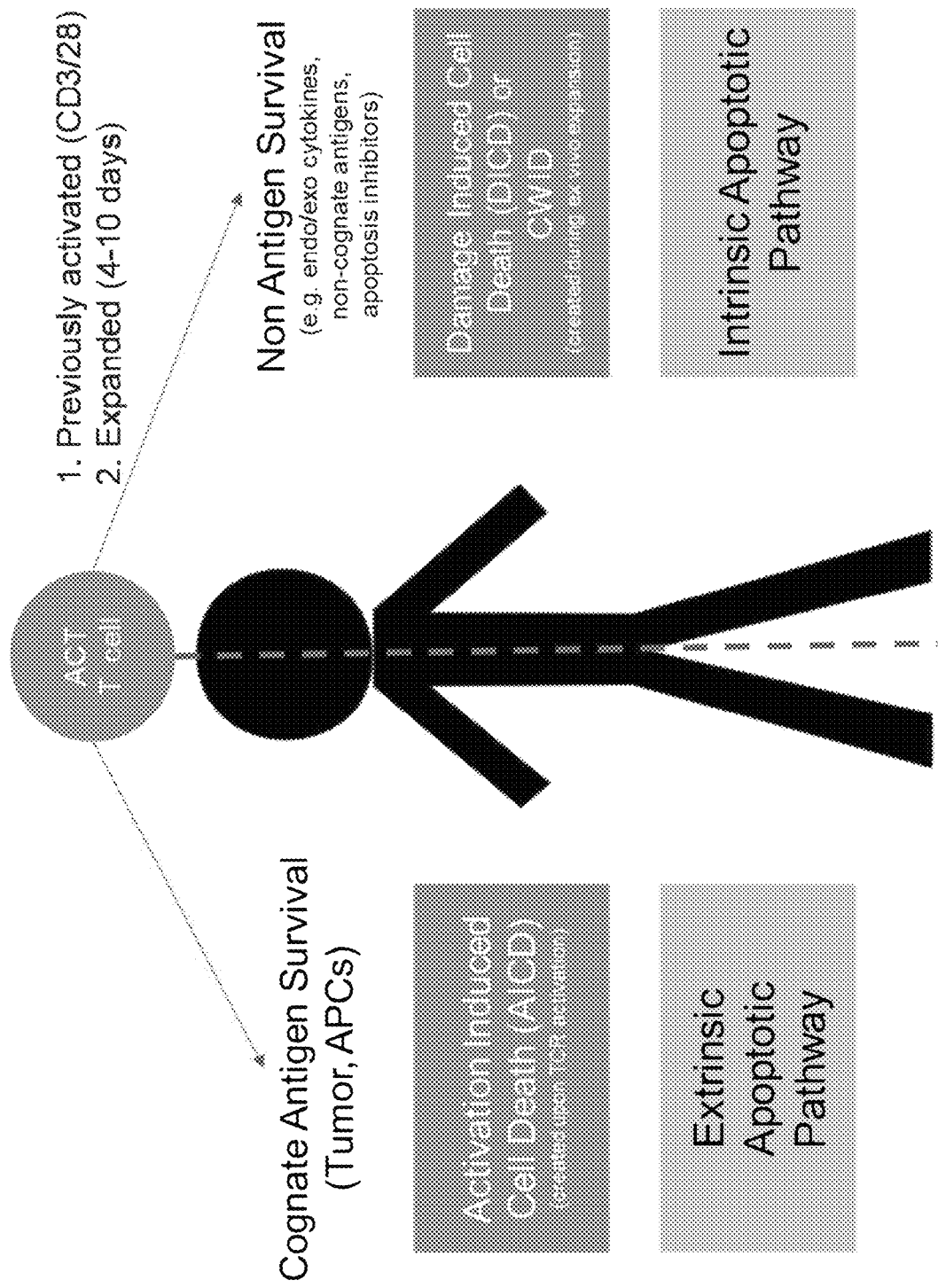
FIG. 2 shows model of in vivo T cell survival in ACT targeting liquid tumors and solid tumors by inhibiting intrinsic or extrinsic apoptotic pathway, respectively.

FIG. 2 shows differences of conventional ACT T cells for treating solid tumors and liquid tumors. For treating solid tumors, T cells may be activated by anti-CD3 and anti-CD28 antibodies, followed by expansion for a period of time. Activated/expanded engineered T cells in a solid tumor environment with reduced access of cognate antigen compared to liquid tumors, non-cognate antigens, and limited apoptosis inhibitors, may undergo intrinsic apoptotic pathways, e.g., damage induced cell death (DICD) or CWID, induced during ex vivo expansion. For treating liquid tumors, activated/expanded engineered T cells in liquid tumor environment with cognate antigen-rich environment with tumors and antigen presenting cells, may be less likely to undergo apoptosis from CWID, but may be more likely to undergo activation induced cell death (AICD) from increase antigen stimulation, indicating that treatment of solid tumors may require T cells to withstand CWID more than AICD.

Figure 3:
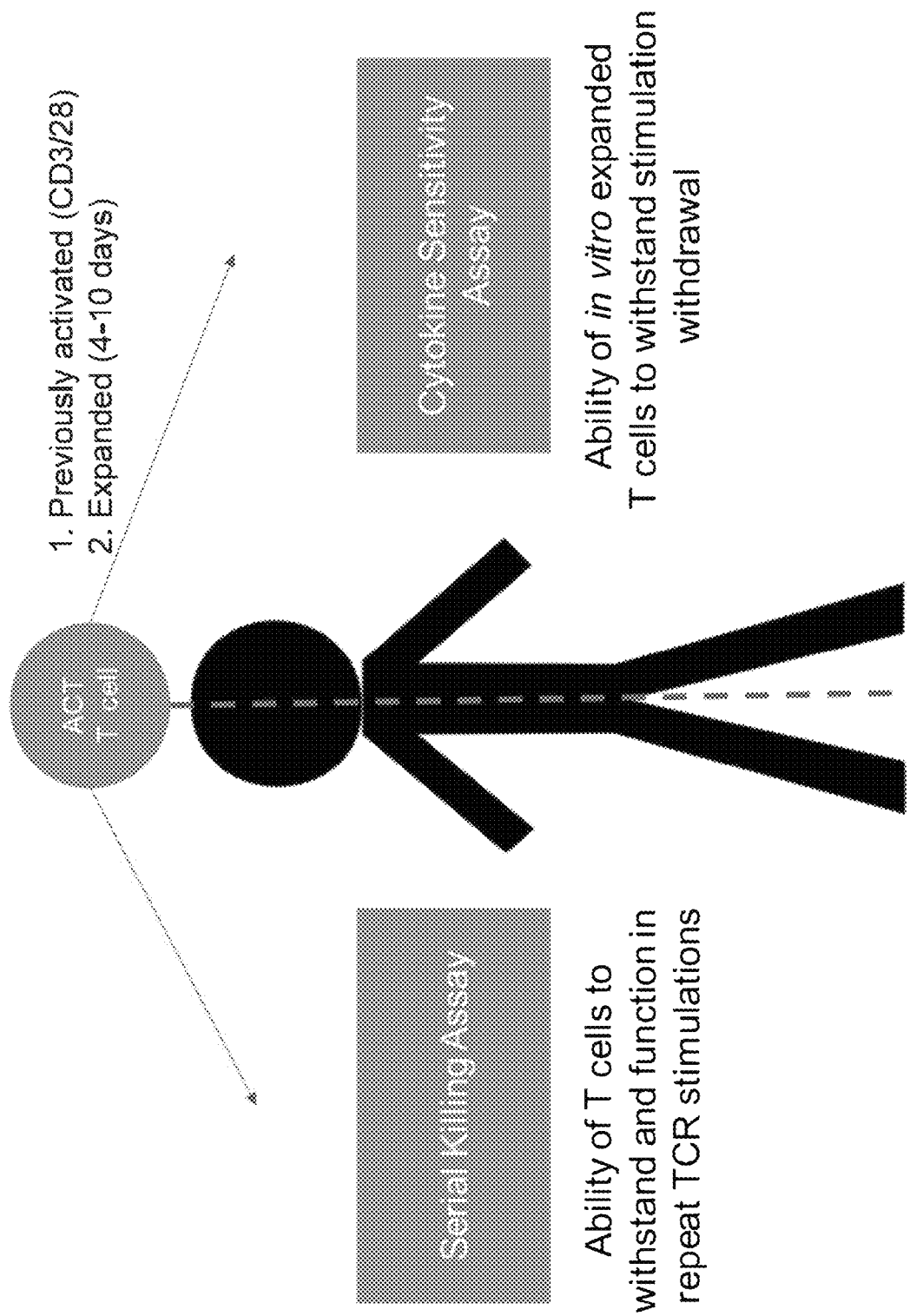
FIG. 3 shows model of testing in vivo T cell survival in ACT targeting liquid tumors and solid tumors by serial killing assay or cytokine sensitivity assay, respectively.

FIG. 3 shows, to test the ability of in vitro expanded T cells to survive cytokine stimulation withdrawal, e.g., in solid tumors, cytokine sensitivity assays may be used. On the other hand, to test the ability of in vitro expanded T cells to survive and function in repeated TCR stimulations, e.g., in liquid tumors, serial killing assays may be used.

Table 1 summarize differences of T cell survival in vivo between liquid tumors and solid tumors.

TABLE 1

Model of in vivo T cell survival

| Liquid Tumors | Solid Tumors |
| --- | --- |
| TCR Stimulation in Periphery | TCR Stimulation Localized to Tumor Site and Antigen Presenting Cells (APCs) |
| High Tumor Burden in Lymphocytic Rich Compartments | Low Tumor Burden in Lymphocytic Rich Compartments |
| Less Dependent on Cytokines for Survival (IL-7 and IL-15) | More Dependent on Cytokines for Survival (IL-7 and IL-15) |

Because in vitro expanded T cells in ACT targeting solid tumors in antigen deprived environments may be more dependent on cytokines for survival than those targeting liquid tumors, in vitro memory formation and CWID reduction may be more critical for in vitro expanded T cells targeting solid tumors than those targeting liquid tumors. Therefore, selecting T cell types that could persist in vivo in a high-throughput patient specific fashion for ACT may increase clinical efficacy of targeting solid tumors. Cytokine sensitivity assays of the present disclosure may be used to predict and select which types of expanded T cells that could persist in vivo in antigen deprived environments.

Sources of T Cells

Prior to expansion and genetic modification of T cells, a source of T cells may be obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments, any number of T cell lines available in the art may be used. In certain embodiments, T cells can be obtained from a unit of blood collected from a subject using any number of techniques known to the skilled artisan, such as Ficoll™ separation. In one preferred embodiment, cells from the circulating blood of an individual may be obtained by apheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media for subsequent processing steps. The cells may be washed with phosphate buffered saline (PBS), or with a wash solution that lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, $Ca^{3+}$-free, $Mg^{2+}$-free PBS, PlasmaLyte A, or other saline solution with or without buffer. Alternatively, the undesirable components of the apheresis sample may be removed, and the cells directly resuspended in culture media.

In another embodiment, T cells may be isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+T cells, can be further isolated by positive or negative selection techniques. For example, in one embodiment, T cells may be isolated by incubation with anti-CD3/anti-CD28 (i.e., 3×28)-conjugated beads, such as DYNABEADS® M-450 CD3/CD28 T, for a time period sufficient for positive selection of the desired T cells.

Enrichment of a T cell population by negative selection can be accomplished with a combination of antibodies directed to surface markers unique to the negatively selected cells. One method may be cell sorting and/or selection via negative magnetic immune-adherence or flow cytometry that uses a cocktail of monoclonal antibodies directed to cell surface markers present on the cells negatively selected. For example, to enrich for CD4+ cells by negative selection, a monoclonal antibody cocktail typically may include antibodies to CD14, CD20, CD11 b, CD16, HLA-DR, and CD8. In certain embodiments, it may be desirable to enrich for or positively select for regulatory T cells, which typically may express CD4+, CD25+, CD62L1, GITR+, and FoxP3+. Alternatively, in certain embodiments, T regulatory cells may be depleted by anti-CD25 conjugated beads or other similar method of selection.

For isolation of a desired population of cells by positive or negative selection, the concentration of cells and surface (e.g., particles, such as beads) can be varied. In certain embodiments, it may be desirable to significantly decrease the volume, in which beads and cells may be mixed together (i.e., increase the concentration of cells), to ensure maximum contact of cells and beads. For example, in one embodiment, a concentration of 2 billion cells/ml may be used. In one embodiment, a concentration of 1 billion cells/ml may be used. In a further embodiment, greater than 100 million cells/ml may be used. In a further embodiment, a concentration of cells of 10, 15, 20, 25, 30, 35, 40, 45, or 50 million cells/ml may be used. In yet another embodiment, a concentration of cells from 75, 80, 85, 90, 95, or 100 million cells/ml may be used. In further embodiments, concentrations of 125 or 150 million cells/ml can be used. Using high concentrations can result in increased cell yield, cell activation, and cell expansion. Further, use of high cell concentrations may allow more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells may allow more efficient selection of CD8+ T cells that normally have weaker CD28 expression. In a related embodiment, it may be desirable to use lower concentrations of cells. By significantly diluting the mixture of T cells and surface (e.g., particles such as beads), interactions between the particles and cells may be minimized. This may select for cells that express high amounts of desired antigens to be bound to the particles.

Whether prior to or after genetic modification of the T cells, the cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No.

2006/0121005. The content of each of these patents and applications is herein incorporated by reference in their entireties. Additional strategies for expanding the population of T cells are described in, e.g., Dudley et al. *Journal of Immunotherapy* 2003; 26:332-42; Rasmussen et al., *Journal of Immunological Methods* 2010; 355:52-60; and Somerville et al., *Journal of Translational Medicine* 2012; 10:69. The entire contents of the foregoing references are incorporated herein by reference in their entireties.

Administration of Autologous Cells

The autologous cells can be administered by any suitable route as known in the art. Preferably, the cells may be administered as an intra-arterial or intravenous infusion, which lasts about 30 to about 60 minutes. Other exemplary routes of administration may include intraperitoneal, intrathecal and intralymphatic.

Likewise, any suitable dose of autologous cells can be administered. For example, in one embodiment, from about $1.0 \times 10^8$ cells to about $1.0 \times 10^{12}$ cells may be administered. In one embodiment, from about $1.0 \times 10^{10}$ cells to about $13.7 \times 10^{10}$ T-cells may be administered, with an average of around $5.0 \times 10^{10}$ T-cells. Alternatively, in another embodiment, from about $1.2 \times 10^{10}$ to about $4.3 \times 10^{10}$ T-cells may be administered.

In one embodiment, the autologous cells used for ACT may be lymphocytes, e.g., T cells. In one embodiment, the T cells may be "young" T cells, e.g., between 19-35 days old, as described in, for example, U.S. Pat. No. 8,383,099, incorporated by reference herein in its entirety. Young T cells are believed to have longer telomeres than older T cells, and longer telomere length may be associated with improved clinical outcome following ACT in some instances.

In an aspect, the T cells and methods of producing T cells described herein may be used in conjunction with one or more of representative strategies for ACT: tumor infiltrating lymphocytes (TIL), antigen-expanded CD8+ and/or CD4+ T cells, T cells genetically modified to express a T cell receptor (TCR) that specifically recognizes a tumor antigen, and T cells genetically modified to express a chimeric antigen receptor (CAR). A brief and non-limiting description of each of these approaches is set forth below.

Tumor Infiltrating Lymphocytes (TIL)

One ACT strategy involves the transplantation of autologous TIL expanded ex vivo from tumor fragments or single cell enzymatic digests of tumor metastases. T cell infiltrates in tumors are polyclonal in nature and collectively recognize multiple tumor antigens. See, for example, Rosenberg et al., *N. Engl. J. Med.* (1988) 319:1676-1680, which is herein incorporated by reference in its entirety.

In an exemplary TIL ACT protocol, tumors may be resected from patients and cut into small (for example, 3-5 mm²) fragments under sterile conditions. The fragments may be placed into culture plates or flasks with growth medium and treated with high-dose IL-2. This initial TIL expansion-phase (also known as the "Pre-REP" phase) typically lasts about 3 to about 5 weeks, during which time about $5 \times 10^7$ or more TILs may be produced. The resulting TILs may be then further expanded (e.g., following a rapid expansion protocol (REP)) to produce TILs suitable for infusion into a subject. The pre-REP TILs can be cryopreserved for later expansion, or they may be expanded immediately. Pre-REP TILs can also be screened to identify cultures with high anti-tumor reactivity prior to expansion. A typical REP may involve activating TILs using a T-cell stimulating antibody, e.g., an anti-CD3 mAb, in the presence of irradiated PBMC feeder cells. The feeder cells can be obtained from the patient or from healthy donor subjects. IL-2 may be added to the REP culture at concentrations of about 6,000 U/mL to promote rapid TIL cell division. Expansion of TILs in this manner can take about 2 weeks or longer, and results in a pool of about 10-150 billion TILs. The expanded cells may be washed and pooled, and may be suitable for infusion into a patient. Patients may typically receive 1 or 2 infusions (separated by 1-2 weeks) of $10^9$-$10^{11}$ cells. Patients have been administered high-dose IL-2 therapy (e.g., $7.2 \times 10^5$ IU/kg every 8 hours for about 2 to about 3 days) to help support the TIL cells after infusion. See, for example, Rosenberg et al., *Nat. Rev. Cancer* (2008) 8:299-308, which is herein incorporated by reference in its entirety. Before infusion, a patient can optionally be lymphodepleted using cyclophosphamide (Cy) and fludaribine (Flu). See, for example, Dudley et al., *Science* (2003) 298:850-854, which is herein incorporated by reference in its entirety. In addition, to prevent the re-emergence of endogenous regulatory T cells (Tregs), total body irradiation (TBI) has been used with lymphodepletion, See, for example, Dudley et al., *J. Clin. Oncol.* (2008) 26(32):5233-5239, which is herein incorporated by reference in its entirety.

Infusion of minimally expanded TIL to subjects receiving an ACT regimen may promote the persistence of the transferred cells, stimulate the persistence, proliferation and survival of transferred cells, and improve tumor regression.

Antigen-Expanded CD8+ and/or CD4+ T Cells

Autologous peripheral blood mononuclear cells (PBMC) can be stimulated in vitro with antigen to generate tumor antigen-specific or polyclonal CD8+ and/or CD4+ T cell clones that can be used for ACT. See, for example, Mackensen et al., *J. Clin. Oncol.* (2006) 24(31):5060-5069; Mitchell et al., *J. Clin. Oncol.* (2002) 20(4):1075-1086; Yee et al., *Proc. Natl. Aad. Sci. USA* (2002) 99(25):16168-16173; Hunder et al., *N. Engl. J. Med.* (2008) 358(25):2698-2703; Verdegaal et al., *Cancer Immunol. Immunother.* (2001) 60(7):953-963, the contents of each which is herein incorporated by reference. To avoid the time-consuming and labor-intensive process of expanding tumor-specific T cells from naïve PBMC populations, an approach has been recently described, in which antigen-specific T cells for ACT may be generated using multiple stimulation of autologous PBMC using artificial antigen-presenting cells (aAPC) expressing HLA-A0201, costimulatory molecules, and membrane-bound cytokines. See, for example, Suhoski et al., *Mol. Ther.* (2007) 15(5):981-988; Butler et al., *Sci. Transl. Med.* (2011) 3(80):80ra34, which is herein incorporated by reference in its entirety.

In one embodiment, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, in the presence of a T cell growth factor, such as 300 IU/ml IL-2 or IL-15, with IL-2 being preferred. The in vitro-induced T-cells may be rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example.

In one embodiment, cell population may be enriched for CD8+ T cells. A T cell culture may be depleted of CD4+ cells and enriched for CD8+ cells using, for example, a CD8 microbead separation (e.g., using a Clini-MACSplus CD8 microbead system (Miltenyi Biotec™). Enriching for CD8+ T cells may improve the outcome of ACT by removing CD4+ T regulatory cells.

Infusion of minimally expanded T cells, e.g., CD8+ and/or CD4+ T cells obtained from stimulation of PBMCs, to subjects receiving an ACT regimen may promote the persistence of the transferred cells, stimulate the persistence, proliferation and survival of transferred cells, and improve tumor regression.

T Cells Genetically Modified to Express a T Cell Receptor (TCR) that Specifically Recognizes a Tumor Antigen In some instances, it may not be possible to obtain TILs with high avidity for tumor antigens in the quantity necessary for ACT. Accordingly, it may be desirable to genetically modify lymphocytes to obtain a cell population that may specifically recognize an antigen of interest prior to infusion into a subject. Genes encoding TCRs can be isolated from T cells that specifically recognize cancer antigens with high avidity. T lymphocytes isolated from peripheral blood can be transduced with a retrovirus or a lentivirus that contains genes encoding TCRs possessing the desired specificity. This method may permit the rapid production to a large number of tumor-antigen-specific T cells for ACT.

T cells may be transduced to express a T cell receptor (TCR) having antigenic specificity for a cancer antigen using transduction techniques described in Heemskerk et al. *Hum Gene Ther.* 19:496-510 (2008) and Johnson et al. *Blood* 114:535-46 (2009). The content of these references is hereby incorporated by reference in their entireties. ACT using T cells genetically modified to express a TCR recognizing an antigen of interest can be performed in accordance with the clinical trial protocol published by Morgan et al., *Science* (2006) 314(5796):126-129. The content of this reference is hereby incorporated by reference in its entirety.

Infusion of minimally expanded T cells, e.g., T cells that have been genetically engineered to express a TCR (or modified TCR) recognizing a tumor antigen, to subjects receiving an ACT regimen may promote the persistence of the transferred cells, stimulate the persistence, proliferation and survival of transferred cells, and improve tumor regression.

In an aspect, TAA peptides that are capable of use with the methods and embodiments described herein include, for example, those TAA peptides described in U.S. Publication 20160187351, U.S. Publication 20170165335, U.S. Publication 20170035807, U.S. Publication 20160280759, U.S. Publication 20160287687, U.S. Publication 20160346371, U.S. Publication 20160368965, U.S. Publication 20170022251, U.S. Publication 20170002055, U.S. Publication 20170029486, U.S. Publication 20170037089, U.S. Publication 20170136108, U.S. Publication 20170101473, U.S. Publication 20170096461, U.S. Publication 20170165337, U.S. Publication 20170189505, U.S. Publication 20170173132, U.S. Publication 20170296640, U.S. Publication 20170253633, U.S. Publication 20170260249, U.S. Publication 20180051080, and U.S. Publication No. 20180164315, the contents of each of these publications and sequence listings described therein are herein incorporated by reference in their entireties. In an aspect, T cells described herein selectively recognize cells which present a TAA peptide described in one of more of the patents and publications described above.

In an aspect, T cell receptors capable of use with methods described herein, include, for example, those described in U.S. Publication No. 20170267738, U.S. Publication No. 20170312350, U.S. Publication No. 20180051080, U.S. Publication No. 20180164315, U.S. Publication No. 20180161396, U.S. Publication No. 20180162922, U.S. Publication No. 20180273602, U.S. Publication No. 20190002556, U.S. Publication NO. 20180135039, the contents of each of these publications are hereby incorporated by reference in their entireties.

In another aspect, TAA that are capable of use with the methods and embodiments described herein include at least one selected from SEQ ID NO: 1 to SEQ ID NO: 157. In an aspect, T cells selectively recognize cells which present a TAA peptide described in SEQ ID NO: 1-157 or any of the patents or applications described herein.

| SEQ ID NO: | Amino Acid Sequence |
|---|---|
| 1 | YLYDSETKNA |
| 2 | HLMDQPLSV |
| 3 | GLLKKINSV |
| 4 | FLVDGSSAL |
| 5 | FLFDGSANLV |
| 6 | FLYKIIDEL |
| 7 | FILDSAETTTL |
| 8 | SVDVSPPKV |
| 9 | VADKIHSV |
| 10 | IVDDLTINL |
| 11 | GLLEELVTV |
| 12 | TLDGAAVNQV |
| 13 | SVLEKEIYSI |
| 14 | LLDPKTIFL |
| 15 | YTFSGDVQL |
| 16 | YLMDDFSSL |
| 17 | KVWSDVTPL |
| 18 | LLWGHPRVALA |
| 19 | KIWEELSVLEV |
| 20 | LLIPFTIFM |
| 21 | FLIENLLAA |
| 22 | LLWGHPRVALA |
| 23 | FLLEREQLL |
| 24 | SLAETIFIV |
| 25 | TLLEGISRA |
| 26 | ILQDGQFLV |
| 27 | VIFEGEPMYL |
| 28 | SLFESLEYL |
| 29 | SLLNQPKAV |
| 30 | GLAEFQENV |
| 31 | KLLAVIHEL |
| 32 | TLHDQVHLL |

-continued

| SEQ ID NO: | Amino Acid Sequence |
|---|---|
| 33 | TLYNPERTITV |
| 34 | KLQEKIQEL |
| 35 | SVLEKEIYSI |
| 36 | RVIDDSLVVGV |
| 37 | VLFGELPAL |
| 38 | GLVDIMVHL |
| 39 | FLNAIETAL |
| 40 | ALLQALMEL |
| 41 | ALSSSQAEV |
| 42 | SLITGQDLLSV |
| 43 | QLIEKNWLL |
| 44 | LLDPKTIFL |
| 45 | RLHDENILL |
| 46 | YTFSGDVQL |
| 47 | GLPSATTTV |
| 48 | GLLPSAESIKL |
| 49 | KTASINQNV |
| 50 | SLLQHLIGL |
| 51 | YLMDDFSSL |
| 52 | LMYPYIYHV |
| 53 | KVWSDVTPL |
| 54 | LLWGHPRVALA |
| 55 | VLDGKVAVV |
| 56 | GLLGKVTSV |
| 57 | KMISAIPTL |
| 58 | GLLETTGLLAT |
| 59 | TLNTLDINL |
| 60 | VIIKGLEEI |
| 61 | YLEDGFAYV |
| 62 | KIWEELSVLEV |
| 63 | LLIPFTIFM |
| 64 | ISLDEVAVSL |
| 65 | KISDFGLATV |
| 66 | KLIGNIHGNEV |
| 67 | ILLSVLHQL |
| 68 | LDSEALLTL |
| 69 | VLQENSSDYQSNL |
| 70 | HLLGEGAFAQV |

-continued

| SEQ ID NO: | Amino Acid Sequence |
|---|---|
| 71 | SLVENIHVL |
| 72 | YTFSGDVQL |
| 73 | SLSEKSPEV |
| 74 | AMFPDTIPRV |
| 75 | FLIENLLAA |
| 76 | FTAEFLEKV |
| 77 | ALYGNVQQV |
| 78 | LFQSRIAGV |
| 79 | ILAEEPIYIRV |
| 80 | FLLEREQLL |
| 81 | LLLPLELSLA |
| 82 | SLAETIFIV |
| 83 | AILNVDEKNQV |
| 84 | RLFEEVLGV |
| 85 | YLDEVAFML |
| 86 | KLIDEDEPLFL |
| 87 | KLFEKSTGL |
| 88 | SLLEVNEASSV |
| 89 | GVYDGREHTV |
| 90 | GLYPVTLVGV |
| 91 | ALLSSVAEA |
| 92 | TLLEGISRA |
| 93 | SLIEESEEL |
| 94 | ALYVQAPTV |
| 95 | KLIYKDLVSV |
| 96 | ILQDGQFLV |
| 97 | SLLDYEVSI |
| 98 | LLGDSSFFL |
| 99 | VIFEGEPMYL |
| 100 | ALSYILPYL |
| 101 | FLFVDPELV |
| 102 | SEWGSPHAAVP |
| 103 | ALSELERVL |
| 104 | SLFESLEYL |
| 105 | KVLEYVIKV |
| 106 | VLLNEILEQV |
| 107 | SLLNQPKAV |
| 108 | KMSELQTYV |

| SEQ ID NO: | Amino Acid Sequence |
|---|---|
| 109 | ALLEQTGDMSL |
| 110 | VIIKGLEEITV |
| 111 | KQFEGTVEI |
| 112 | KLQEEIPVL |
| 113 | GLAEFQENV |
| 114 | NVAEIVIHI |
| 115 | ALAGIVTNV |
| 116 | NLLIDDKGTIKL |
| 117 | VLMQDSRLYL |
| 118 | KVLEHVVRV |
| 119 | LLWGNLPEI |
| 120 | SLMEKNQSL |
| 121 | KLLAVIHEL |
| 122 | ALGDKFLLRV |
| 123 | FLMKNSDLYGA |
| 124 | KLIDHQGLYL |
| 125 | GPGIFPPPPPQP |
| 126 | ALNESLVEC |
| 127 | GLAALAVHL |
| 128 | LLLEAVWHL |
| 129 | SIIEYLPTL |
| 130 | TLHDQVHLL |
| 131 | SLLMWITQC |
| 132 | FLLDKPQDLSI |
| 133 | YLLDMPLWYL |
| 134 | GLLDCPIFL |
| 135 | VLIEYNFSI |
| 136 | TLYNPERTITV |
| 137 | AVPPPPSSV |
| 138 | KLQEELNKV |
| 139 | KLMDPGSLPPL |
| 140 | ALIVSLPYL |
| 141 | FLLDGSANV |
| 142 | ALDPSGNQLI |
| 143 | ILIKHLVKV |
| 144 | VLLDTILQL |
| 145 | HLIAEIHTA |
| 146 | SMNGGVFAV |
| 147 | MLAEKLLQA |
| 148 | YMLDIFHEV |
| 149 | ALWLPTDSATV |
| 150 | GLASRILDA |
| 151 | SYVKVLHHL |
| 152 | VYLPKIPSW |
| 153 | NYEDHFPLL |
| 154 | VYIAELEKI |
| 155 | VHFEDTGKTLLF |
| 156 | VLSPFILTL |
| 157 | HLLEGSVGV |

T Cells Genetically Modified to Express a Chimeric Antigen Receptor (CAR)

Genetic engineering of T cells to express a TCR having a desired specificity as described above may be a very promising approach for ACT. Notwithstanding, there is the potential for mispairing of the engineered TCR alpha and beta chains with endogenous TCR chains. In addition, the success of ACT using cells expressing engineered TCR depends on expression of the specific MHC molecule recognized by the TCR in the targeted cancer cells. To avoid these potential complications, T cells may alternatively be engineered to express chimeric antigen receptors (CARs).

In their simplest form, CARs may contain an antigen binding domain coupled with the transmembrane domain and the signaling domain from the cytoplasmic tail of the CD3ζ chain. There is some evidence that the CD3ζ chain may be insufficient to fully activate transduced T cells. Accordingly, CARs may preferably contain an antigen binding domain, a costimulatory domain, and a CD3ζ signaling domain. Using a costimulatory domain in combination with the CD3ζ signaling domain mimics the two-signal model of T cell activation. The CAR antigen binding domain can be an antibody or antibody fragment, such as a Fab or an scFv.

The antigen binding domain is separated from the CD3ζ signaling domain and the costimulatory domain by a transmembrane domain. The transmembrane domain may be derived from any transmembrane protein. In one embodiment, a transmembrane domain naturally associated with one of the domains in the CAR may be used. In another embodiment, an exogenous or synthetic transmembrane domain is used. In some embodiments, the transmembrane domain can be selected or modified by amino acid substitution to minimize interactions with other membrane proteins.

Between the extracellular domain and the transmembrane domain of the CAR, or between the cytoplasmic domain and the transmembrane domain of the CAR, a spacer may optionally be incorporated. The spacer may be any oligo- or polypeptide that functions to link the transmembrane domain to either the extracellular domain or the cytoplasmic domain. A spacer may contain up to 300 amino acids, preferably 10 to 100 amino acids, and more preferably 25 to 50 amino acids.

The intracellular domain of a CAR may be responsible for activation of at least one of the normal effector functions of the immune cell, in which the CAR is expressed. Effector functions may include, for example, cytolytic activity or helper activity, such as the secretion of cytokines. Thus, intracellular signaling domain of a molecule may refer to the portion of a protein, which transduces the effector function signal and directs the cell to perform a specialized function. While the entire intracellular signaling domain can be used, in many cases a portion of the intracellular domain may be used, so long as the selected portion transduces the effector function signal. The cytoplasmic domain of a CAR can include the CD3ζ signaling domain on its own, or in combination with a costimulatory domain. The costimulatory domain contains the intracellular domain of a costimulatory molecule. Costimulatory molecules may be cell surface molecules that promote an efficient response of lymphocytes to antigen. In some embodiments, the costimulatory domain may contain an intracellular domain of a costimulatory molecule, such as 4-1BB, CD27, CD28, OX40, CD30, CD40, PD-1, ICOS, lymphocyte function-associated antigen-1 (LFA-1), CD2, CD7, LIGHT, NKG2C, B7-H3, a CD83 ligand, or combinations thereof. In an exemplary embodiment, the costimulatory molecule may be the intracellular domain of 4-1 BB or CD28.

Infusion of minimally expanded T cells, e.g., T cells that have been genetically engineered to express a CAR recognizing a tumor antigen, to subjects receiving an ACT regimen may promote the persistence of the transferred cells, stimulate the persistence, proliferation and survival of transferred cells, and improve tumor regression.

As noted above, treatment of solid tumors may require T cells to withstand CWID more than AICD. Conventional methods of determining persistence of manufactured T cells in cognate antigen-limited solid tumor environment often depend on animal models. In contrast, embodiments of the present disclosure use in vitro assays as surrogates to determine T cell manufacturing conditions that may enhance persistence of T cells in vivo. To this end, manufactured T cells may be tested in non-cognate antigen or low cognate antigen environments. For example, manufactured T cells may be seeded in the culture at low densities, e.g., from about 1,000 to about 1×10$^6$ cells/cm$^2$, from about 1,000 to about 500,000 cells/cm$^2$, from about 1,000 to about 250,000 cells/cm$^2$, from about 1,000 to about 200,000 cells/cm$^2$, from about 1,000 to about 150,000 cells/cm$^2$, from about 1,000 to about 100,000 cells/cm$^2$, from about 1,000 to about 50,000 cells/cm$^2$, from about 1,000 to about 10,000 cells/cm$^2$, or from about 1,000 to about 5,000 cells/cm$^2$, in the absence of cognate antigen-presenting cells, e.g., cognate antigen-presenting tumor cells, dendritic cells, or macrophages. To test manufactured T cells in reduced cytokine stimulation environments, manufactured T cells may be cultured in the non-cognate antigen or low cognate antigen environments in the presence of low concentrations of cytokines, e.g., from about 1 to about 1,000 ng/ml, from about 1 to about 500 ng/ml, from about 1 to about 250 ng/ml, from about 1 to about 100 ng/ml, from about 1 to about 50 ng/ml, from about 5 to about 50 ng/ml, from about 5 to about 40 ng/ml, from about 5 to about 30 ng/ml, from about 5 to about 20 ng/ml, or from about 5 to about 10 ng/ml, for a long period of time, e.g., from about 1 to about 30 days, from about 2 to about 25 days, from about 3 to about 21 days, from about 3 to about 14 days, from about 3 to about 10 days, or from about 3 to about 7 days.

EXAMPLES

Example 1

Cytokine Sensitivity Assay (CSA)

To investigate the role of ex vivo T-cell expansion length on T-cell fitness, T-cells were manufactured for 4, 7, or 10 days. After this manufacturing, the T-cells were analyzed via the CSA and the following metrics were analyzed: (1) cell survival as measured by fold growth of T-cells, (2) apoptosis as measured via propidium iodide and Annexin-V stain, (3) division as measured by the dilution of proliferation dye PkH67, (4) cytokine receptor expression as measured by flow cytometry, and (5) T-cell memory phenotype as measured by flow cytometry.

CSA shows prolonged expansions may lead to a significant reduction in the fitness of the T-cells when assessed within the CSA as assessed by the following observations: (1) decreased T-cell survival, (2) increased apoptosis, (3) decreased division rate, (4) cytokine receptor expression correlation, and (5) decreased survival of the $T_{naive/scm}$ compartment.

CSA was performed for 21 days, each sample was analyzed at 7 time points, which may define a single metric for temporal behavior. For this purpose, the area under the curve (integration) of the temporal data was calculated and is used as a single defining metric to represent the behavior of the sample over the 21 days in the following results.

Apheresed T cells may be obtained from healthy allogenic donors or patients. These T cells may be activated or stimulated with activating anti-CD3 antibody, e.g., OKT3, in the presence of IL-2, or with anti-CD3- and anti-CD28 antibodies-coated paramagnetic beads in the presence of IL-2, or with artificial antigen presenting cell (aAPC) expressing 4-1BBL and an Fc receptor with OKT3 and IL-2. Activated T cells may then be transduced with recombinant TCR using retro- or lentiviral platform. Transduced T cells may be expanded for different lengths of time, for example, 4 days (Day 4), 7 days (Day 7), or 10 days (Day 10), in which activation starts on Day 0. Because recombinant TCR may be integrated into T cell genomes, all daughter cells generated during expansion may also express recombinant TCR. Expanded/transduced T cells may be used immediately or may be cryopreserved for future use.

Figure 4:
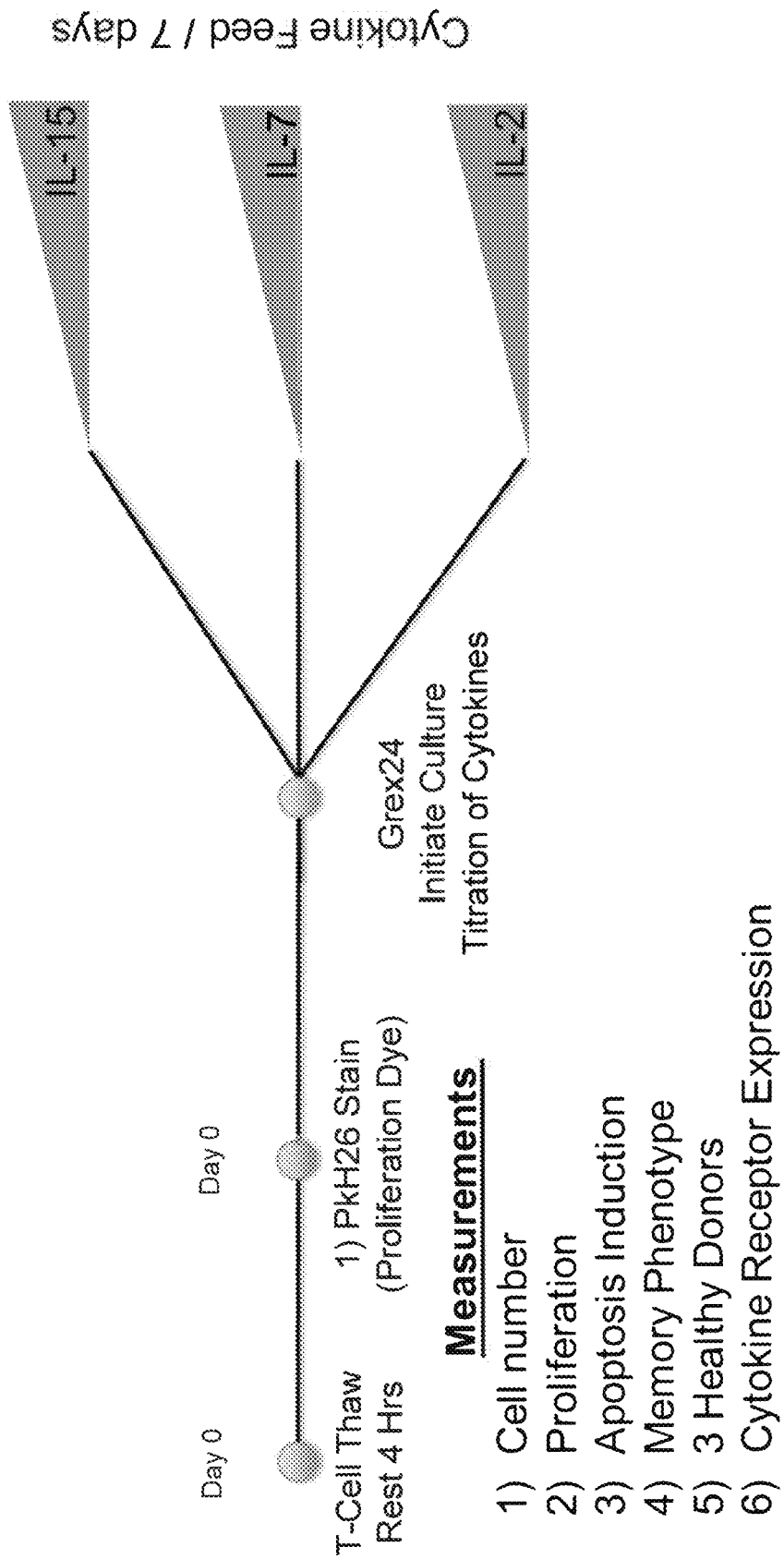
FIG. 4 shows cytokine sensitivity assay according to one embodiment of the present disclosure.

FIG. 4 shows an embodiment of a cytokine sensitivity assay described herein. In FIG. 4, cryopreserved or frozen expanded TCR-transduced T cells (e.g., for 4 days, 7 days, or 10 days) may be thawed and rested for 4 hours without cytokine before added to cell culture wells at a limited number, e.g., 2×10$^5$ cells/well. Proliferation dye, e.g., PkH26 stain and respective cytokines (e.g., IL-2, IL-15, IL-7, or a combination thereof) at varying concentrations may be added and incubated for a period of time, for example, 21 days. Fresh cytokines may be fed to cultured T cells every 7 days, i.e., on Day 0, Day 7, and Day 14, during the 21-day assay. Towards the end of every 7 days in assay, culture media would have reduced levels of cytokines as compared with that at the start of assay. At different times in the assay, expanded engineered T cells may be collected and analyzed for cell numbers, proliferation, apoptosis, e.g., via Annexin-V staining, memory phenotypes, e.g., CD45RO and CCR7 markers, and cytokine receptor expression, e.g., IL-2 receptor (CD25), IL-7 receptor (CD127), and IL-15 receptor (CD122).

Example 2

Figure 5:
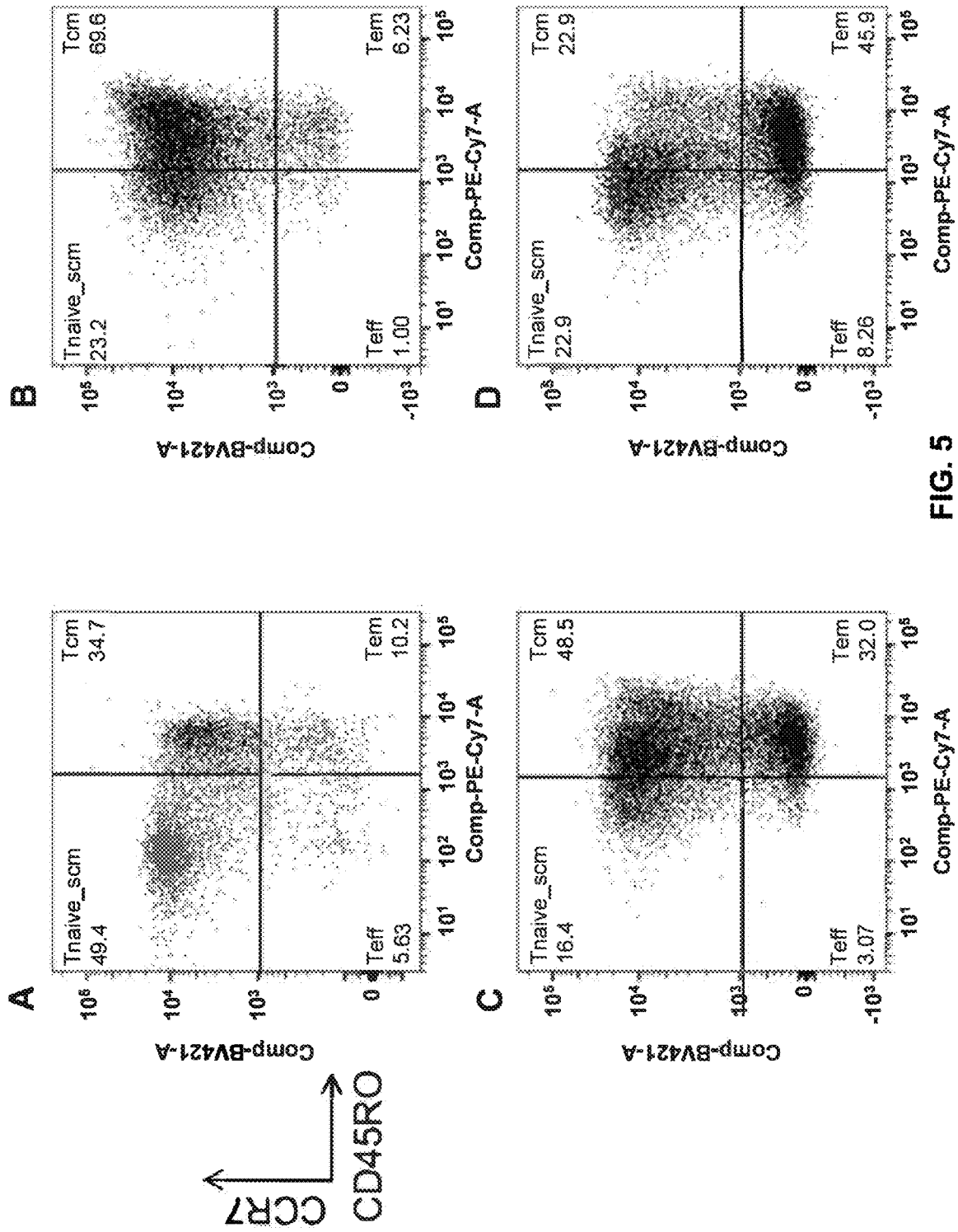
FIG. 5 shows $T_{scm}$-like formation during in vitro expansion characterized by CD45RO(low) and CCR7+.

Shortened In Vitro Expansion of T Cells Exhibit Persistent $T_{scm}$-Like Phenotype (Desired for In Vivo Efficacy) Over a 21-Day Assay FIG. 5 shows phenotypes of TCR-transduced T cells, which were obtained from a healthy donor and expanded for (A) 0 day, (B) 4 days, (C) 7 days, and (D) 10 days. Expanded T cells were separated from lymphocytes by CD45RO staining and subsequently by CCR7 staining to discriminate $T_{naive}/T_{scm}$ (CD45RO−CCR7+), e.g., 23.2% (Day 4 expanded T cells), 16.4% (Day 7 expanded T cells), and 22.9% (Day 10 expanded T cells). Compared with Day 0 (49.4%, without expansion), Day 4, Day 7, and Day 10 expanded T cells show decreased number of cells with $T_{scm}$-like phenotype.

To examine the effect of cytokine deprivation on TCR-transduced T cells, T cells expanded for 4 days, 7 days, or 10 days were cultured in the presence of IL-15 for 21 days. Fresh IL-15 (10 ng/ml) was fed to cultured T cells every 7 days, i.e., on Day 0, Day 7, and Day 14, during the 21-day assay. $T_{scm}$-like phenotype was examined by flow cytometry using CD45RO and CCR7 staining at the end of every 7-day IL-15 feed, i.e., on Day 7, Day 14, and Day 21, when IL-15 levels were lowest in culture.

Figure 6:
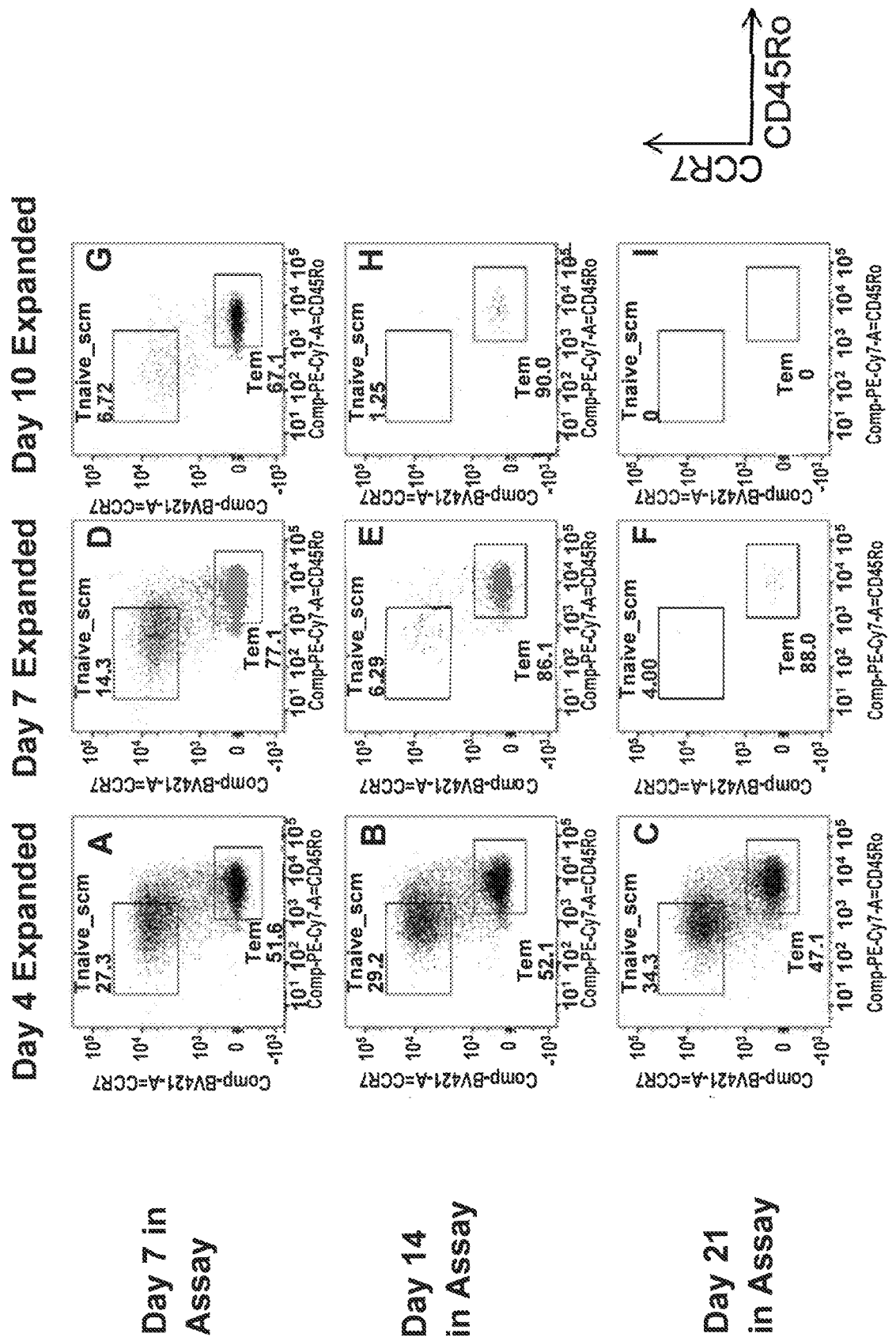
FIG. 6 shows early expanded $T_{scm}$ retain IL-15 cytokine sensitivity across 21 Days in assay.

FIG. 6 indicate that Day 4 expanded T cells exhibit better IL-15 sensitivity by retaining $T_{scm}$-like, i.e., $T_{naive}/T_{scm}$, cell population throughout the 21-day assay. Because $T_{scm}$-like phenotypes correlate with T cell persistence in vivo, these results suggest that earlier expanded (for example, about 4 days) engineered T cells may be better than those expanded for a longer period of time, for example, greater or equal to about 7 days.

To investigate which T-cell memory compartments are persisting, flow cytometry-based phenotyping of the T-cells were performed every 7 days during the culturing period.

FIG. 21A shows, at Day 21 of the expansion, significantly higher percentages of naïve (scm) and central memory ($T_{cm}$) T cells in the 3-day (early) expanded samples, while both of these less-differentiated T-cell compartments were drastically reduced in the 7-day (Mid) and 10-day (Late) expanded samples.

FIG. 21B shows, consistently, there was an increase in proliferation of the CCR7-expressing cells based on PkH dilution by day 7 in the culturing period with IL-15, suggesting that reduced expansion may result in retention of proliferation potential through increased expression of cytokine receptors. Collectively, this data shows that early-expanded T cells retain a population of early differentiated CD8+ T-cells capable of proliferating in response to IL-2, IL-7, and IL-15.

Example 3

Shortened In Vitro Expansion of T Cells Correlates with Increased Survival

Thawed, expanded T-cells were assessed for their ability to survive in the presence of IL-7, IL-15, or IL-2 in the absence of additional antigen or CD3 stimulation. Day 4 expanded T-cells were able to substantially outgrow the later expanded T-cells in all three cytokine conditions with an approximately 10-, 30-, and 15-fold peak fold growth in IL-7, IL-15, and IL-2. Conversely, day 7 and day 10 expanded T cells were unable to sustain substantial growth in any of the cytokine conditions. Further, in the absence of all cytokines, each T-cell population died at a similar rate regardless of expansion protocol length.

Figure 7:
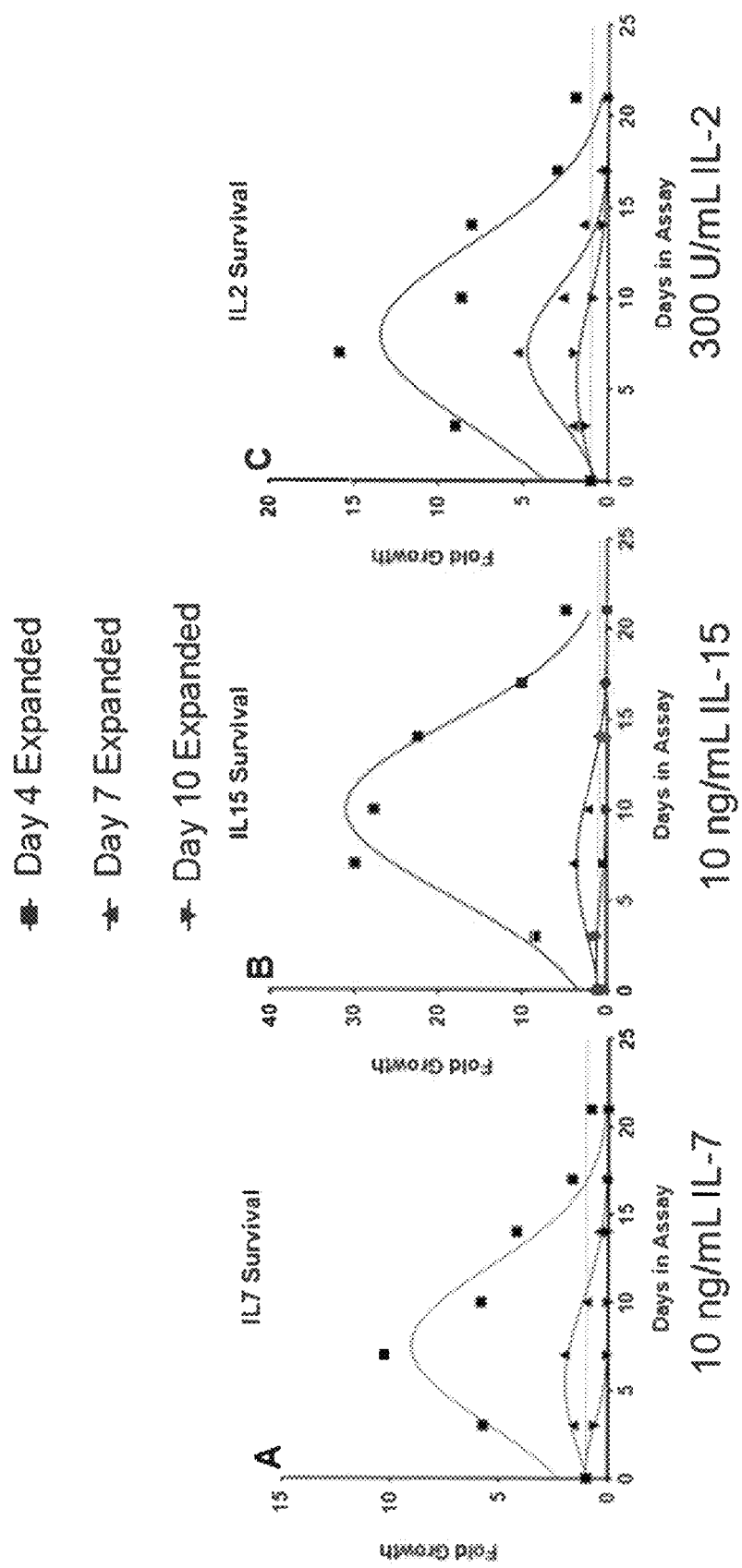
FIG. 7 shows that early expanded cells (expansion for about 4 days) demonstrate increased cell growth relative to expansion at 7 and 10 days. The label under the graphs represents the amount of cytokine used. A linear quadratic line fit is used to model cell behaviour. T-cells expanded for 4, 7, or 10 days were assessed via in the presence of 10 ng/ml IL-7 (A), 10 ng/ml IL-15 (B), or 300 U/mL IL-2 (C) over a period of 21 days with sampling every 2-3 days. Fold growth is calculated as the ratio of the starting T-cell number to the T-cell number at the designated time point. Note that each plot has a different scale on the Y-axis to facilitate data visualization. Best fit lines are derived by linear quadratic equations of cell survival.

To determine the effect of cytokine deprivation on proliferation or survival of expanded T cells, cell growth of expanded TCR-transduced T cells in the presence of IL-2, IL-7, or IL-15 were measured over 21 days. FIG. 7 shows that T cells expanded at Day 4 exhibit higher cell growth or more surviving cells in the presence of (A) IL-7, (B) IL-15, and (C) IL-2 over a 21-day period as compared to those expanded for a longer period of time, for example, Day 7 and Day 10 expansion. The dotted line is set at 1 to indicate no difference in fold growth relative to the starting number of cells.

Figure 8A:
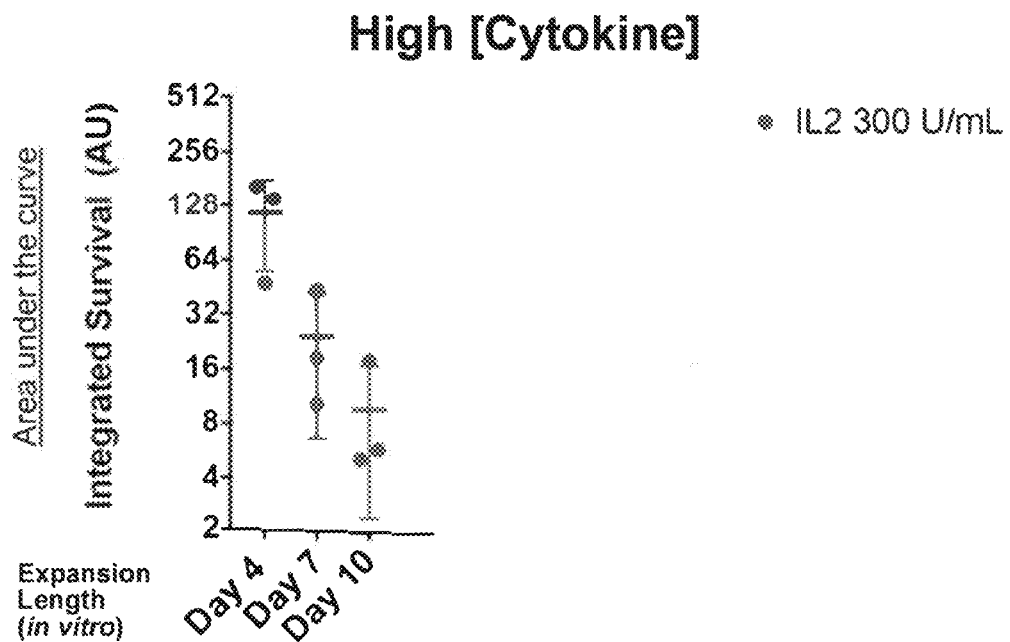
FIGS. 8A-8C show shortened in vitro expansion of T cells (expansion for about 4 days) correlates with increased survival at higher cytokine concentrations relative to expansion at 7 and 10 days. T-cells expanded for 4, 7, or 10 days were assessed via in the presence of 300 U/ml IL-2 (A), 10 ng/ml IL-7 (B), 10 ng/ml IL-15 (C), or over a period of 21 days with sampling every 2-3 days. Integrated survival is the area under the curve of the fold growth plots as shown in FIGS. 7A-7C. Each point represents three technical replicates of each donor with a total of 3 donors shown.
Figure 8B:
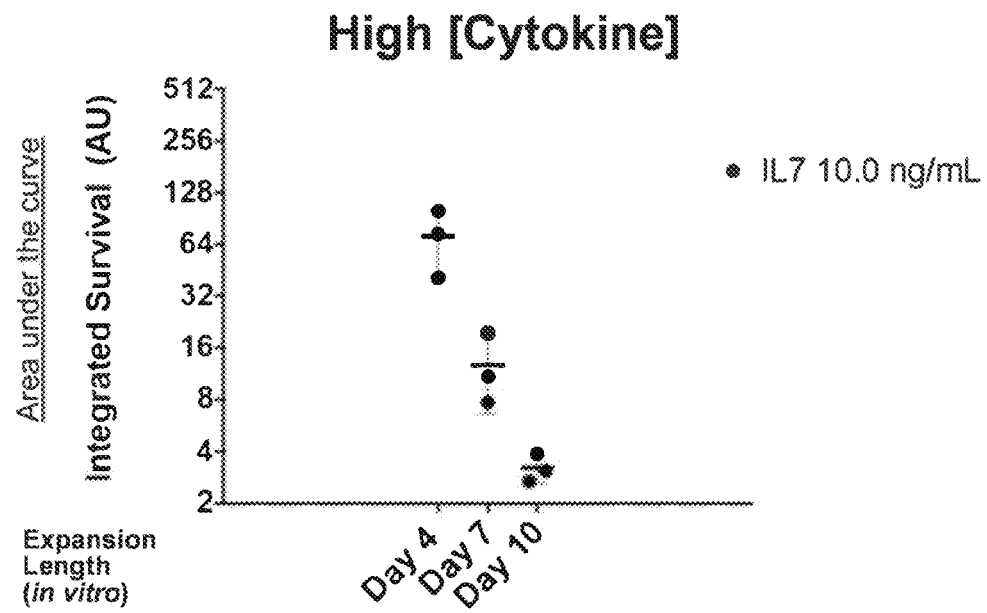
Figure 8C:
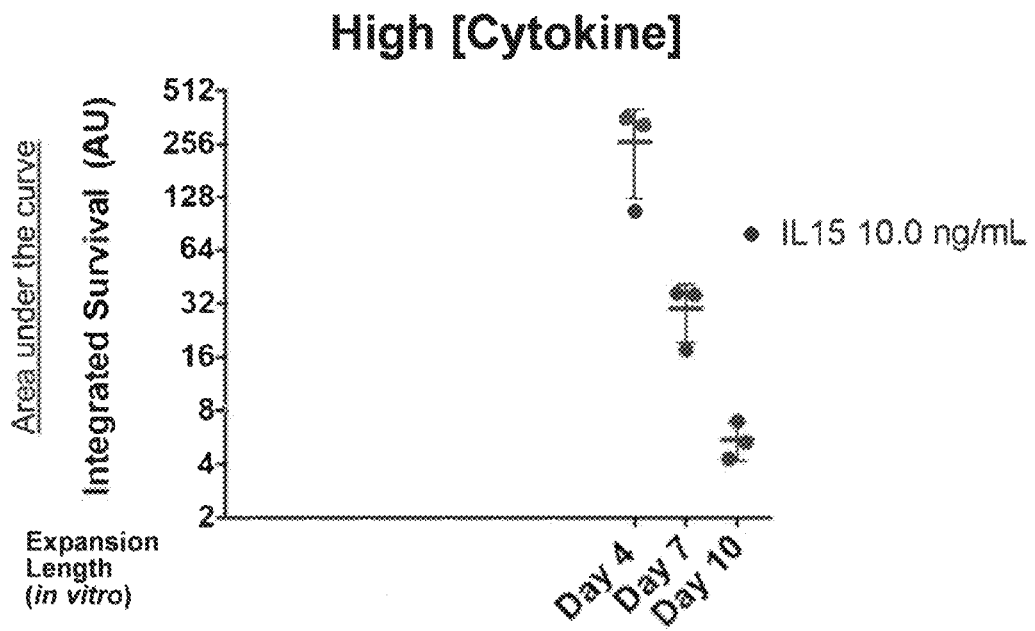

Cell behavior over time is better for earlier expanded TCR-transduced T cells than for those expanded for a longer period of time in the presence of higher concentrations of cytokines, for example, IL-2 (300 U/ml) (FIG. 8A), IL-7 (10.0 ng/ml) (FIG. 8B), or IL-15 (10.0 ng/ml) (FIG. 8C). The integrated survival of each fold growth curve were determined by calculating the area under the curve. From an analysis of three biological donors, there was a trend in which the earlier expanded T cells outperformed the later expanded cells. For IL-2, there was an approximately 5-fold drop in survival between day 4 and day 7 expanded cells, with an approximately 2-fold drop in survival between day 7 and day 10 expanded cells. For IL-7, there was an approximately 6-fold drop in integrated survival between day 4 and day 7 expanded cells, with an approximately 4-fold drop between day 7 and day 10 expanded cells. For IL-15, there was an approximately 8-fold drop in integrated survival between day 4 and day 7 expanded cells, with an approximately 6-fold drop between day 7 and day 10 expanded cells. While there was no statistical significance due to the large degree of donor to donor variation, there was a consistent trend, in which the earlier expanded cells out survived the later expanded cells.

Figure 8D:
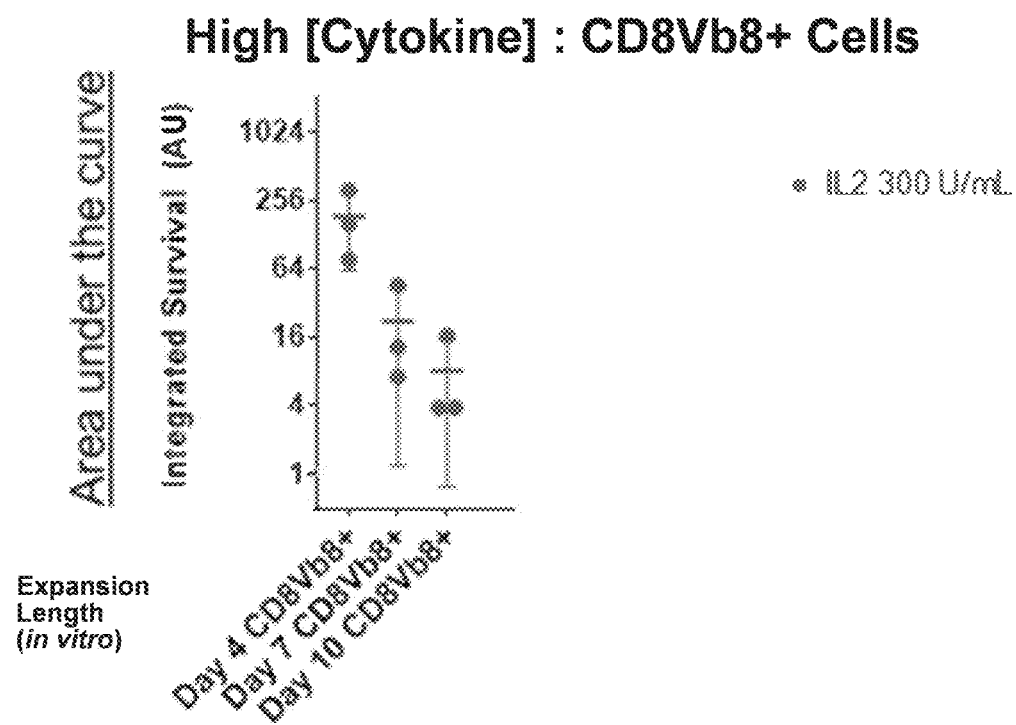
FIGS. 8D-8F show shortened in vitro expansion of transduced T cells correlates with increased survival at higher cytokine concentrations.
Figure 8E:
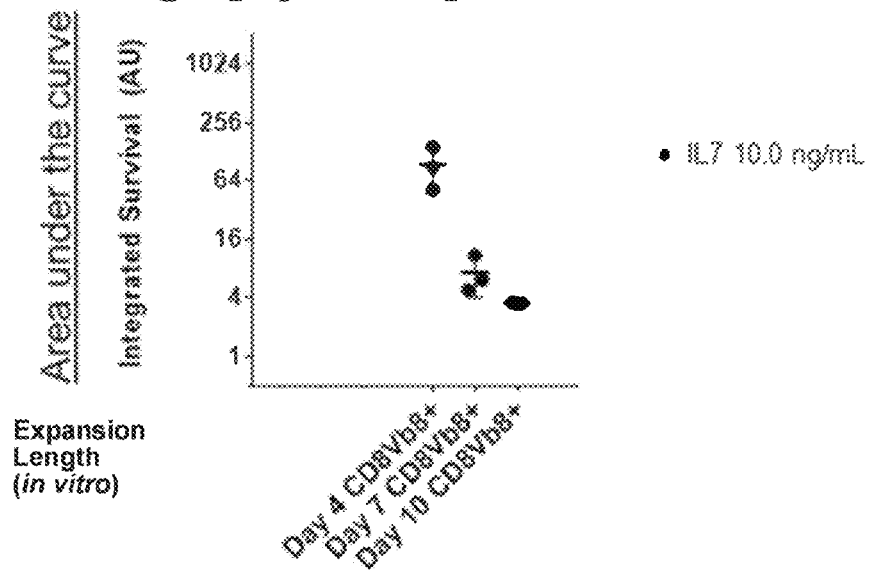
Figure 8F:
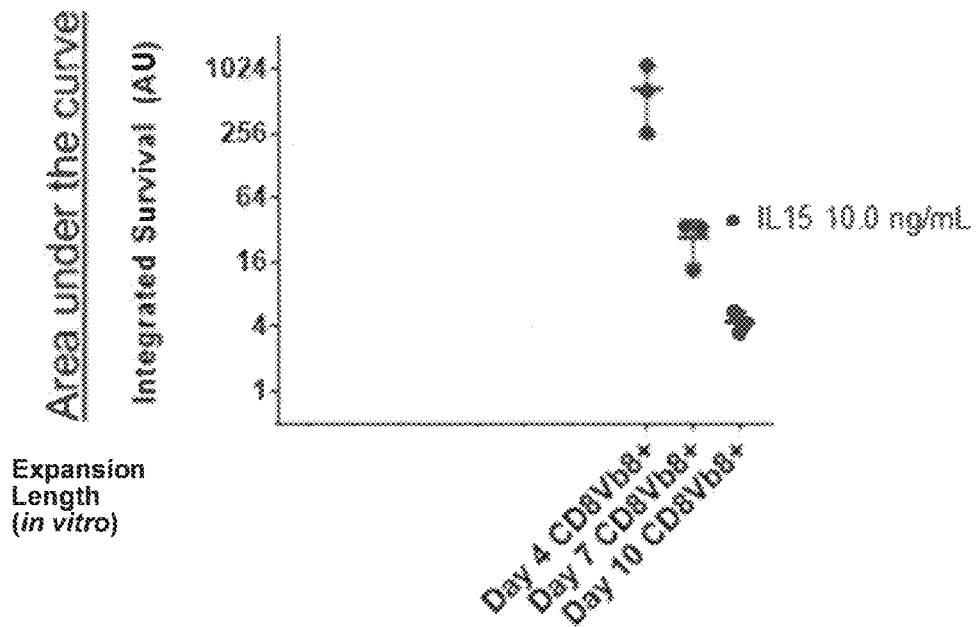

On Day 21 in the assay, integrated survival is also better for earlier expanded TCR (e.g., CD8Vb8+) transduced T cells than for those expanded for longer period of time in the presence of higher concentrations of cytokines, for example, IL-2 (300 U/ml) (FIG. 8D), IL-7 (10.0 ng/ml) (FIG. 8E), or IL-15 (10.0 ng/ml) (FIG. 8F).

Figure 9A:
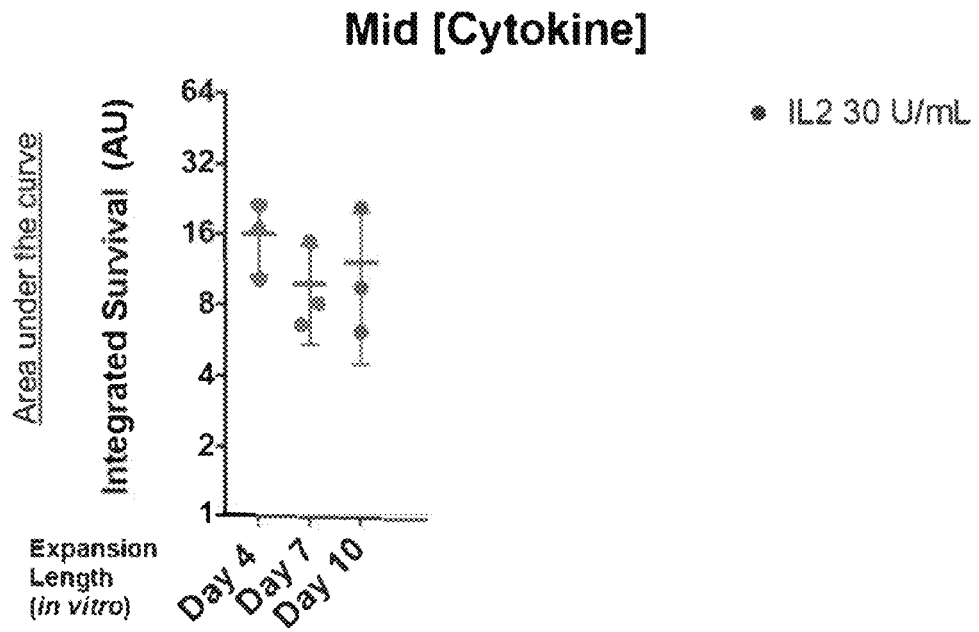
FIGS. 9A-9C show shortened in vitro expansion of T cells correlates with increased survival at lower cytokine concentrations.
Figure 9B:
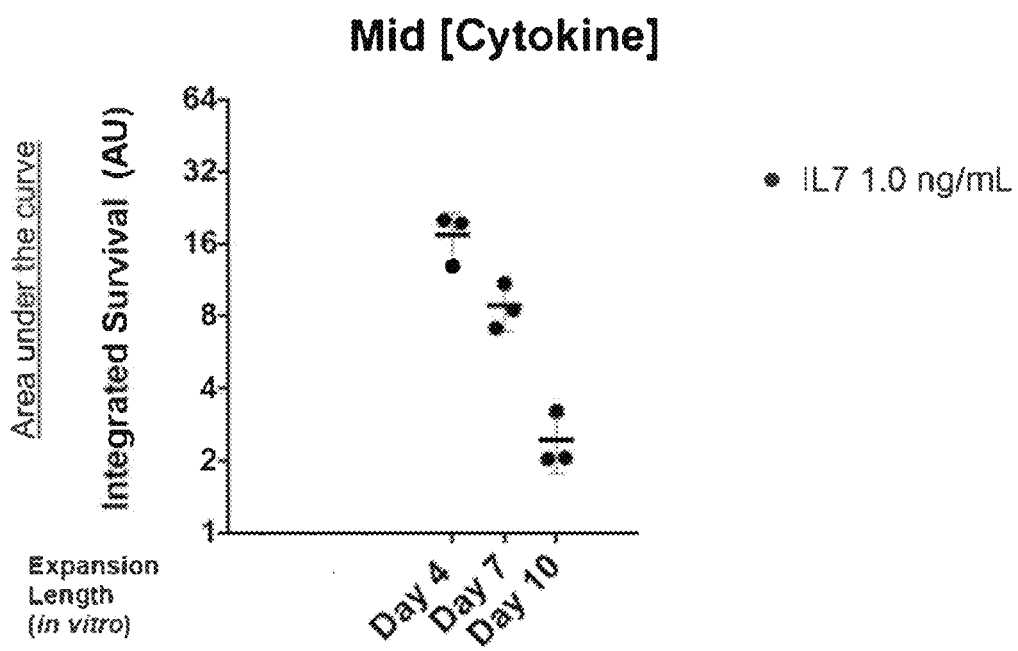
Figure 9C:
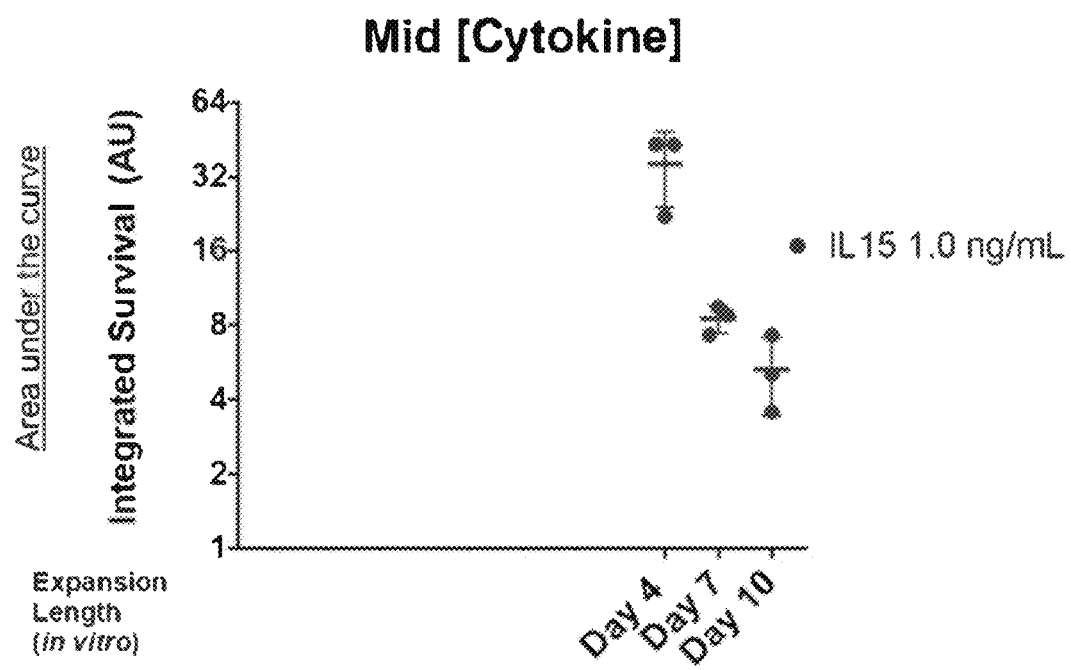

Similar results were also observed in the presence of lower concentrations of cytokines, for example, IL-2 (30 U/ml) (FIG. 9A), IL-7 (1.0 ng/ml) (FIG. 9B), or IL-15 (1.0 ng/ml) (FIG. 9C). For instance, on Day 21 in the assay, better survival of T cells expanded for 4 days as compared to those T cells expanded at longer periods of time, for example, 7 and 10 days of expansion. These results show shortened in vitro expansion of T cells correlates with increased survival in cytokine deprived conditions.

Example 4

Shortened In Vitro Expansion of T Cells Correlates with Decreased Apoptosis

Since there was an increased fold growth of the earlier expanded cells and an increased division, there could be a corresponding decrease in apoptosis as assessed via the staining by propidium iodide (PI) and Annexin-V.

Figure 10:
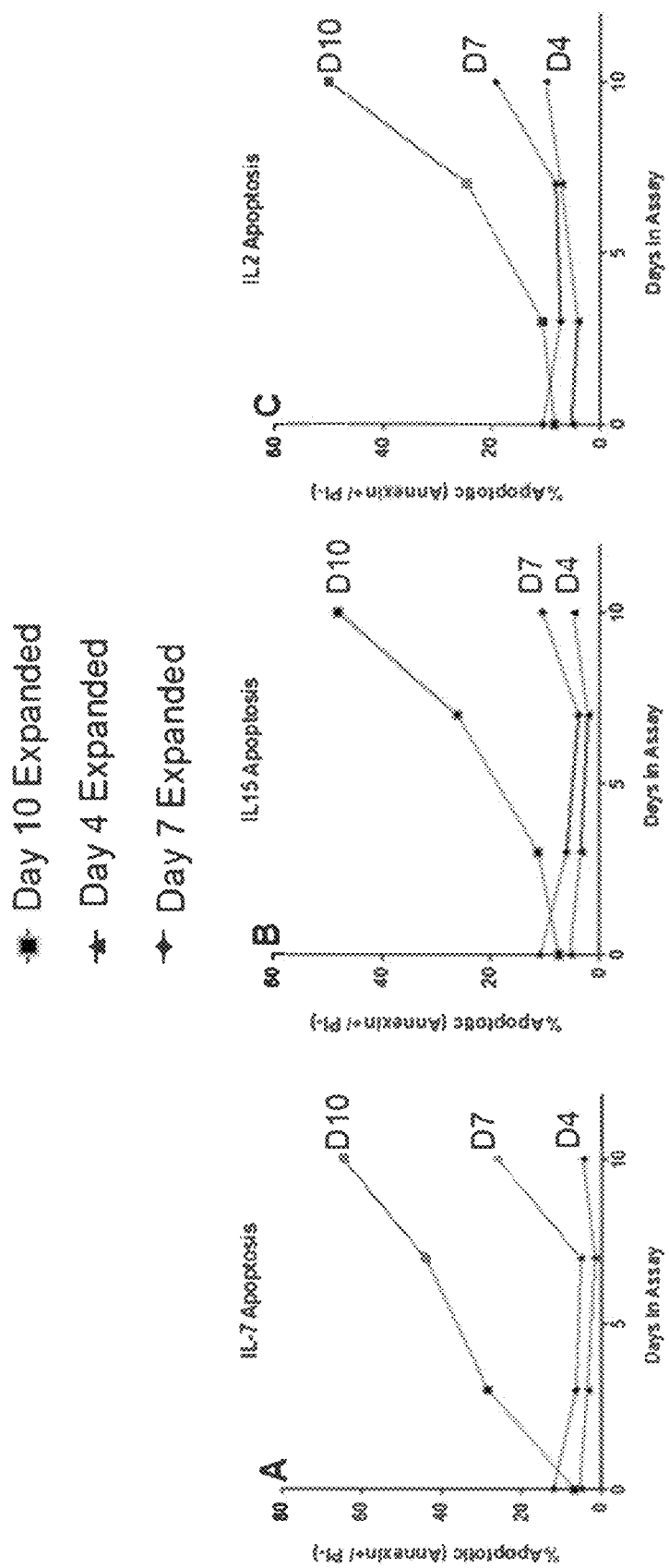
FIG. 10 shows shortened in vitro expansion of T cells correlates with reduced apoptosis.
Figure 11A:
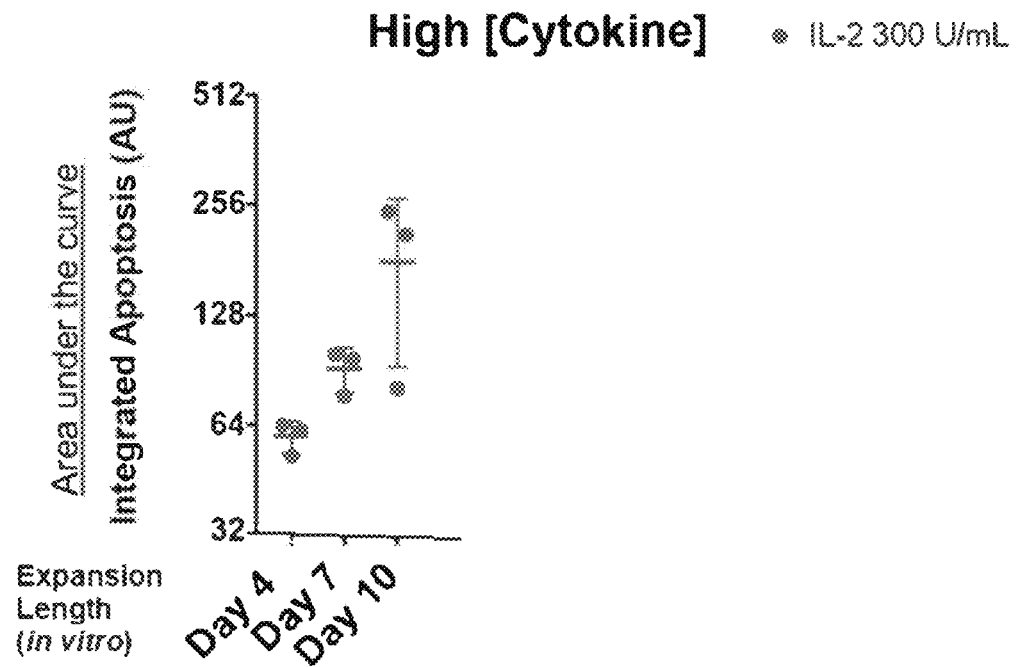
FIGS. 11A-11C show shortened in vitro expansion of T cells correlates with reduced apoptosis at higher cytokine concentrations. T-cells expanded for 4, 7, or 10 days were assessed via in the presence of 300 U/ml IL-2 (A), 10 ng/ml IL-7 (B), or 10 ng/ml IL-15 (C), over a period of 21 days with sampling every 2-3 days. Integrated apoptosis is calculated based on the percentage of lymphocytes staining positive for propidium iodide and annexin-V by day 10 in the assay. Each point represents three technical replicates of each donor with a total of 3 donors shown.
Figure 11B:
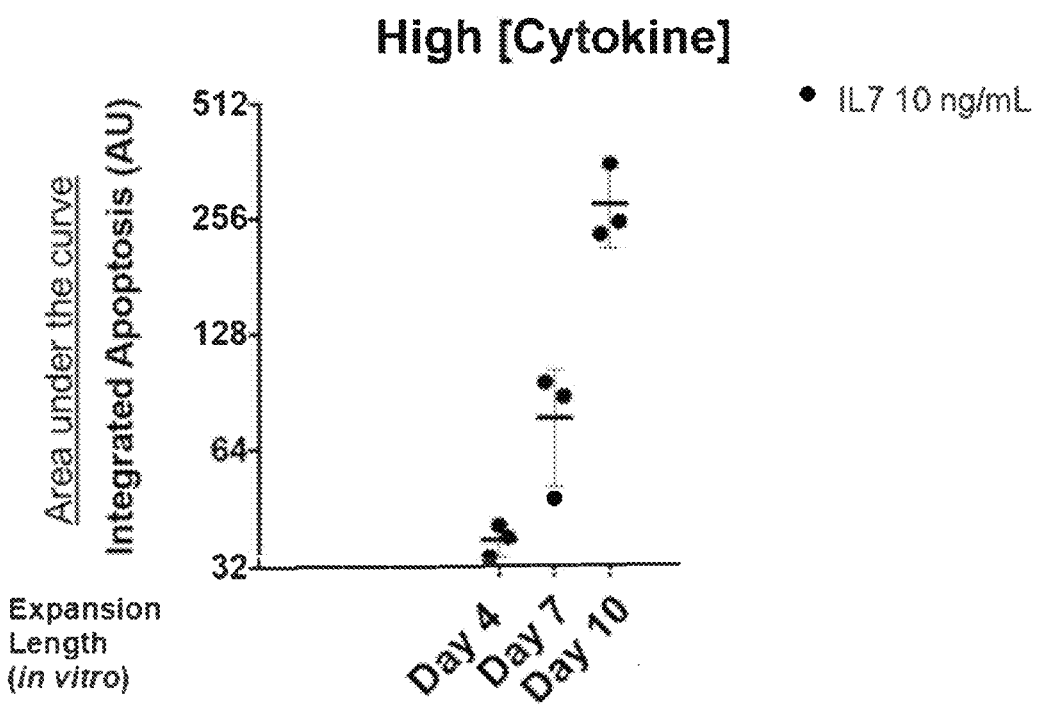
Figure 11C:
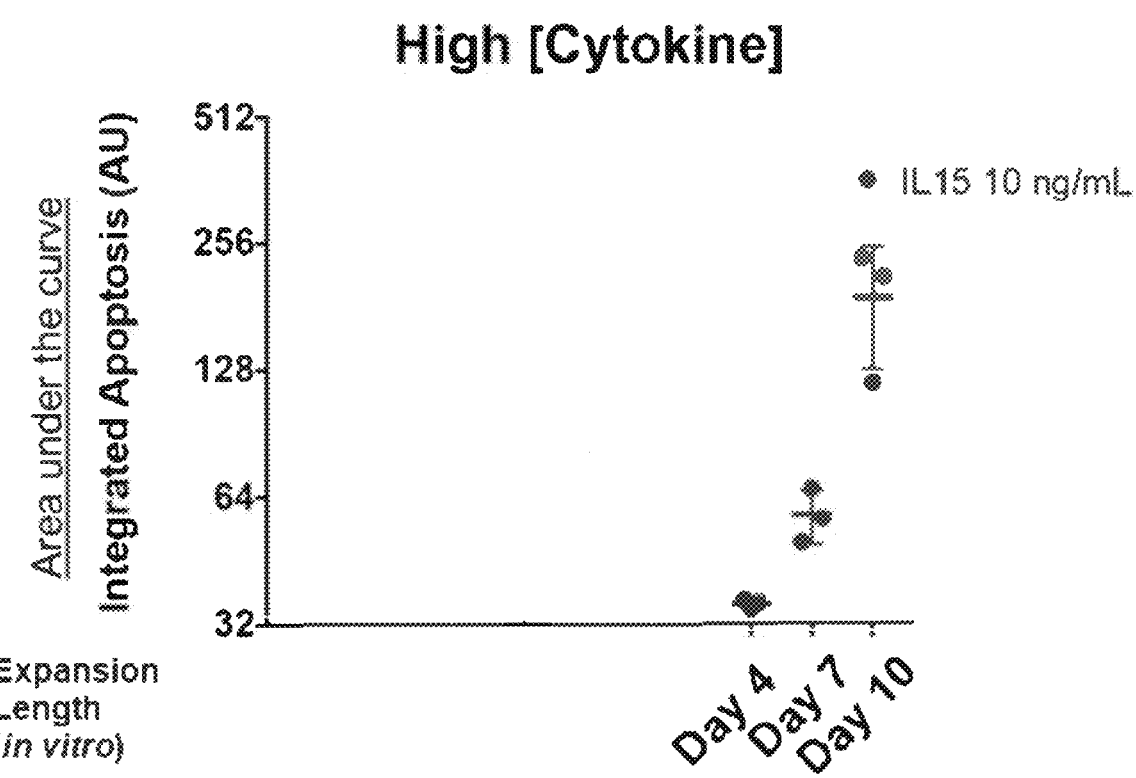

To determine effect of cytokine deprivation on apoptosis of expanded T cells, apoptosis of expanded T cells in the presence of IL-2, IL-7, or IL-15 was measured over 21 days. FIG. 10 shows that T cells expanded for 4 days contain fewer apoptotic cells in the presence of (A) IL-7 (10 ng/ml), (B) IL-15 (10 ng/ml), and (C) IL-2 (300 IU/m1) as compared to those expanded for 7 and 10 days. The % apoptosis of lymphocyte was gated by excluding debris and low FSC populations. FIGS. 11A-11C show, on Day 10 in the assay, lower integrated apoptosis, as determined by the area under curve, of TCR-transduced T cells expanded at about 4 days. For IL-2 conditions, there was a statistically insignificant increase (approximately 1.8-fold) in apoptosis between day 4 and day 7 cells, while there was a statistically significant (p=0.0092) increase (approximately 3-fold) between day 4 and day 10 cells. For IL-7 conditions, there was a statistically insignificant increase (approximately 2-fold) in apoptosis between day 4 and day 7 cells, while there was a statistically significant (p<0.0001) increase (approximately 7-fold) between day 4 and day 10 cells. For IL-15 conditions, there was a statistically insignificant increase (approximately 1.6-fold) in apoptosis between day 4 and day 7 cells, while there was a statistically significant (p=0.0010) increase (approximately 5.5-fold) between day 4 and day 10 cells.

Figure 12:
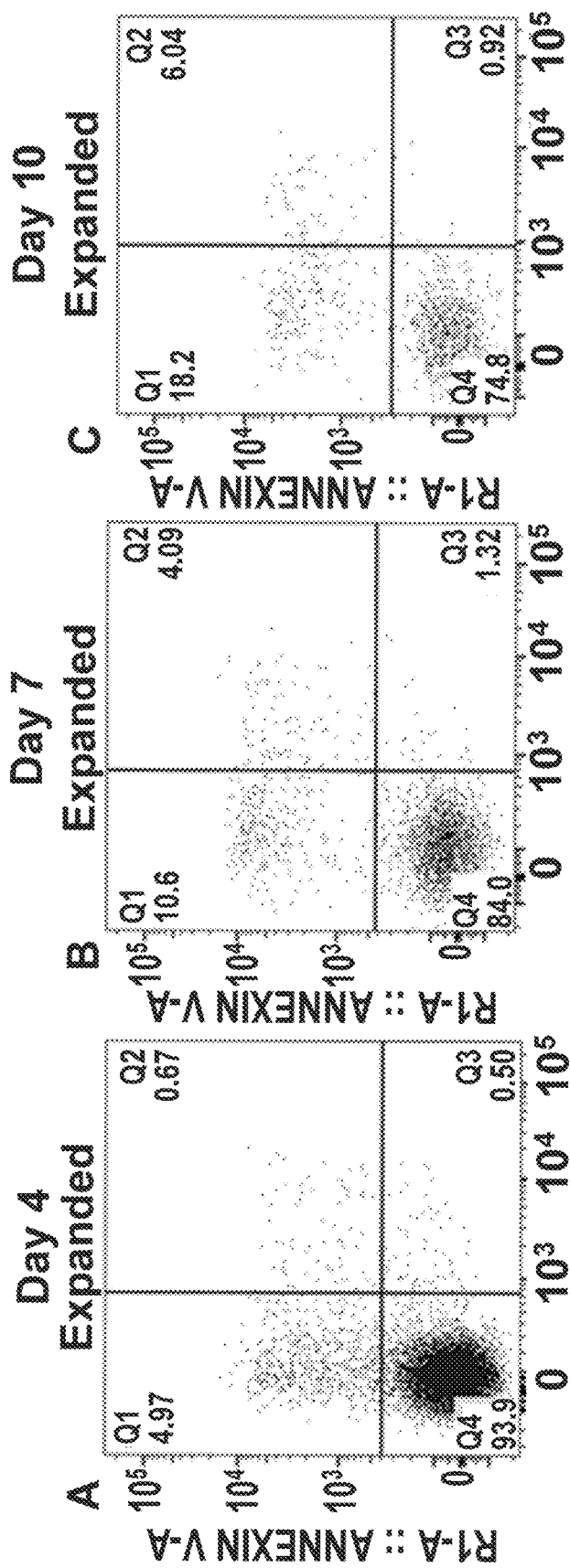
FIG. 12 shows shortened in vitro expansion of T cells correlates with reduced apoptosis.

FIG. 12 indicates that, on Day 10 in the assay, T cells expanded at 4 days contain fewer (4.97%, Annexin-V+/PI−) (A) apoptotic cells than those expanded for a longer period of time, for example, (B) Day 7 (10.6%, Annexin-V+/PI−) and (C) Day 10 (18.2%, Annexin-V+/PI−), in the presence of IL-15 (10 ng/ml). These results demonstrate that shortened in vitro expansion of T cells correlates with decreased apoptosis in cytokine deprived conditions.

Example 5

Shortened In Vitro Expansion of T Cells Correlates with Increased Cell Division

Figure 13:
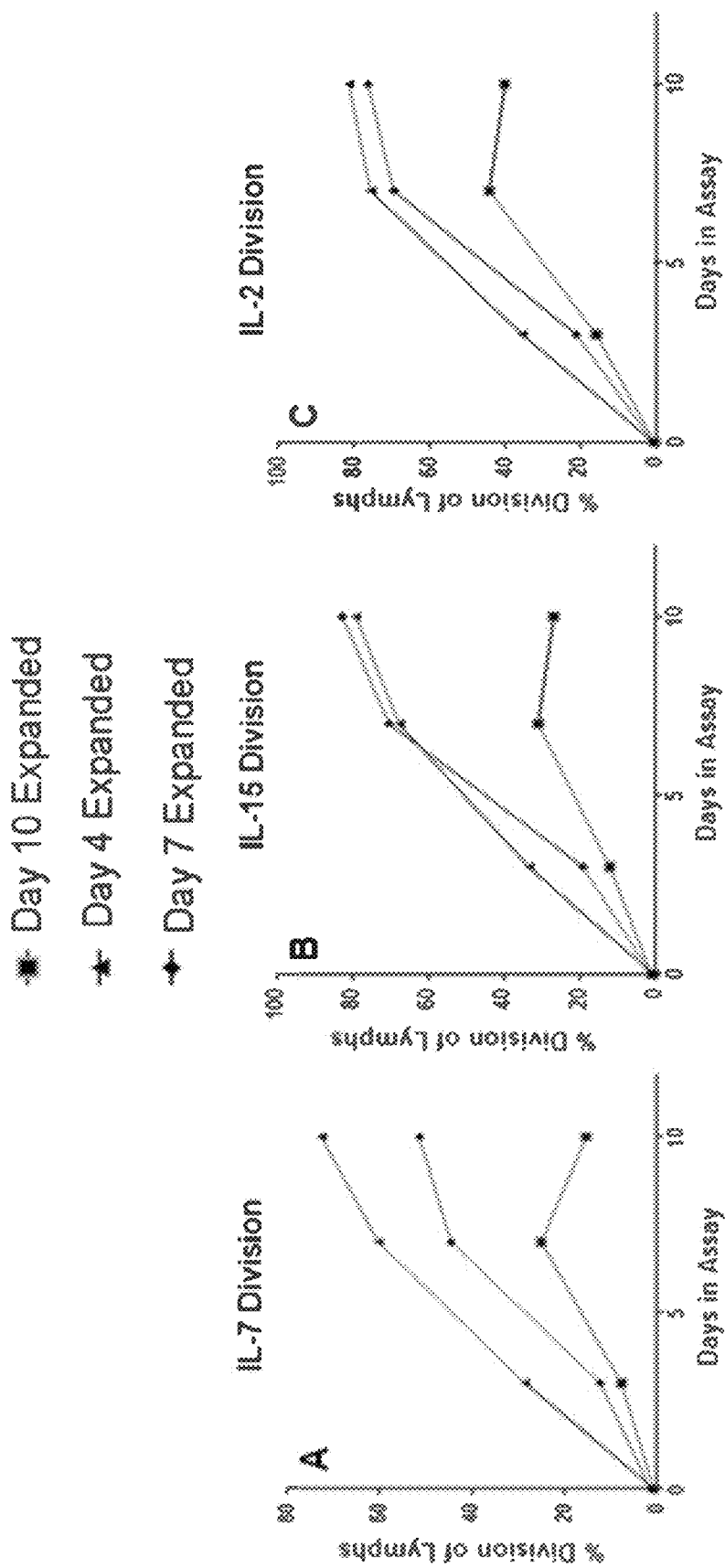
FIG. 13 shows shortened in vitro expansion of T cells correlates with increased cell division in the presence of (A) IL-7, (B) IL-15, and (C) IL-2.
Figure 14A:
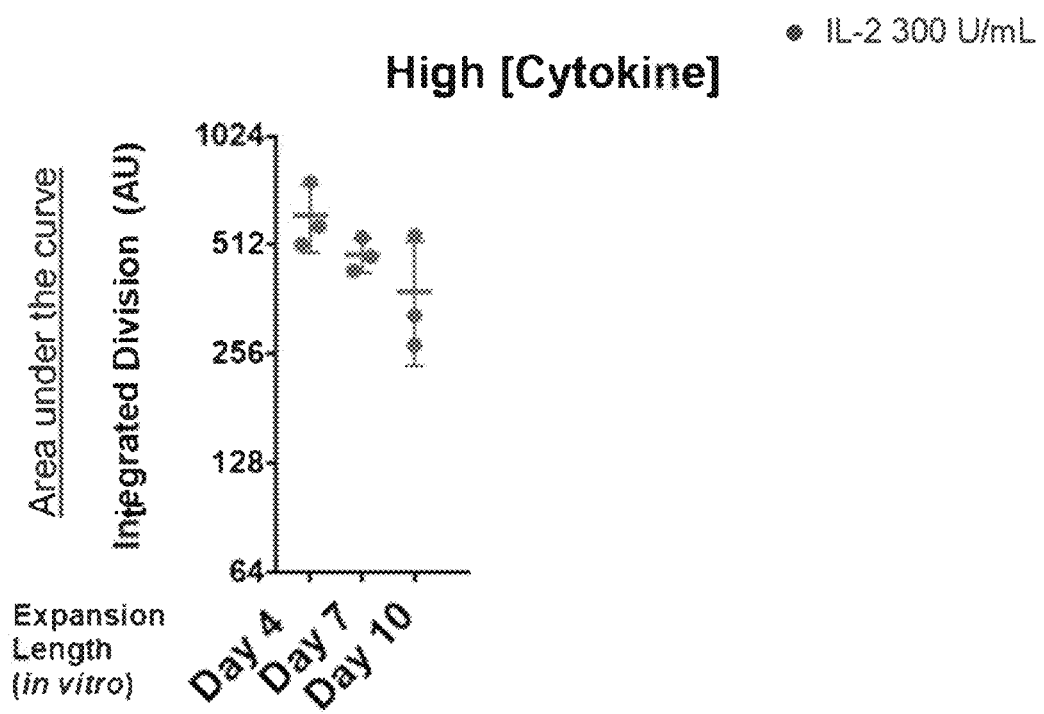
FIGS. 14A-14C show shortened in vitro expansion of transduced T cells correlates with increased cell division at higher cytokine concentrations. T-cells expanded for 4, 7, or 10 days were assessed via in the presence of 300 U/ml IL-2 (A), 10 ng/ml IL-7 (B), 10 ng/ml IL-15 (C), or over a period of 21 days with sampling every 2-3 days. Integrated division is calculated based on the percentage of lymphocytes, in which at detectable dilution of PkH67 was detected by day 10 in the assay. Each point represents three technical replicates of each donor with a total of 3 donors shown.
Figure 14B:
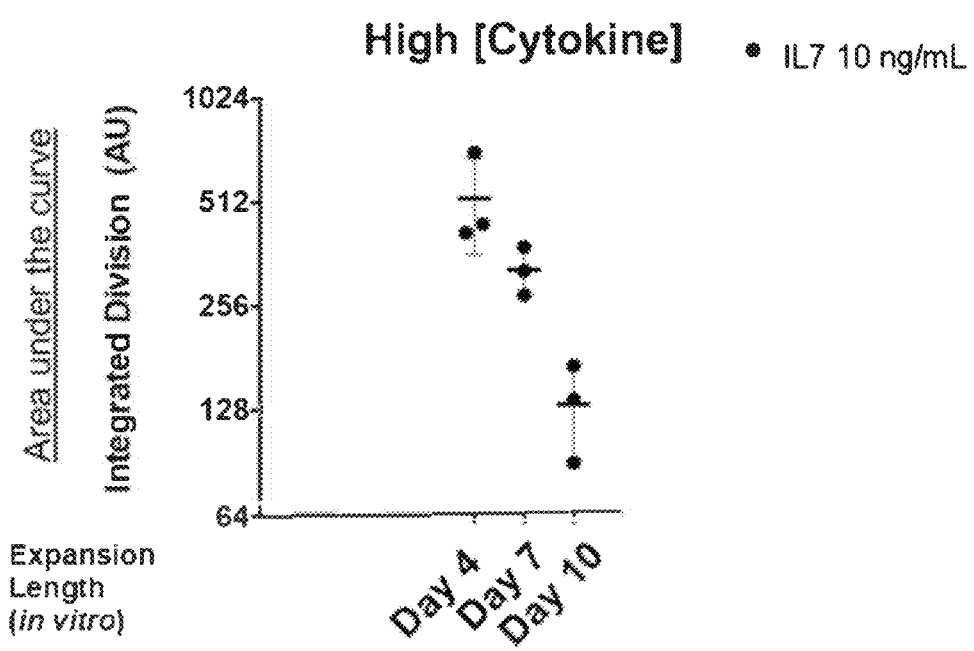
Figure 14C:
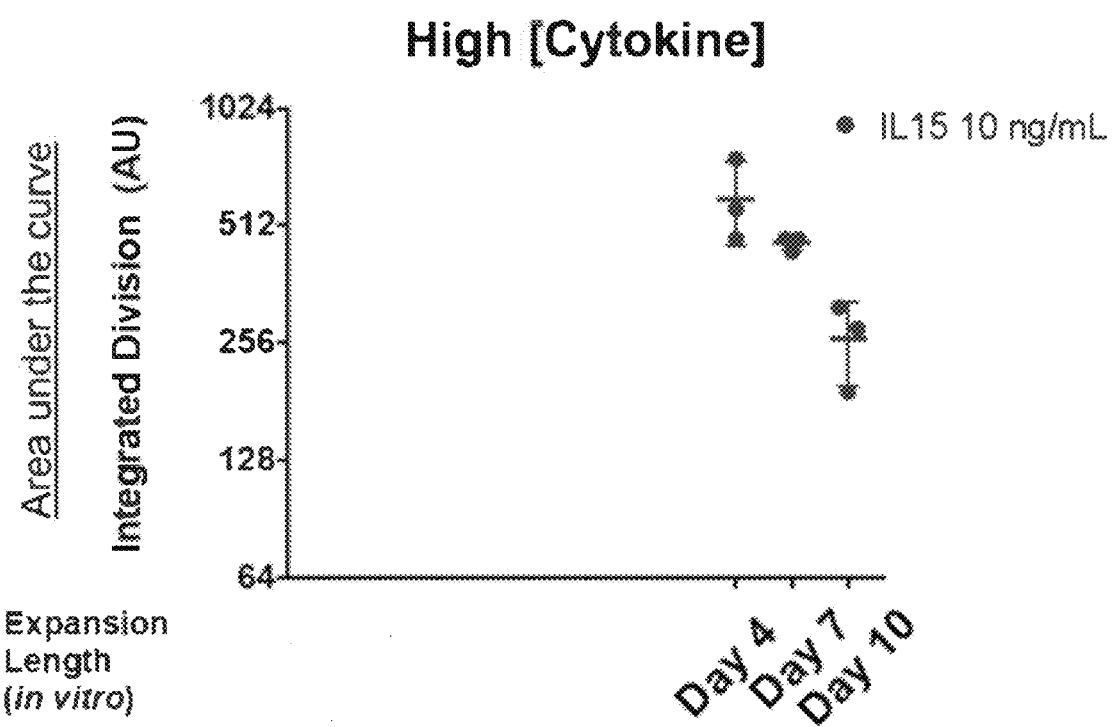

To determine effect of cytokine on cell division of expanded T cells, cell division of expanded T cells in the presence of IL-2, IL-7, or IL-15 was measured. FIG. 13 shows earlier expanded, e.g., Day 4, TCR-transduced T cells contain more dividing cells in the presence of (A) IL-7 (10 ng/ml), (B) IL-15 (10 ng/ml), and (C) IL-2 (300 IU/ml), as compared to those expanded for longer period of time, e.g., Day 7 and Day 10. Data is shown up to 10 days due to lack of cells in Day 10 cells after 10 days in assay. On Day 10 in the assay, more dividing cells of earlier expanded TCR-transduced T cells, e.g., Day 4 expanded, than those expanded for longer period of time, e.g., Day 7 and Day 10 expanded, in the presence of higher concentrations of cytokines, e.g., IL-2 (300 U/ml) (FIG. 14A), IL-7 (10.0 ng/ml) (FIG. 14B), or IL-15 (10.0 ng/ml) (FIG. 14C). The earlier expanded cells, e.g., Day 4, underwent division as calculated by the percentage of cells which diluted the proliferation dye at each time point across 10 days in the CSA. The analysis was done up to 10 days as the later expanded cells did not have enough cells for accurate analysis past day 10. For IL-2, there was an approximately 30% drop in the integrated division between day 4 and day 7 expanded cells and an approximately 50% drop between day 4 and day 10 expanded cells, p=0.0307. For IL-7, the same trend was seen with an approximately 40% drop between day 4 and day 7 expanded cells and with an approximately 80% drop between day 4 and day 10 expanded cells, p=0.0006. For IL-15, the same trend was observed with an approximately 20% drop between day 4 and day 7 expanded cells and with an approximately 40% drop between day 4 and day 10 expanded cells, p=0.0025.

Figure 15:
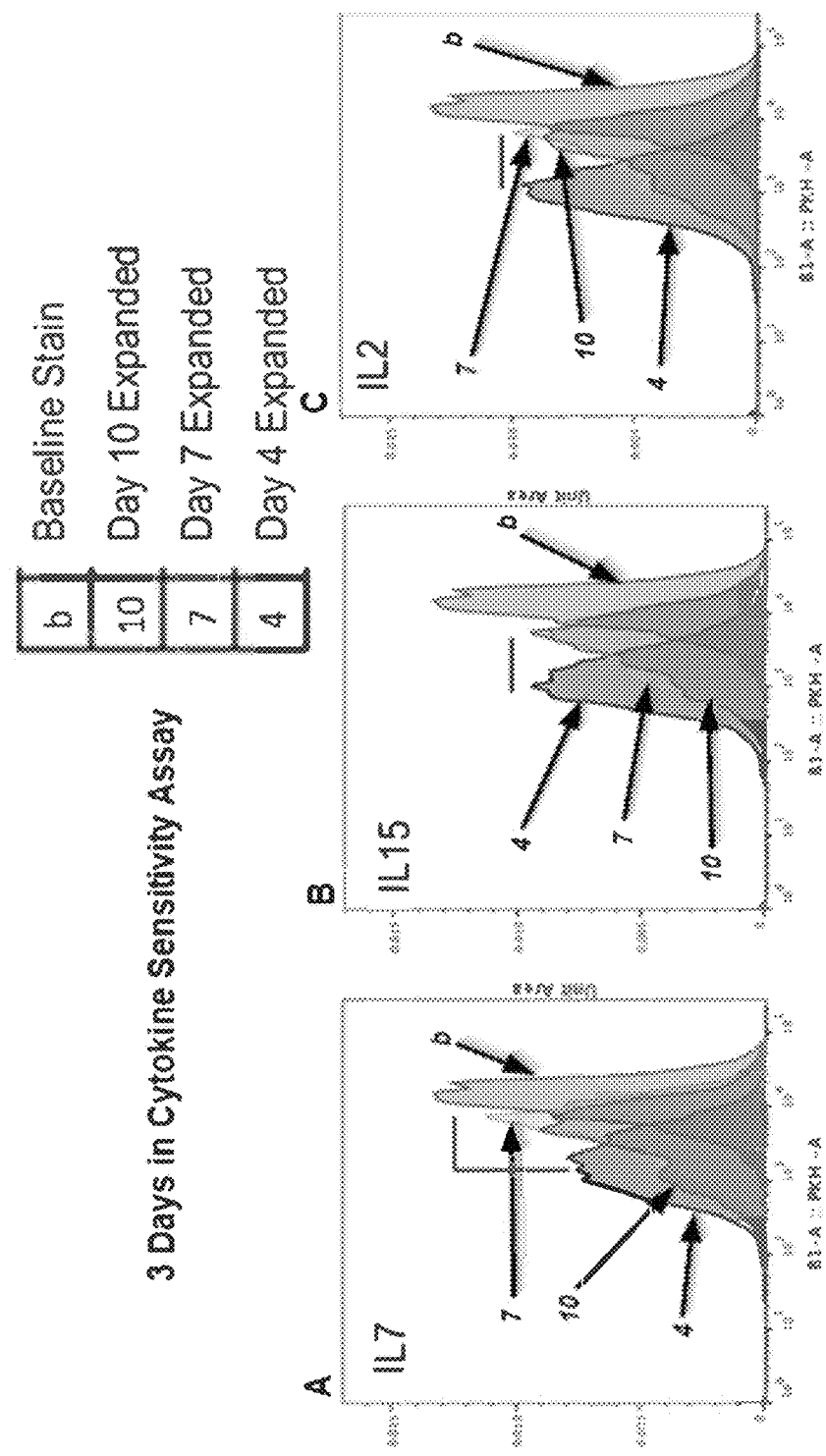
FIG. 15 shows shortened in vitro expansion of T cells correlates with increased sensitivity to (A) IL-7, (B) IL-15, and (C) IL-2.

Cytokine sensitivity may be determined by the levels of cell division induced by cytokines. To determine cytokine sensitivity of expanded T cells, integrated cell division of expanded T cells induced by IL-2, IL-7, or IL-15 was measured in cytokine non-limiting conditions, e.g., 3 days in assay. Integrated cell division may be calculated by performing an integration by calculating the area under the curve of the cell division over 3 days in assay. FIG. 15 show earlier expanded, e.g., Day 4, T cells contain more dividing cells in the presence of (A) IL-7 (10.0 ng/ml), (B) IL-15 (10.0 ng/ml), and (C) IL-2 (300 IU/ml) as compared to those expanded for longer period of times, e.g., Day 7 and Day 10. These results show shortened in vitro expansion of T cells respond to cytokines better than longer expanded T cells. Similarly, on Day 3 in assay, more dividing cells of earlier expanded T cells than those expanded for longer period of time in the presence of higher concentrations of cytokines, e.g., IL-2 (300 U/ml) (FIG. 16A), IL-7 (10.0 ng/ml) (FIG. 16B), or IL-15 (10.0 ng/ml) (FIG. 16C).

Example 6

Shortened In Vitro Expansion Correlates with Increased Cytokine Sensitivity

There was a strong correlation between the CD25 expression based on percentage of lymphocytes ($R^2$=0.82) or as the mean fluorescence intensity (MFI) of CD25 expression ($R^2$=0.89) and the response to IL2 induced survival of in the CSA. There was no correlation between the CD127 expression based on percentage of lymphocytes ($R^2$=0.04) the response to IL7 induced survival of in the CSA. Of interest, there was a moderate correlation between the MFI of CD127 expression ($R^2$=0.76) and IL7 induced survival. There was a weak correlation between the CD122 expression based on percentage of lymphocytes ($R^2$=0.42) or a moderate correlation as the MFI of CD122 expression ($R^2$=0.67) and the response to IL15 induced survival of in the CSA.

Figure 17:
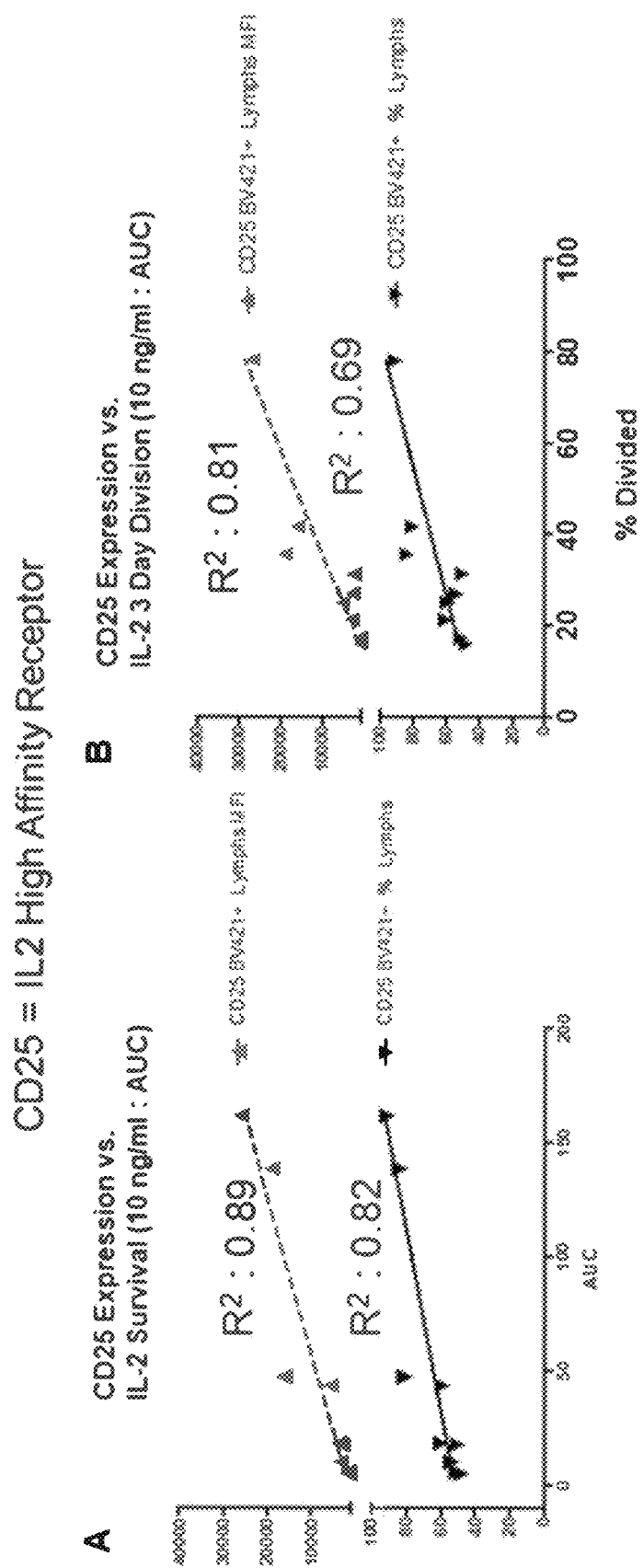
FIG. 17 shows correlation between IL-2 receptor (CD25) expression and survival/division in the presence of IL-2.

Cytokine sensitivity may also be determined by the expression levels of cytokine receptors that mediate cellular signaling pathways in the presence of cytokines. CSA measures the response to cytokine induced survival, proliferation, and apoptosis. These changes may correlate with the expression of the respective cytokine receptors within each T-cell population at the beginning of the assay. Thus, the expression of the defining subunit of the IL-2, IL-7, and IL-15 cytokine receptors, i.e., CD25, CD127, and CD122, respectively, were measured. Of note, CD122 is a shared subunit between the IL-2 and IL-15 receptors, though it is commonly assigned to be the reactive subunit of the IL-15 receptor. For example, FIG. 16D shows Day 4 expanded T cells, after 3 days in assay, express more IL-2 receptor (CD25) as compared to those expanded for a longer period of time, e.g., Day 7 and Day 10. FIG. 17 shows (A) this increased IL-2 receptor (CD25) expression, which was measured before Day 4 expanded TCR-transduced T cells were subject to assay, correlates well with increased IL-2-mediated cell survival, e.g., $R^2$=0.89 and 0.82. AUC stands for area under curve. FIG. 17 shows (B) this increased IL-2 receptor (CD25) expression also correlates well with increased IL-2-mediated cell division, e.g., $R^2$=0.81 and 0.69.

Figure 18:
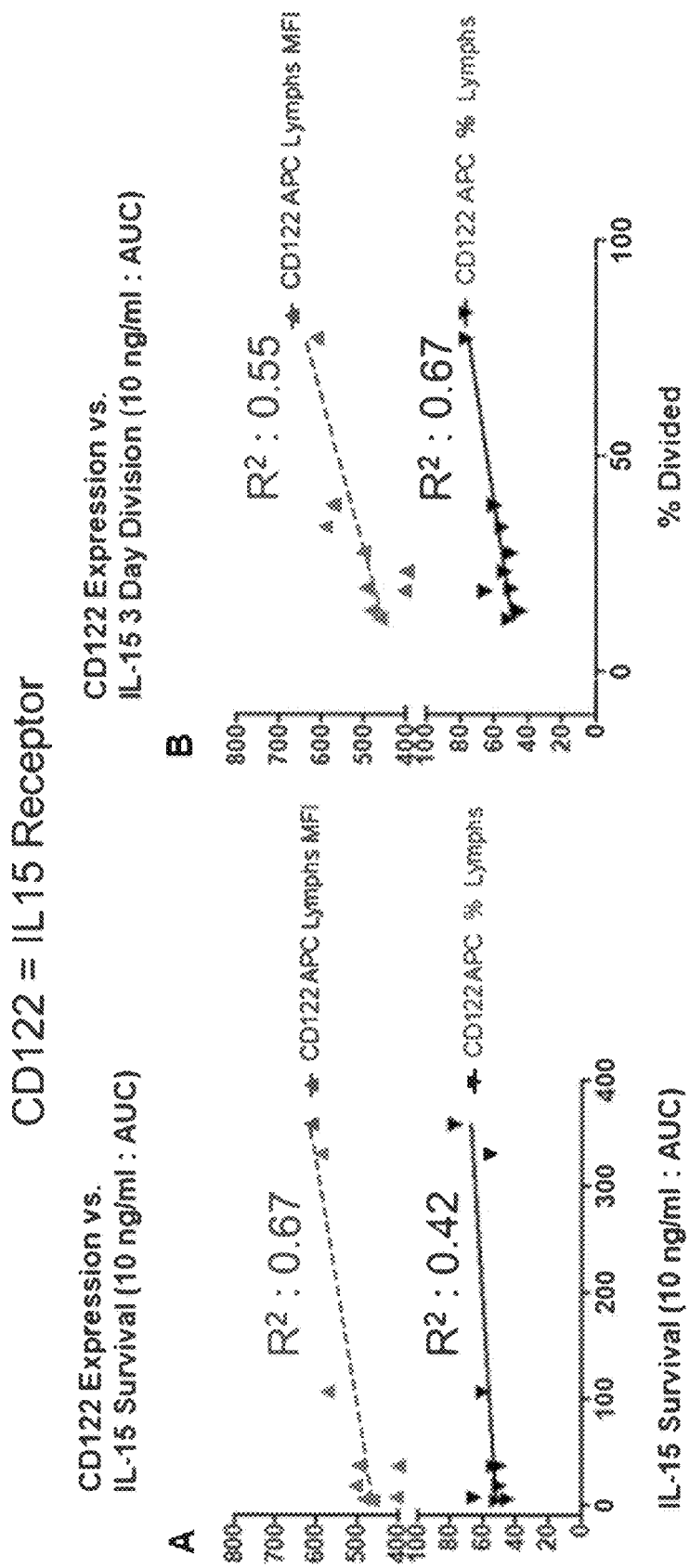
FIG. 18 shows correlation between IL-15 receptor (CD122) expression and survival/division in the presence of IL-15.

FIG. 18 shows (A) IL-15 receptor (CD122) expression, which was measured before Day 4 expanded TCR-transduced T cells were subject to assay, correlates modestly with increased IL-15-mediated cell survival, e.g., $R^2$=0.67 and 0.42, and (B) IL-15-mediated cell division, e.g., $R^2$=0.55 and 0.67.

Figure 19:
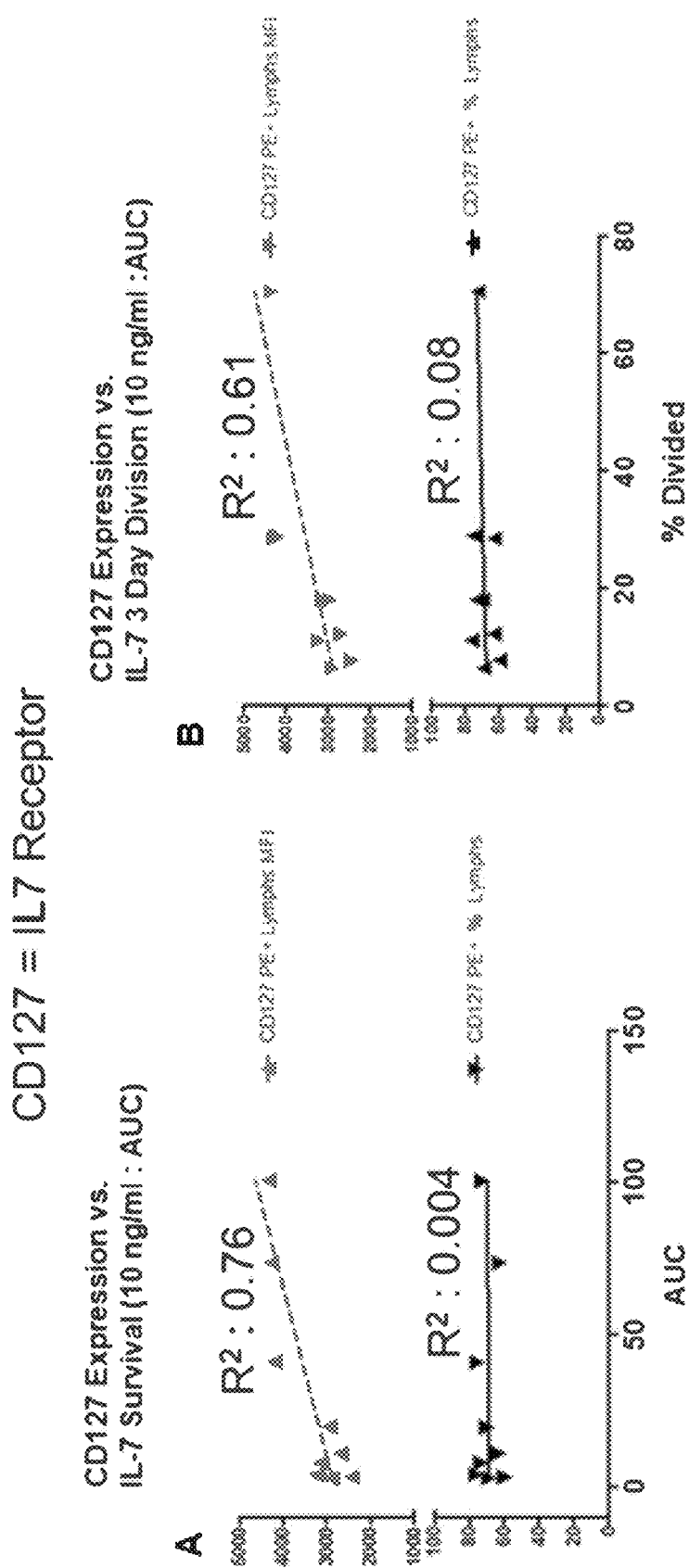
FIG. 19 shows correlation between IL-7 receptor (CD127) expression and survival/division in the presence of IL-7.

FIG. 19 shows (A) IL-7 receptor (CD127) expression, which was measured before Day 4 expanded TCR-transduced T cells were subject to assay, correlates poorly with increased IL-7-mediated cell survival, e.g., $R^2$=0.76 and 0.004, and (B) IL-7-mediated cell division, e.g., $R^2$=0.61 and 0.08.

Figure 20:
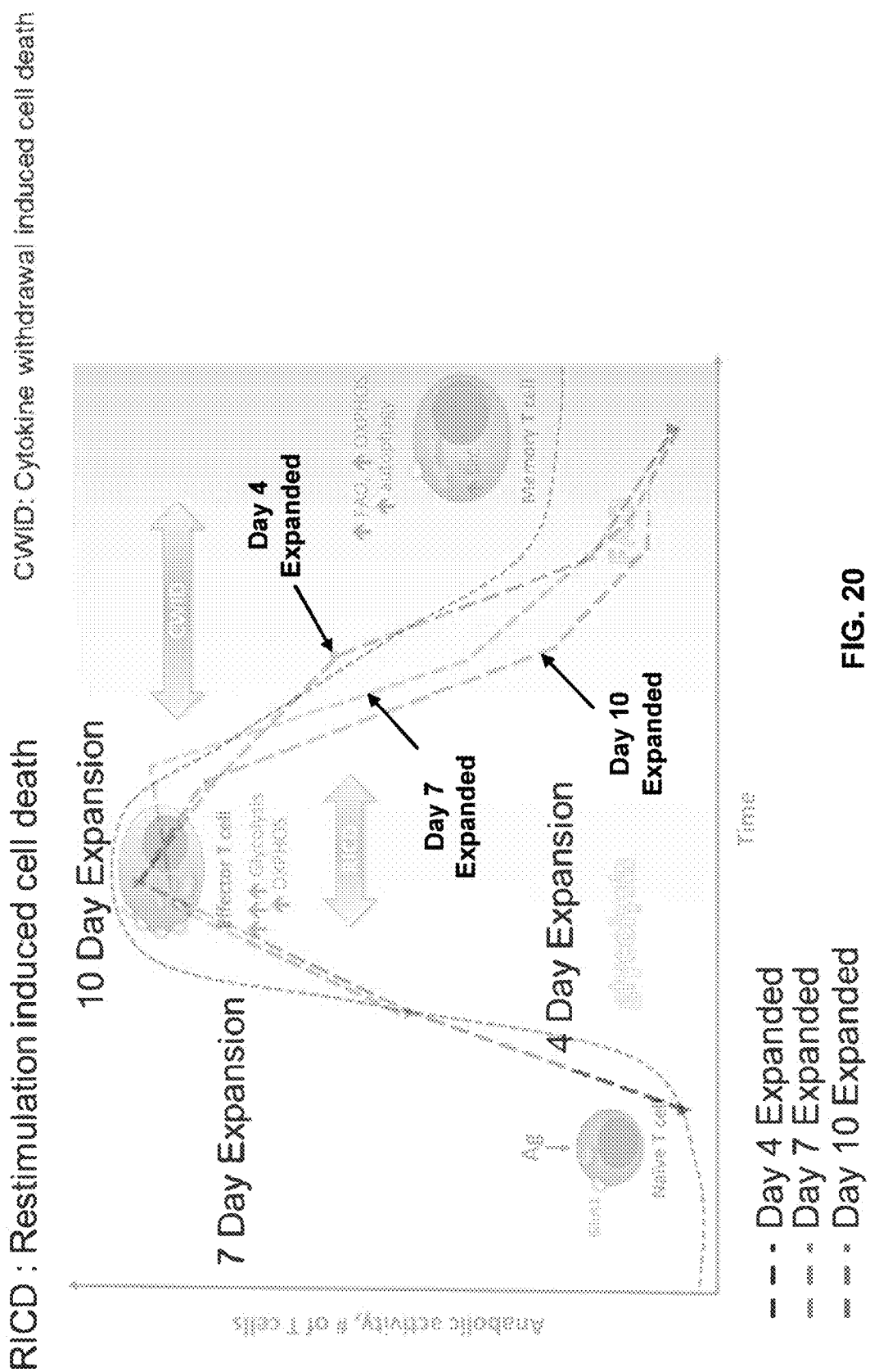
FIG. 20 shows shortened in vitro expansion of T cells retain T cell potentials. (Voss et al., *Cancer Letters* 408 (2017) 190-196, the content of which is hereby incorporated by reference in its entirety).

Results from these assays show that earlier manufactured (or minimally expanded) engineered T cells, for example about 3 to about 5 days, perform better as compared to longer expanded cells, for example, about 7 to about 10 days. For example, as shown in FIG. 20, minimally expanded, for example about 3 to about 5 days, engineered T cells may show greater clinical efficacy than that expanded for extended periods for example about 7 to about 10 days, in vitro, due to increased naivety, e.g., increased population of naïve T cells ($T_N$) and/or stem memory T cells ($T_{scm}$)/T central memory ($T_{cm}$), increased ability to proliferate, and increased persistence via, for example, decreasing apoptosis induced by CWID.

Example 7

Mechanism of Action (MOA) Phenotyping of Cells During CD3/CD28 Manufacturing

From the CSA results, the T cells appeared to be less functional in their ability to respond to proliferative cytokines, which may be partly due to the loss of cytokine receptor expression. These data suggest that a small fraction of the day 10 expanded T-cells may retain the ability to respond to cytokines. This observation suggests that T-cell population heterogeneity may be at play in the observed behavior. To investigate this diversity and the loss of potential, the effect of T-cell expansion on (1) final relative telomere length, (2) telomerase activity, (3) costimulatory molecule expression, and (4) whole RNA sequencing analysis were analyzed.

Telomere length reduction with elongated CD3/CD28 manufacturing

The loss of telomere length is a hallmark of dysfunctional cells as they become highly differentiated and eventually senescent. To investigate whether this effect was taking place in our differentially expanded T-cells, a fluorescence in situ hybridization assay was used to assess the relative telomere length (RTL) of the T-cells against an internal cell line control.

Figure 22:
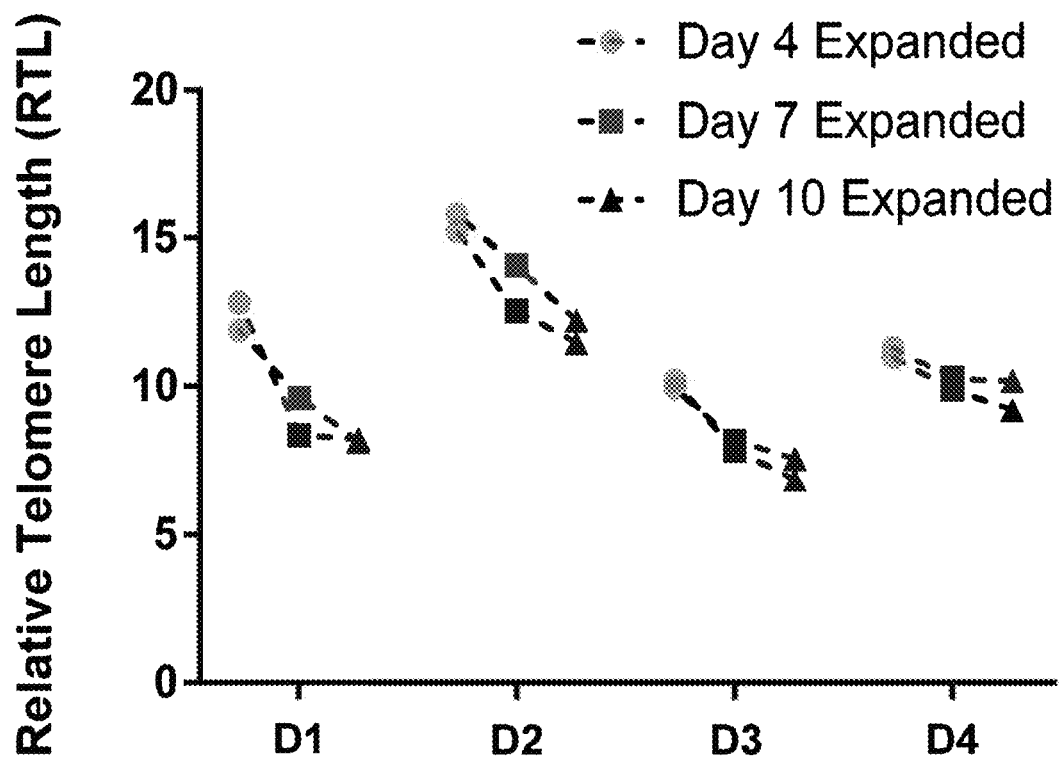
FIG. 22 shows continual loss of telomere length during CD3/CD28 T-cell expansion. The relative telomere length was assessed by fluorescence in situ hybridization relative to a tumor cell line control in 4 healthy donors (D1-D4). Each sample point represents a replicate of a technical duplicate. Donors' age: D1: 50 years old, D2: 31 years old, D3: 49 years old, and D4: 45 years old.

FIG. 22 shows, for all four donors (D1-D4) analyzed, there was a loss in RTL throughout the expansion protocol, with the day 4 expansion cells having the highest RTL. There was an approximate 20% loss in RTL between day 4 and day 7 expanded cells and an additional 10% loss in RTL between day 7 and day 10 expanded cells when all donors were grouped together. There were signs of an age bias in the data as well, with the younger donors, on average, having longer RTL compared to the older donors when compared at the day 10 expanded time-point. Donors' age: D1: 50 years old, D2: 31 years old, D3: 49 years old, and D4: 45 years old.

Reduced telomerase activity during elongated CD3/CD28 manufacturing

Based on the reduction in telomere length and heterogeneity in telomerase induction following CD3+CD28 stimulation, the levels of active telomerase were determined via an enzyme linked immunosorbent assay (ELISA).

Figure 23:
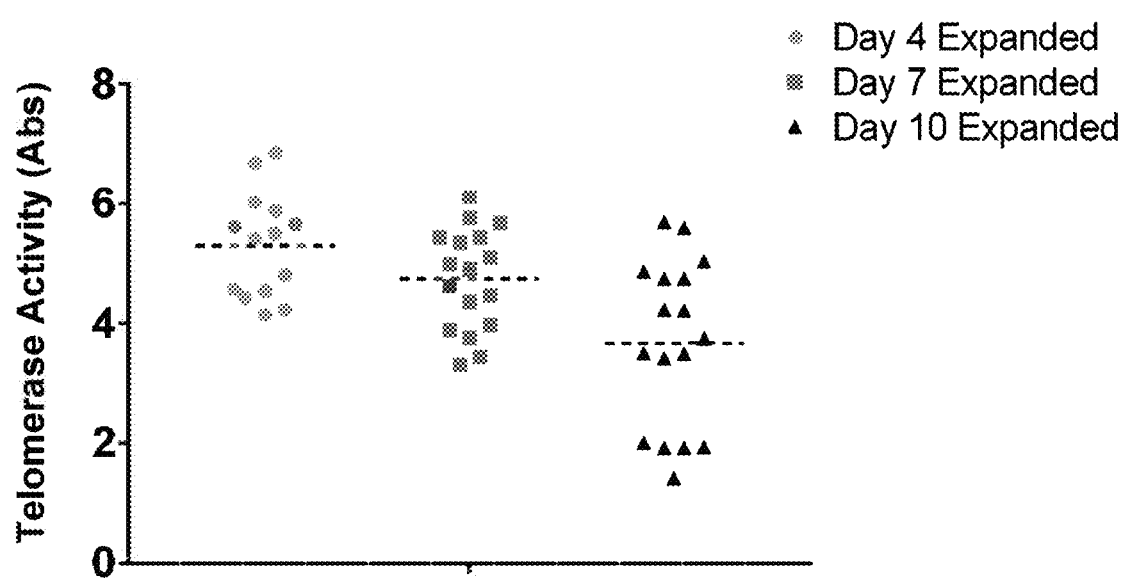
FIG. 23 shows reduced telomerase activity with prolonged CD3/CD28 T-cell expansion. Telomerase activity was measured via an ELISA based colorimetric assay from whole cell lysate of cells taken from day 4, 7, or 10 in T-cell expansion. Each point represents a technical triplicate sample from a total of 5 biological replicates.

FIG. 23 shows there was a statistically insignificant reduction (approximately 10%) between day 4 and day 7 expanded cultures. In contrast, there was a 40% reduction in activity between day 4 and day 10 expanded cells which was statistically significant ($p=0.0004$) and an approximately 25% reduction between day 7 and day 10, which was also statistically significant ($p=0.0165$). Taken together, there is an expansion correlated loss in both the RTL and the final levels of active telomerase with the prolonged expansions produced cells, which may be less fit for additional expansions.

Loss of T-cell early memory phenotypes during CD3/CD28 manufacturing

The CSA results show there may be a distinct difference in the starting memory compartments between the differentially expanded cells. A higher resolution analysis was performed on the starting memory compartment to detect the differences between the differentially expanded samples.

Figure 24:
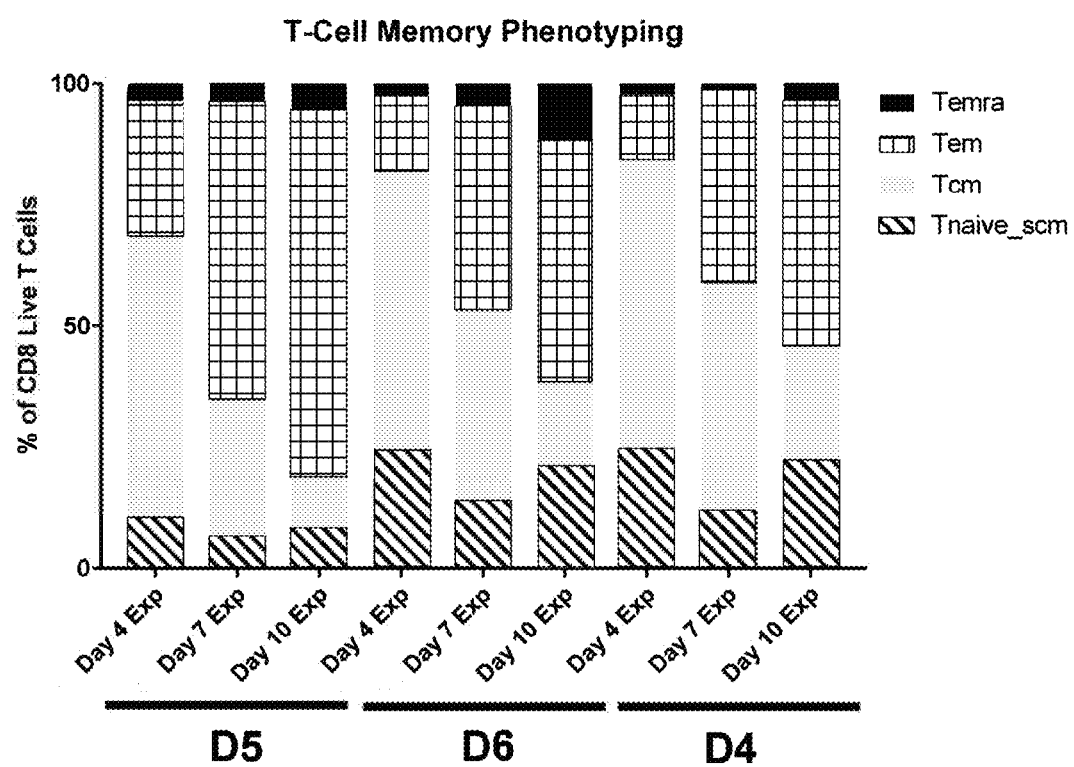
FIG. 24 shows T-cell differentiation during CD3/CD28 Manufacturing from three biological donors D4, D5, and D6. Representative PBMCs were cultured and then phenotyped by flow cytometry at the indicated expansion day. Memory phenotypes are defined based on CD45RO and CCR7 expression, $T_{naive}/s_{cm}$=CD45RO−CCR7+, $T_{cm}$=CD45RO+CCR7+, $T_{em}$=CD45RO+CCR7−, and $T_{emra}$=CD45RO−CCR7−.

FIG. 24 shows there was a small statistically insignificant difference in the $T_{naive/scm}$ compartment between day 4, 7, and 10 (mean values of 20.03%, 11.1%, 17.47% of CD8 cells). There was, however, a statistically significant difference ($p<0.05$) within the Tcm compartment between day 4, 7, and 10 expanded cells (mean values 58.27, 37.73, 16.8% of CD8 cells). There was a statistically significant difference ($p<0.05$) within the $T_{em}$ compartment between day 4, 7, and 10 expanded cells (mean values of 18.9, 48.13, and 58.9% of CD8 cells). There was a small statistically insignificant difference within the $T_{emra}$ compartment between day 4, 7, and 10 expanded cells (mean values of 2.70, 3.06, and 6.80% of CD8 cells). These results show the major memory compartment differences may be in the $T_{cm}$ to $T_{em}$ transition, with later expanded cells containing fewer $T_{cm}$ and more $T_{em}$ T cells.

Loss of CD28 and CD27 expression during CD3/CD28 manufacturing

In addition to the conventional memory compartments, cells were phenotyped for expression of costimulatory markers CD28 and CD27, both of which are known to be associated with increased T-cell persistence in vivo.

Figure 25:
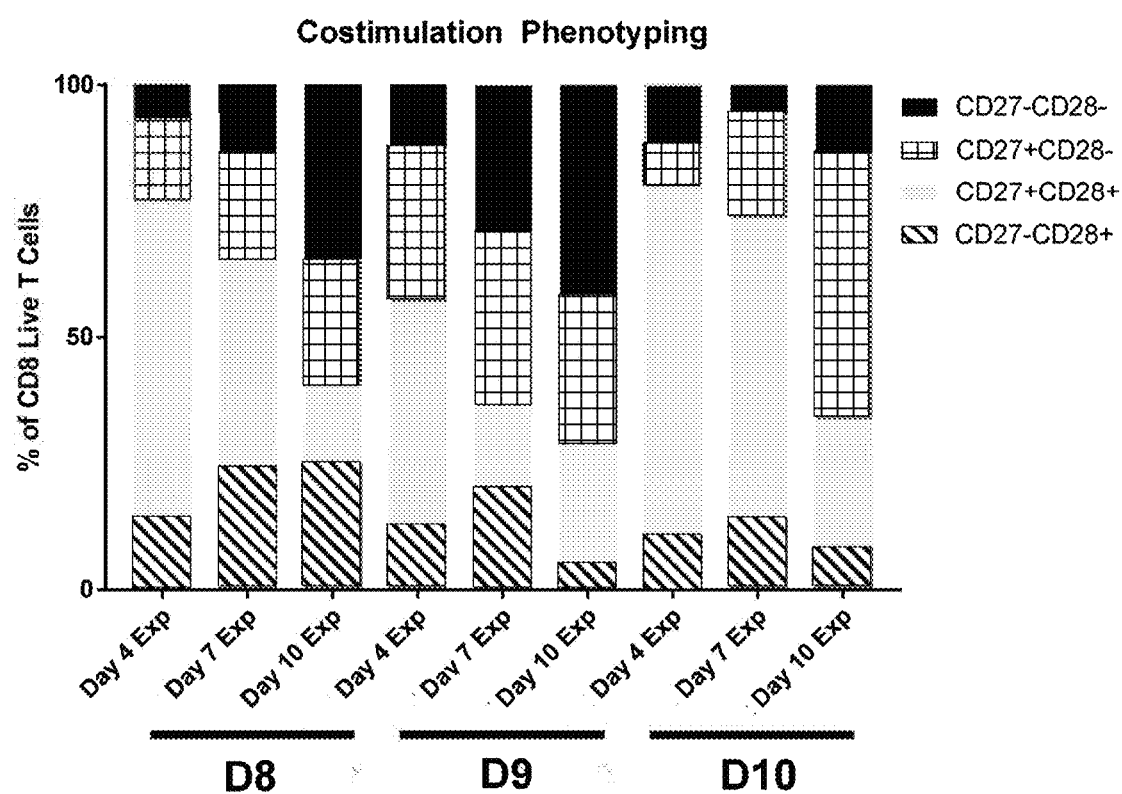
FIG. 25 shows loss of costimulation during CD3/CD28 manufacturing from three biological donors D1, D7, and D8. CD27 and CD28 expression was assessed via flow cytometry on day 4, 7, and 10 during the T-cell expansion period.

FIG. 25 shows, during CD3+CD28 expansion, there was a stepwise loss of both CD28 and CD27, with the most drastic loss by day 10 in the manufacturing period. While none of the comparisons between day 4, 7, and 10 expanded cultures yielded statistical significance ($p<0.05$), there were trends towards significance ($p=0.0520$) within the CD27+ CD28+ compartment between the day 4 and day 10 expanded cultures (mean values of 58.47 and 21.43% of CD8 cells). Additionally, there was an enrichment ($p=0.1581$) in the double negative CD27-CD28- compartment between day 4 and day 10 expanded cells (mean values 10.24% and 29.77% of CD8 cells).

Differential gene expression analysis identifies clusters the earlier expanded cells as a unique cluster compared to later expanded cells While the data suggest a phenotypic difference between the differentially expanded T cells, the explorations may be limited to the number of designated targets investigated (e.g. CD28 or T-cell memory compartments). To widen the scope of the phenotyping studies, whole RNA sequencing was performed from three biological donors expanded for 4, 7, or 10 days.

Figure 26:
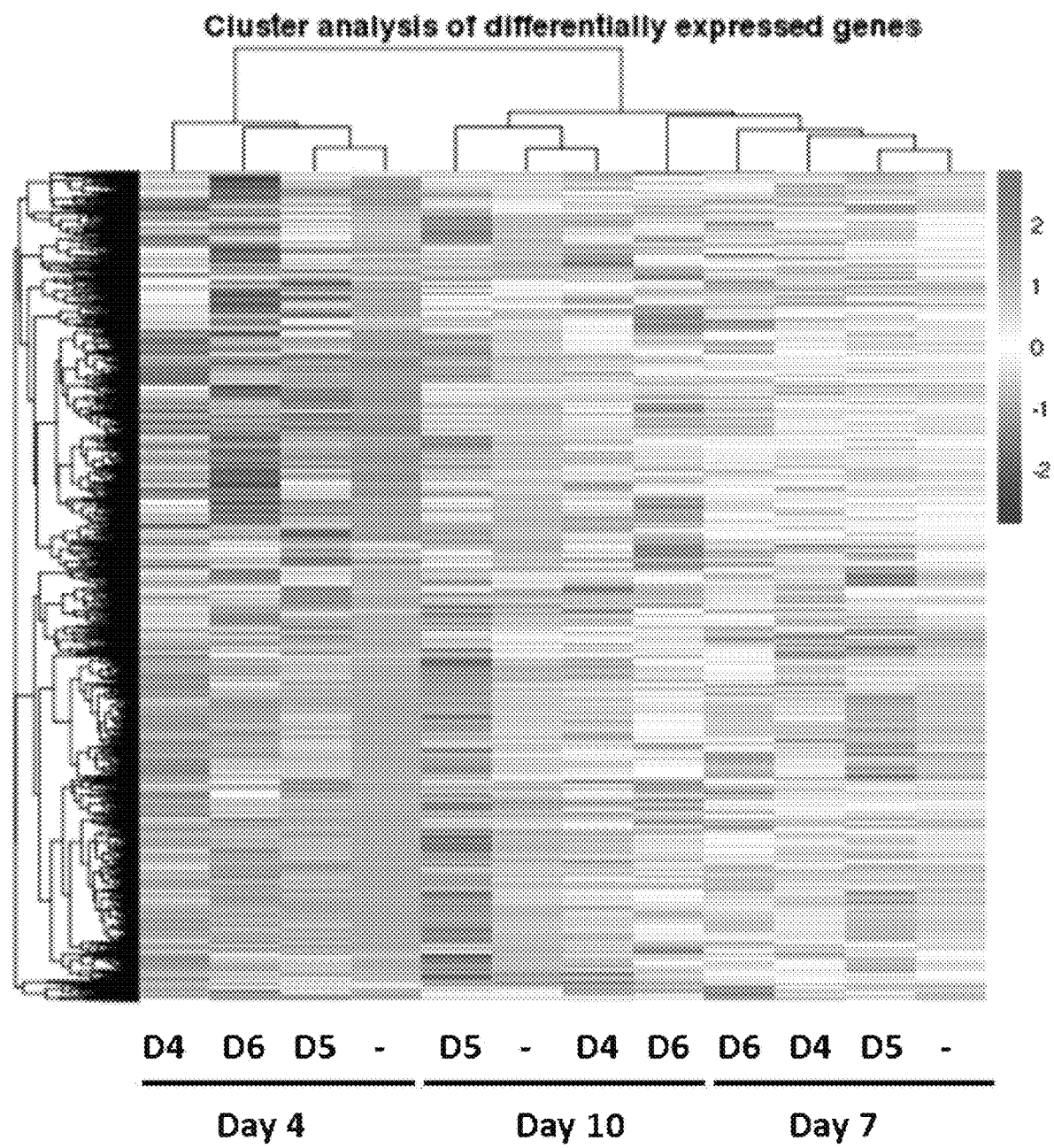
FIG. 26 shows differential gene expression analysis identifying clusters of the earlier expanded cells as a unique cluster compared to later expanded cells. Three biological donors (D4, D5, and D6) were expanded for 4, 7, or 10 days and then whole RNA was isolated and sent to Novogene for RNA sequencing analysis and bioinformatics.

FIG. 26 shows, based on cluster analysis, distinct grouping of the day 4 expanded cells compared to the day 7, which appeared in an intermediary cluster, while the day 10 cells appeared in a unique cluster of their own. These results show there is a distinctly different clustering patter of the day 4 expanded cells as compared to the day 7 and day 10 expanded cells. This data supports a linear differentiation model of T-cell expansion in which gradual changes at the RNA level take place throughout the expansion protocols.

Earlier expanded cells show an increased number of differentially expressed genes as compared to the later expanded samples The whole RNA sequencing was analyzed for differentially expressed genes (DEGs) between the day 4, 7, and 10 expanded cells across three biological donors.

Figure 27:
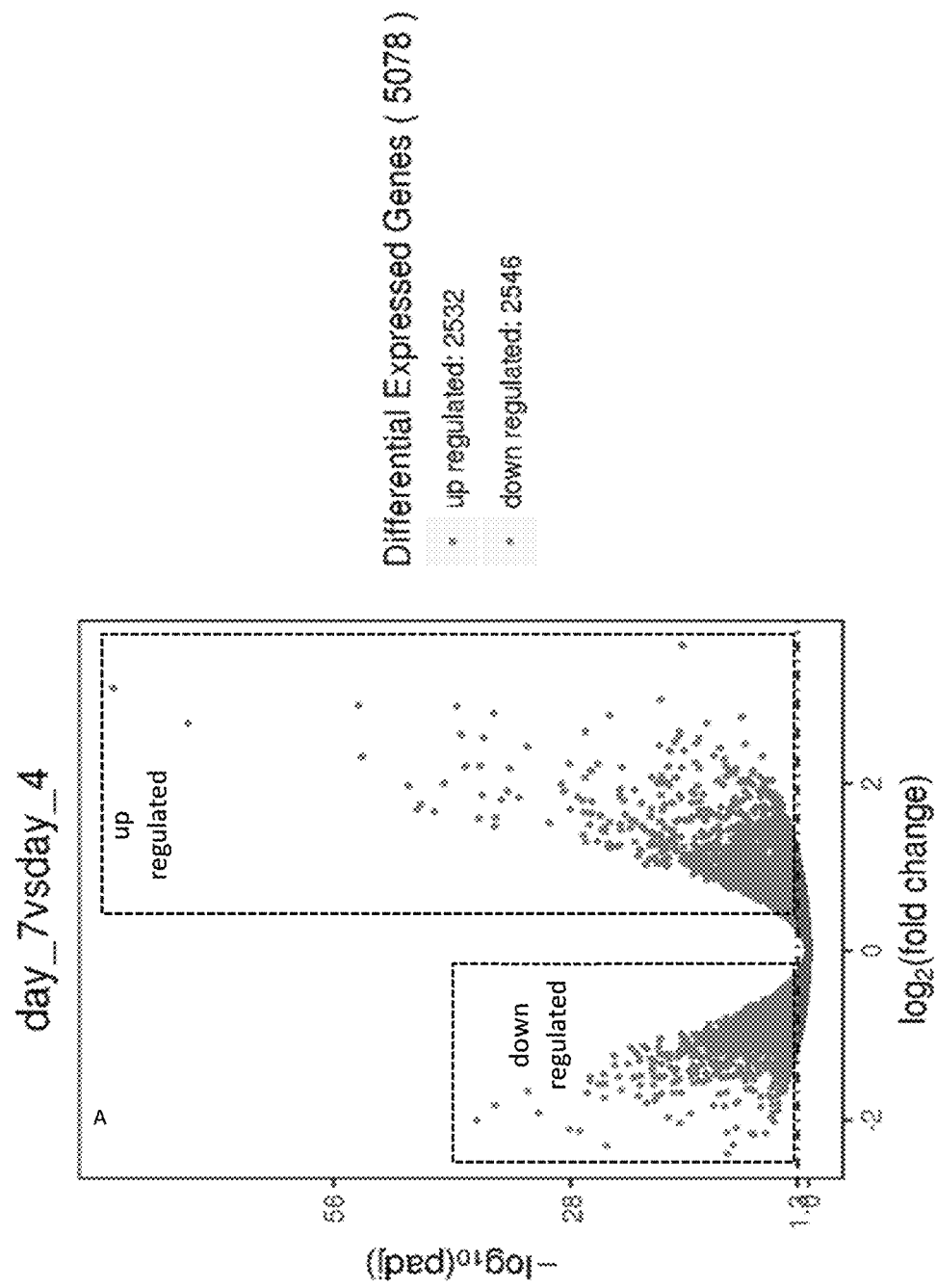
FIG. 27 shows RNAseq analysis during T-cell manufacturing. Volcano plot representation of RNAseq data during T-cell manufacturing comparing (A) day 4 vs day 7, (B) day 4 vs day 10, and (C) day 7 vs day 10. DEGs cut-off was set to 1-fold up or down with a padj-value of less than 0.05. Number of DEGs is shown in the key for each plot.
Figure 27:
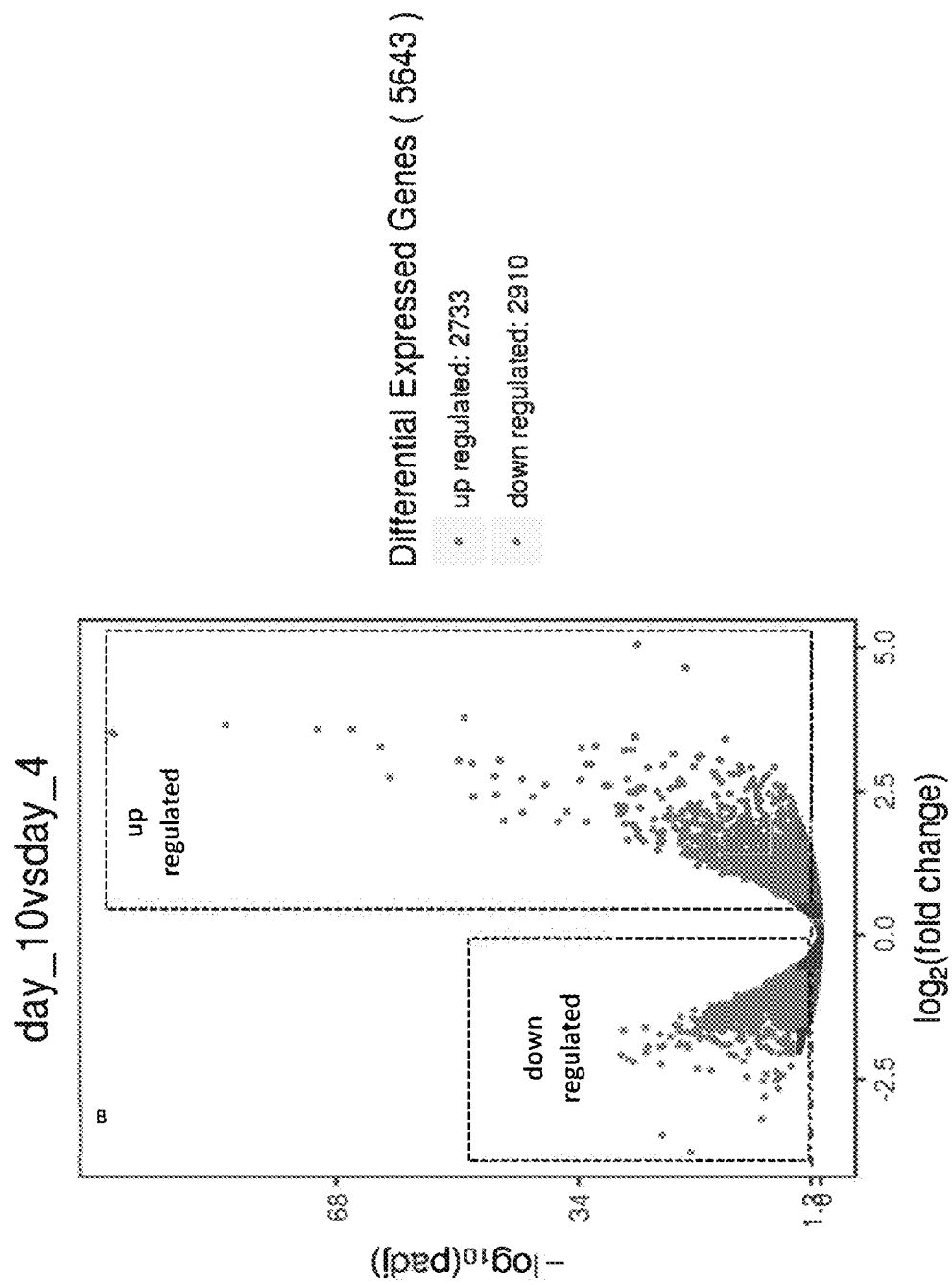
Figure 27:
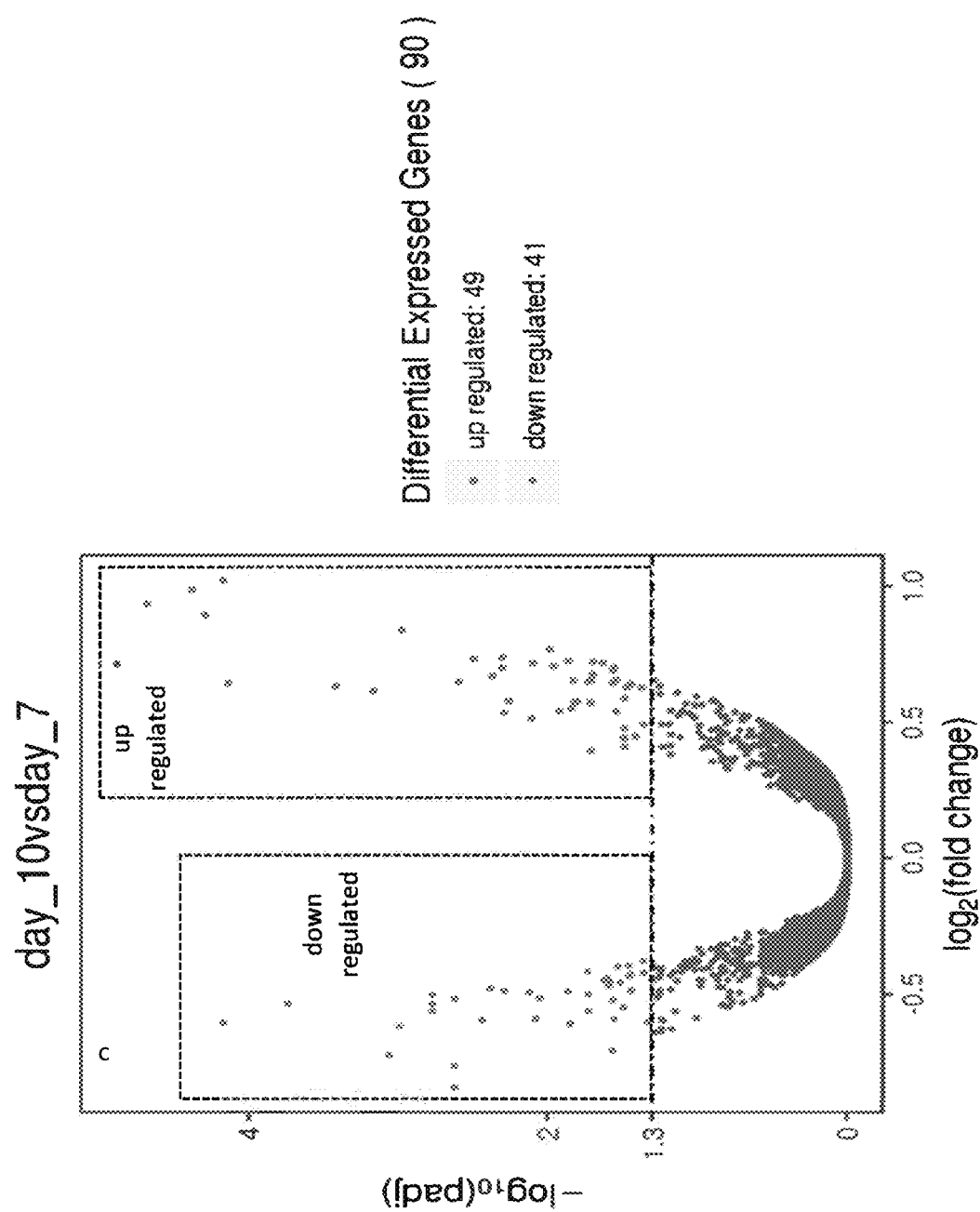

FIG. 27 shows the gene expression profiles changed in the most early in the manufacturing process as evident by the 5,078 DEGs in the day 4 vs day 7 comparison and the 5,643 DEGs in the day 4 vs day 10 comparison. With respect to both sets, there was a roughly equal distribution of up and down regulated genes. In contrast, there was relatively few DEGs when comparing the day 7 vs day 10 manufactured cells, with 90 genes identified, with an equal split between up and down regulated genes.

Kyoto Encyclopedia of Genes and Genomes (KEGG) analysis highlights loss of cell cycle associated genes and an upregulation of apoptosis associated genes throughout manufacturing In order to better understand the dramatic gene expression changes occurring during manufacturing, KEGG pathway analysis was performed to identify gene pathways that were over-represented in the differing gene sets. KEGG pathways may be related to T-cell proliferation and persistence based on the functionality results obtained from the CSA, e.g., survival, division, and apoptosis.

FIG. 28 shows, comparing with the later time points to day 4 in manufacturing, there is a significant down regulation in DNA replication and cell cycle gene pathways. Compounding this effect, there was a significant up regulation in apoptosis, p53 signalling gene pathways during the same period in manufacturing. In agreement with the gene expression results in FIG. 27, there were very few significantly enriched pathways between day 7 and day 10 in manufacturing.

Example 8

Methods

T-Cell Manufacturing

Healthy donor whole blood was purchased from Hemacare and PBMCs were isolated by Ficoll gradient. PBMCs were activated for 16-24 hours in TexMACS (Miltenyi 130-097-196) supplemented with 5% Human AB serum (Gemini 100-318) media by plating at $1 \times 10^6$ live PBMC/ml on tissue culture flasks coated overnight with 1 ug/ml anti-CD3 (eBioscience 16-0037-85) and 1 ug/ml anti-CD28 (eBioscience 16-0289-85) antibody in PBS (Lonza 17-516F) at 4 degrees Celsius. The next day, total cells were isolated and resuspended to $1 \times 10^6$ live-cell/ml and 5 mls were plated into a well of a Grex24 well plate (Wilson Wolf 80192M). Cells were either mock transduced or transduced with a TCR lentiviral construct (produced by Lentigen) in the presence of 10 ng/ml IL-7 (peprotech 200-07), 100 ng/ml IL-15 (peprotech 200-15), and 10 μg/ml protamine sulfate. The next day, cells were fed with 35 mL of complete TexMACS supplemented with IL-7 and IL-15 at above mentioned concentrations. Cells were grown for an additional 2, 5, or 8 days depending on the desired manufacturing time (4, 7, or 10 total days). After manufacturing, cells were counted and frozen down at $5 \times 10^6$/ml in Cyrostore10, placed at −80 degrees Celsius for 16-24 hours and then stored long-term at LN2 vapor phase until needed.

PkH67 Stain

Cell division may be measured by the dilution of proliferation dye PkH67. PkH67 (Sigma PKH67GL) stain was performed per manufacturer's protocol with the exception that the day 4 manufactured cells were stained at a 2× concentration to account for the larger cell size compared to day 7 or day 10 manufactured cells. PkH staining was performed before the flow cytometry viability dye stain.

Cytokine Sensitivity Assay (CSA)

T-cell products were thawed and rested for approximately four hours in TexMACS supplemented with 5% Human AB serum and 100 U/mL Benzonase (Sigma E10114) at 1-2× $10^6$/ml. Following resting period, cells were labeled with PkH and $2 \times 10^5$ lymphocytes were cultured in a Grex24 well flask with a titration of IL-7, IL-15, or IL-2 (R&D Systems 202-IL) for a total of 21 days. During this time, cells were counted by volumetric flow cytometry every three to four days and phenotyped with memory T-cell panel every seven days. Cytokines were replenished every seven days to the starting concentration.

Flow Cytometry Stain and Acquisition

Live cells were quantified and resuspended to 1-2×$10^6$ live-cell/ml in PBS then stained with Live-Dead stain according to manufacturer's protocol. Cells were then washed with Flow buffer and then resuspended at desired antibody concentrations as indicated in the tables below and stained for 15-30 minutes in the dark at 4 degrees Celsius, with the exception that the CCR7 stain was done at 37 degrees Celsius in RPMI (Gibco 11835-030) without serum. Cells were then washed in Flow buffer and resuspended in fixation buffer and stored at 4 degrees Celsius until acquired on the BD Fortessa or Miltenyi MACSQuant analyzer. The following tables contain the reagents used for all flow cytometry straining.

| Memory T - Cell Panel for Cytokine Sensitivity Assay | | | | | |
|---|---|---|---|---|---|
| Fluorochrome | Antigen | Clone | Dilution | Provider | Catalog Number |
| AX488 | PkH | N/A | N/A | Sigma | PKH67GL-1KT |
| PerCP-Cy5.5 | CD3 | HIT3a | 80 | BioLegend | 300328 |
| PE | Vb8 | JR2 | 80 | BioLegend | 348104 |
| PE-Cy7 | CD45Ro | UCHL1 | 80 | BioLegend | 304230 |
| APC-fire750 | CD95 | DX2 | 80 | BioLegend | 305638 |
| BV421 | CCR7 | G043H7 | 80 | BioLegend | 353208 |
| Aqua | Live/dead | NA | 400 | Thermo fischer | L34957 |
| BV605 | CD8 | SK1 | 80 | BD Horizon | 564116 |
| BV650 | CD27 | O323 | 80 | BioLegend | 302827 |
| BV785 | CD62L | DREG56 | 80 | BioLegend | 304830 |

| Cytokine Receptor T - Cell Panel for Cytokine Sensitivity Assay | | | | | |
|---|---|---|---|---|---|
| Fluorochrome | Antigen | Clone | Dilution | Provider | Catalog Number |
| AX488 | Vb8 | JR2 | 80 | BD BioScience | 555606 |
| PE | CD127 | A019D5 | 80 | BioLegend | 351304 |
| APC | CD122 | TU27 | 80 | BioLegend | 339008 |
| BV421 | CD25 | G043H7 | 80 | BD Horizon | 562442 |
| BV605 | CD8 | SK1 | 80 | BD Horizon | 564116 |

| Costimulation Phenotyping Panel | | | | | |
|---|---|---|---|---|---|
| Fluorochrome | Antigen | Clone | Dilution | Provider | Catalog Number |
| PerCP-Cy5.5 | CD3 | HIT3a | 80 | BioLegend | 300328 |
| PE | CD127 | A019D5 | 80 | BioLegend | 351304 |
| PE-Cy7 | CD57 | HNK-1 | 80 | BioLegend | 359623 |
| APC | CD122 | TU27 | 80 | BioLegend | 339008 |
| APC-fire750 | CD8 | Sk1 | 80 | BD Pharmingen | 560179 |

Costimulation Phenotyping Panel

| Fluorochrome | Antigen | Clone | Dilution | Provider | Catalog Number |
|---|---|---|---|---|---|
| BV421 | CCR7 | G043H7 | 80 | BioLegend | 353208 |
| Aqua | Live/dead | | 400 | Thermo Fisher | L34957 |
| Bright 600 | KLRG1 | 13F12F2 | 80 | BioLegend | 138419 |
| BV650 | CD27 | O323 | 80 | BioLegend | 302827 |
| BV785 | CD28 | CD28.2 | 80 | BioLegend | 302949 |

Telomere Length Determination

Relative telomere length was determined according to manufacturer's instructions (Dako/Agilent K5327). Briefly, T-cells were mixed at a 1:1 ratio with control 1301 tumor cells (4N genome). Cells were then permeabilized and a Telomere PNA FITC probe was hybridized overnight. The next day, a counter propidium iodide stain was performed to discriminate intact cells and the cells were acquired by flow cytometry. The telomere length of the test cells was calculated as a ratio to that of the control 1301 tumor cell line.

CDR3 Sequencing (Adaptive Biotech) and Analysis of T-Cell Receptor Variable Beta Chain Sequencing Immunosequencing of the CDR3 regions of human TCRβ chains was performed using the immunoSEQ® Assay (Adaptive Biotechnologies, Seattle, Wash.). Extracted genomic DNA was amplified in a bias-controlled multiplex PCR, followed by high-throughput sequencing. Sequences were collapsed and filtered in order to identify and quantitate the absolute abundance of each unique TCR8 CDR3 region for further analysis.

Statistical Analyses of TCR-β Sequencing Results

Clonality was defined as 1-Peilou's eveness and was calculated on productive rearrangements by:

$$1 + \frac{\sum_{i}^{N} p_i \log_2(p_i)}{\log_2(N)}$$

where pi is the proportional abundance of rearrangement i and N is the total number of rearrangements. Clonality values range from 0 to 1 and describe the shape of the frequency distribution: clonality values approaching 0 indicate a very even distribution of frequencies, whereas values approaching 1 indicate an increasingly asymmetric distribution in which a few clones are present at high frequencies. Statistical analysis was performed in R version 3.2.

RNAseq (Novogene) Data Analysis

Downstream analysis was performed using a combination of programs including STAR, HTseq, Cufflink and our wrapped scripts. Alignments were parsed using Tophat program and differential expressions were determined through DESeq2/edgeR. GO and KEGG enrichment were implemented by the ClusterProfiler. Gene fusion and difference of alternative splicing event were detected by Star-fusion and rMATS software.

RNAseq (Novogene) Reads Mapping to the Reference Genome

Reference genome and gene model annotation files were downloaded from genome website browser (NCBI/UCSC/Ensembl) directly. Indexes of the reference genome was built using STAR and paired-end clean reads were aligned to the reference genome using STAR (v2.5). STAR used the method of Maximal Mappable Prefix(MMP), which can generate a precise mapping result for junction reads.

RNAseq (Novogene) Quantification of Gene Expression Level

HTSeq v0.6.1 was used to count the read numbers mapped of each gene. FPKM of each gene was then calculated based on the length of the gene and reads count mapped to this gene. FPKM, Reads Per Kilobase of exon model per Million mapped reads, accounts for the effect of sequencing depth and gene length for the reads count at the same time, and is commonly used method for estimating gene expression levels.

RNAseq (Novogene) Differential Expression Analysis

For DESeq2 with biological replicates, differential expression analysis between two conditions/groups (two biological replicates per condition) was performed using the DESeq2 R package (2_1.6.3). DESeq2 provides statistical routines for determining differential expression in digital gene expression data using a model based on the negative binomial distribution. The resulting p-values were adjusted using the Benjamini and Hochberg's approach for controlling the False Discovery Rate (FDR). Genes with an adjusted p-value <0.05 found by DESeq2 were assigned as differentially expressed.

For edgeR without biological replicates, prior to differential gene expression analysis, for each sequenced library, the read counts were adjusted by edgeR program package through one scaling normalized factor. Differential expression analysis of two conditions was performed using the edgeR R package (3.16.5). The p values were adjusted using the Benjamini & Hochberg method. Corrected p-value of 0.05 and absolute fold change of 1 were set as the threshold for significantly differential expression.

RNAseq (Novogene) Correlations

To allow for log adjustment, genes with 0 FPKM are assigned a value of 0.001. Correlation were determined using the cor.test function in R with options set alternative="greater" and method="Spearman".

RNAseq (Novogene) Clustering

To identify the correlation between difference, different samples were clustered using expression level FPKM to see the correlation using hierarchical clustering distance method with the function of heatmap, SOM (Self-organization mapping) and kmeans using silhouette coefficient to adapt the optimal classification with default parameter in R.

RNAseq (Novogene) GO and KEGG Enrichment Analysis of Differentially Expressed Genes Gene Ontology (GO) enrichment analysis of differentially expressed genes was implemented by the cluster Profiler R package, in which gene length bias was corrected. GO terms with a corrected p-value less than 0.05 were considered significantly enriched by differential expressed genes. KEGG is a database resource for understanding high-level functions and utilities of the biological system, such as the cell, the organism and the ecosystem, from molecular level information, especially large-scale molecular datasets generated by genome sequencing and other high-through put experimental technologies. Cluster Profiler R package was used to test the statistical enrichment of differential expression genes in KEGG pathways.

Advantages of the present disclosure may include cytokine sensitivity assays that may be used to determine which types of in vitro manufactured T cells that may potentially persist in vivo by increasing proliferation and survival and decreasing apoptosis of transferred cells in a high-throughput patient specific fashion, thus, improve tumor regression and increase efficacy of ACT.

The invention claimed is:

1. A method of producing T cells comprising
   (a) activating T cells obtained from at least one individual,
   (b) expanding a first portion of the activated T cells over a plurality of different periods of time selected from about 1 day to about 15 days after the activating,
   (c) culturing the expanded first portion of the activated T cells in (b) in the presence of at least one cytokine and in the absence of antigen presenting cells over a period of at least 21 days,
   (d) measuring a cytokine response in the cultured T cells in (c) in the absence of continual cytokine stimulation,
   (e) comparing the cytokine response in (d) to identify a period of time from the plurality of different periods of time in (b) that yields a maximum cytokine response in (d), and
   (f) expanding a second portion of the activated T cells in (a) for the period of time identified in (e) that yields the maximum cytokine response in (d),
   wherein the cytokine response comprises an increased population of naïve T cells ($T_N$) and stem memory T cells ($T_{scm}$).

2. The method of claim 1, further comprising freezing the expanded first portion of the activated T cells prior to culturing.

3. The method of claim 2, further comprising thawing the frozen expanded first portion of activated T cells prior to culturing.

4. The method of claim 3, further comprising resting the thawed expanded first portion of the activated T cells prior to culturing.

5. The method of claim 4, wherein the resting is carried out within a period of time from about 0.5 hour to about 48 hours, about 0.5 hour to about 36 hours, about 0.5 hour to about 24 hours, about 0.5 hour to about 18 hours, about 0.5 hour to about 12 hours, about 0.5 hour to about 6 hours, about 1 hour to about 6 hours, about 2 hours to about 5 hours, about 3 hours to about 5 hours, about 4 hours to 6 hours, about 1 hours to about 24 hours, about 2 to about 24 hours, about 12 to about 48 hours, about 0.5 hour to about 120 hours, about 0.5 hour to about 108 hours, about 0.5 hour to about 96 hours, about 0.5 hour to about 84 hours, about 0.5 hour to about 72 hours, or about 0.5 hour to about 60 hours.

6. The method of claim 1, wherein the T cells are activated by a stimulator comprising anti-CD3 antibody and an anti-CD28 antibody.

7. The method of claim 6, wherein the anti-CD3 antibody and the anti-CD28 antibody each have a concentration of from about 0.1 μg/ml to about 10.0 μg/ml, about 0.1 μg/ml to about 8.0 μg/ml, about 0.1 μg/ml to about 6.0 μg/ml, about 0.1 μg/ml to about 4.0 μg/ml, about 0.1 μg/ml to about 2.0 μg/ml, about 0.1 μg/ml to about 1.0 μg/ml, about 0.1 μg/ml to about 0.8 μg/ml, about 0.1 μg/ml to about 0.6 μg/ml, about 0.1 μg/ml to about 0.5 μg/ml, about 0.1 μg/ml to about 0.25 μg/ml, about 0.2 μg/ml to about 0.5 μg/ml, about 0.2 μg/ml to about 0.3 μg/ml, about 0.3 μg/ml to about 0.5 μg/ml, about 0.3 μg/ml to about 0.4 μg/ml, or about 0.4 μg/ml to about 0.5 μg/ml.

8. The method of claim 1, wherein the at least one cytokine is selected from the group consisting of interleukin 2 (IL-2), interleukin 7 (IL-7), interleukin 15 (IL-15), and a combination thereof.

9. The method of claim 8, wherein the at least one cytokine is IL-2.

10. The method of claim 8, wherein the at least one cytokine is IL-7.

11. The method of claim 8, wherein the at least one cytokine is IL-15.

12. The method of claim 8, wherein the concentration of IL-2 is from about 10 U/ml to about 500 U/ml, from about 10 U/ml to about 450 U/ml, from about 10 U/ml to about 400 U/ml, from about 10 U/ml to about 350 U/ml, from about 10 U/ml to about 300 U/ml, from about 10 U/ml to about 250 U/ml, from about 10 U/ml to about 200 U/ml, from about 10 U/ml to about 150 U/ml, from about 10 U/ml to about 100 U/ml, from about 10 U/ml to about 50 U/ml, from about 20 U/ml to about 40 U/ml, from about 25 U/ml to about 35 U/ml, or from about 30 U/ml to about 35 U/ml.

13. The method of claim 8, wherein the concentration of IL-7 is from 0.1 ng/ml to 50 ng/ml, from 0.1 ng/ml to 45 ng/ml, from 0.1 ng/ml to 40 ng/ml, from 0.1 ng/ml to 35 ng/ml, from 0.1 ng/ml to 30 ng/ml, from 0.1 ng/ml to 25 ng/ml, from 0.1 ng/ml to 20 ng/ml, from 0.1 ng/ml to 15 ng/ml, from 0.1 ng/ml to 10 ng/ml, from 0.1 ng/ml to 5 ng/ml, from 0.1 ng/ml to 4 ng/ml, from 0.1 ng/ml to 3 ng/ml, from 0.1 ng/ml to 2 ng/ml, from 0.1 ng/ml to 1 ng/ml, or from 0.1 ng/ml to 0.5 ng/ml.

14. The method of any one of claim 8, wherein the concentration of IL-15 is from 0.1 ng/ml to 50 ng/ml, from 0.1 ng/ml to 45 ng/ml, from 0.1 ng/ml to 40 ng/ml, from 0.1 ng/ml to 35 ng/ml, from 0.1 ng/ml to 30 ng/ml, from 0.1 ng/ml to 25 ng/ml, from 0.1 ng/ml to 20 ng/ml, from 0.1 ng/ml to 15 ng/ml, from 0.1 ng/ml to 10 ng/ml, from 0.1 ng/ml to 5 ng/ml, from 0.1 ng/ml to 4 ng/ml, from 0.1 ng/ml to 3 ng/ml, from 0.1 ng/ml to 2 ng/ml, from 0.1 ng/ml to 1 ng/ml, or from 0.1 ng/ml to 0.5 ng/ml.

15. The method of claim 1, wherein the cytokine response further comprises increased proliferation and/or reduced apoptosis.

16. The method of claim 15, wherein the cytokine response further comprises increased proliferation and reduced apoptosis.

17. The method of claim 1, wherein the obtained T cell is a CD3+ CD8+ T cell.

18. The method of claim 1, wherein the culturing in (c) is performed for 21 days.

19. The method of claim 1, wherein the period of time identified in (e) is about 3 to about 5 days.

20. The method of claim 1, wherein the cytokine response further comprises an increased population of T central memory ($T_{cm}$).

* * * * *